(12) United States Patent
Yoo et al.

(10) Patent No.: US 11,420,978 B2
(45) Date of Patent: Aug. 23, 2022

(54) METHOD FOR SYNTHESIZING 3-PHENYL-2,8-DIHYDROPYRANO [2,3-F] CHROMENE DERIVATIVE

(71) Applicant: GLACEUM INC., Gyeonggi-do (KR)

(72) Inventors: Sang Ku Yoo, Gyeonggi-do (KR); Jin Wook Chung, Seoul (KR); In Geun Jo, Chungcheongnam-do (KR); Ji Young Kim, Seoul (KR); Jeong Ho Im, Gyeonggi-do (KR); Ku Suk Kang, Gyeonggi-do (KR); Jin Young Kim, Gyeonggi-do (KR)

(73) Assignee: GLACEUM INC.

( * ) Notice: Subject to any disclaimer, the term of this patent is extended or adjusted under 35 U.S.C. 154(b) by 51 days.

(21) Appl. No.: 17/044,481

(22) PCT Filed: Apr. 3, 2019

(86) PCT No.: PCT/KR2019/003958
§ 371 (c)(1),
(2) Date: Oct. 1, 2020

(87) PCT Pub. No.: WO2019/194582
PCT Pub. Date: Oct. 10, 2019

(65) Prior Publication Data
US 2021/0040106 A1  Feb. 11, 2021

(30) Foreign Application Priority Data

Apr. 3, 2018  (KR) .......................... 10-2018-0038894

(51) Int. Cl.
*C07D 493/04*  (2006.01)
(52) U.S. Cl.
CPC .................... *C07D 493/04* (2013.01)

(58) Field of Classification Search
CPC ................................................ C07D 493/04
See application file for complete search history.

(56) References Cited

U.S. PATENT DOCUMENTS

2008/0188549 A1  8/2008  Tanaka et al.

FOREIGN PATENT DOCUMENTS

| CN | 103030647 | 4/2013 |
| WO | 2005/037815 | 4/2005 |

OTHER PUBLICATIONS

Kuroda et al. Bioorg. Med. Chem. 2010, 18, 962-970 (Year: 2010).*
International Search Report, dated Jul. 17, 2019 in corresponding International Patent Application No. PCT/KR2019/003958, with English language translation.
Kuroda et al., "Phenolics from *Glycyrrhiza glabra* roots and their PPAR-y ligand-binding activity", Bioorganic & Medicinal Chemistry, 18(2): 962-970 (2010).
Yoo et al., "Facile and Efficient Synthesis of (±)-Glabridin", Bulletin of the Korean Chemical Society, 28(3): 481-484 (2007).
Yenesew et al., "The antiplasmodial and radical scavenging activities of flavonoids of *Erythrina burttii*", Acta Tropica, 123(2): 123-127 (2012).

* cited by examiner

*Primary Examiner* — Matthew P Coughlin
(74) *Attorney, Agent, or Firm* — Wenderoth, Lind & Ponack, L.L.P.

(57) ABSTRACT

The present invention relates to a method for synthesizing a 3-phenyl-2,8-dihydropyrano[2,3-f]chromene derivative, which may be usefully used for synthesizing a pyranochromenyl phenol derivative, and when the derivative is used, the 3-phenyl-2,3,4,8,9,10-hexahydropyrano[2,3-f] chromene derivative may be effectively prepared.

9 Claims, No Drawings

METHOD FOR SYNTHESIZING 3-PHENYL-2,8-DIHYDROPYRANO [2,3-F] CHROMENE DERIVATIVE

TECHNICAL FIELD

This application claims priority to and the benefit of Korean Patent Application No. 10-2018-0038894 filed in the Korean Intellectual Property Office on Apr. 3, 2018, the entire contents of which are incorporated herein by reference.

The present invention relates to a method for synthesizing a 3-phenyl-2,8-dihydropyrano[2,3-f]chromene derivative, which may be usefully used for synthesizing a pyranochromenyl phenol derivative.

BACKGROUND ART

About 20 billion or more adipocytes are present in the human body, and when much more energy is supplied to the human body than the need for energy, energy is stored as triglyceride in adipocytes in the human body, and when energy is used up, the triglyceride is decomposed into free fatty acid and glucose and thus is used as an energy source. Obesity, which about 30 to 40% of modern people suffer from, occurs when excessive energy is accumulated due to the imbalance of the procedure, and is shown as a phenomenon in which the size of adipocytes is increased or the number thereof is increased.

The metabolic syndrome conceptualizes a clustering phenomenon of risk factors of various cardiovascular diseases and type 2 diabetes as one disease group. The metabolic syndrome is a concept which may comprehensively explain insulin resistance and complicated and various metabolic abnormalities and clinical aspects associated with insulin resistance, and refers to a syndrome in which risk factors such as obesity, diabetes, fatty liver, and hypertriglyceridemia are together increased. Accordingly, in the case of a metabolic syndrome, the risk of incidence of a cardiovascular disease or type 2 diabetes is increased.

Insulin resistance refers to a phenomenon in which, even though insulin is normally secreted in the body, a supply of glucose into cells, which is performed by insulin, does not work properly. Since glucose in the blood cannot enter cells, hyperglycemia is exhibited, and cells cannot perform normal functions thereof due to a shortage of glucose, and as a result, metabolic syndrome symptoms are manifested.

The diabetic symptom thus manifested is called type 2 diabetes (non-insulin-dependent diabetes mellitus: NIDDM) which is differentiated from type 1 diabetes (insulin-dependent diabetes mellitus) resulting from a shortage of insulin. For this reason, the most preferable method of treating type 2 diabetes is to induce insulin to be capable of performing normal functions thereof by alleviating insulin resistance. Nevertheless, a therapeutic agent of alleviating insulin resistance has hardly been developed up until now.

Most of the type 2 diabetes therapeutic agents currently used or developed aim to increase the amount of insulin secreted in order to supplement the functions of insulin lost by insulin resistance. However, when the amount of insulin secreted is increased in our bodies, not only obesity and inflammation are caused, but also various side effects such as an increase in cancer incidence rate are accompanied, so that unless the insulin resistance problem is fundamentally solved, it is possible to expect that blood sugar is only temporarily normalized, but the health deteriorates more and more. For this reason, there is a more desperate social need for a type 2 diabetes therapeutic agent capable of normalizing blood sugar by alleviating insulin resistance.

Meanwhile, Patent Document 1 discloses that a pyranochromenyl phenol derivative is effective for preventing and treating a metabolic syndrome including hyperlipidemia, fatty liver, sugar metabolic abnormality, diabetes, and obesity, and have effects such as anti-inflammatory action and anticancer action.

Therefore, even though a method for efficiently and economically synthesizing the pyranochromenyl phenol derivative is very useful, a method for synthesizing the pyranochromenyl phenol derivative has been little known up until now, except for a method established based on a method for synthesizing (±)-glabridin (Non-Patent Document 1) developed by the present inventors.

PRIOR ART DOCUMENT

Patent Document

Korean Patent Application Laid-Open No. 10-2015-0075030

Non-Patent Documents

Sang-Ku Yoo, Keepyung Nahm; Bull. Korean Chem. Soc. 2007(28) 481484

SUMMARY OF THE INVENTION

The present invention has been made in an effort to provide a method for synthesizing a 3-phenyl-2,8-dihydropyrano[2,3-f]chromene derivative, which may be usefully used for preparing a 3-phenyl-2,3,4,8,9,10-hexahydropyrano[2,3-f]chromene derivative.

An exemplary embodiment of the present invention provides a method for synthesizing a 3-phenyl-2,8-dihydropyrano[2,3-f]chromene derivative of Formula (I), the method including:

A) preparing a compound of Formula 3 by coupling a compound represented by Formula 1 with a compound represented by Formula 2;

B) synthesizing a compound of Formula 4 by cyclizing the compound of Formula 3;

C) preparing a compound of Formula 5 by reducing the compound of Formula 4; and

D) preparing a compound of Formula (I) by subjecting the compound of Formula 5 to a reductive elimination reaction:

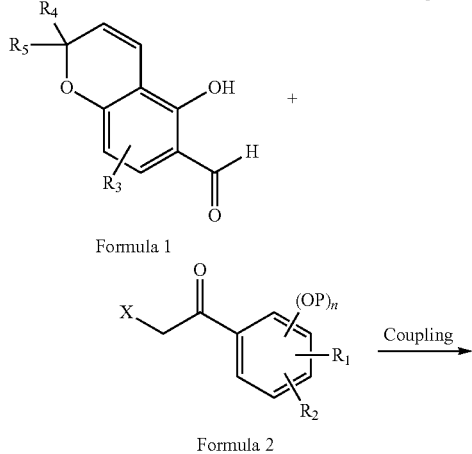

[Reaction Formula 1]

Formula 1

Formula 2

Coupling

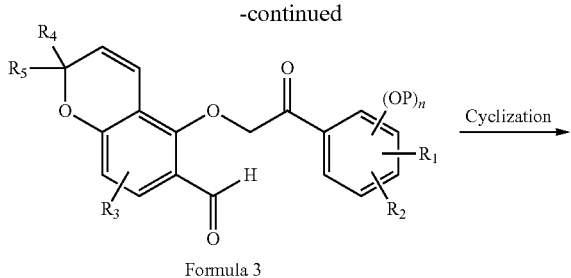

Formula 3

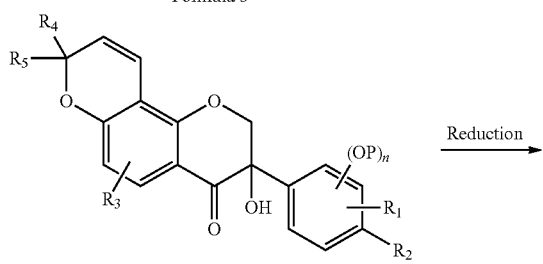

Formula 4

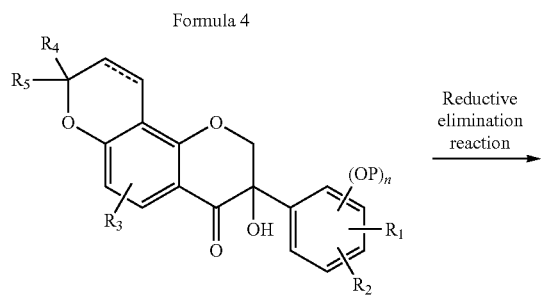

Formula 5

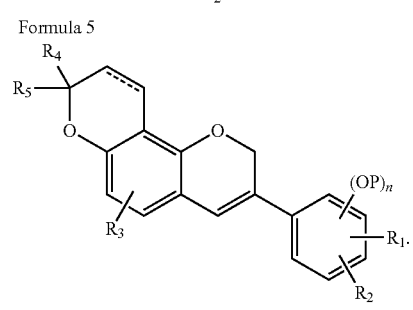

Formula (I)

in the formulae, $R_1$ and $R_2$ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

$R_3$ is a hydrogen atom, a $C_1$ to $C_2$ alkyl group, or a $C_1$ to $C_2$ alkoxy group;

$R_4$ and $R_5$ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

a dotted line is a selective double bond;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

Another exemplary embodiment of the present invention provides a compound represented by the following Formula 4, a salt or solvate thereof:

[Formula 4]

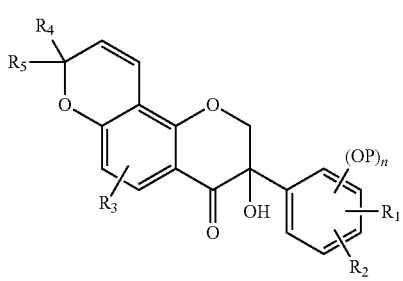

In the formula, $R_1$ and $R_2$ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

$R_3$ is a hydrogen atom, a $C_1$ to $C_2$ alkyl group, or a $C_1$ to $C_2$ alkoxy group;

$R_4$ and $R_5$ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

Yet another exemplary embodiment of the present invention provides a compound represented by the following Formula 4-b, a salt or solvate thereof:

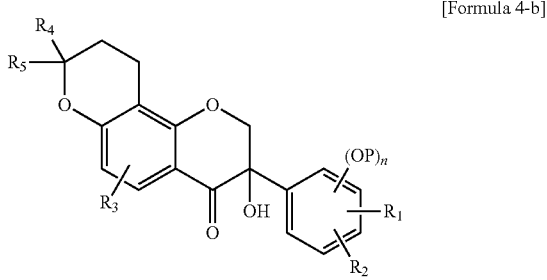

[Formula 4-b]

In Formula 4-b, $R_1$ to $R_5$, P, and n are the same as those defined in Formula 4.

Still another exemplary embodiment of the present invention provides a compound represented by the following Formula 5, a salt or solvate thereof:

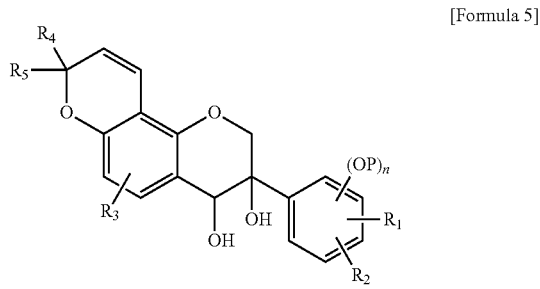

[Formula 5]

In the formula, $R_1$ and $R_2$ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

$R_3$ is a hydrogen atom, a $C_1$ to $C_2$ alkyl group, or a $C_1$ to $C_2$ alkoxy group;

$R_4$ and $R_5$ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

a dotted line is a selective double bond;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

According to the synthesis method of the present invention, it is possible to effectively prepare a 3-phenyl-2,8-dihydropyrano[2,3-f]chromene derivative.

DETAILED DESCRIPTION

Hereinafter, the present invention will be described in more detail.

All the technical terms used in the present invention are used in the same sense as those generally understood by the person skilled in the art related to the present invention, unless otherwise defined. Further, in the present specification, a preferred method or sample is described, but those similar or equivalent thereto also fall within the scope of the present invention. The contents of all the publications described as a reference document in the present specification are incorporated into the present specification by reference.

A method for synthesizing a 3-phenyl-2,8-dihydropyrano[2,3-f]chromene derivative of Formula (I) according to an exemplary embodiment of the present invention includes:

A) preparing a compound of Formula 3 by coupling a compound represented by Formula 1 with a compound represented by Formula 2;

B) synthesizing a compound of Formula 4 by cyclizing the compound of Formula 3;

C) preparing a compound of Formula 5 by reducing the compound of Formula 4; and

D) preparing a compound of Formula (I) by subjecting the compound of Formula 5 to a reductive elimination reaction:

[Reaction Formula 1]

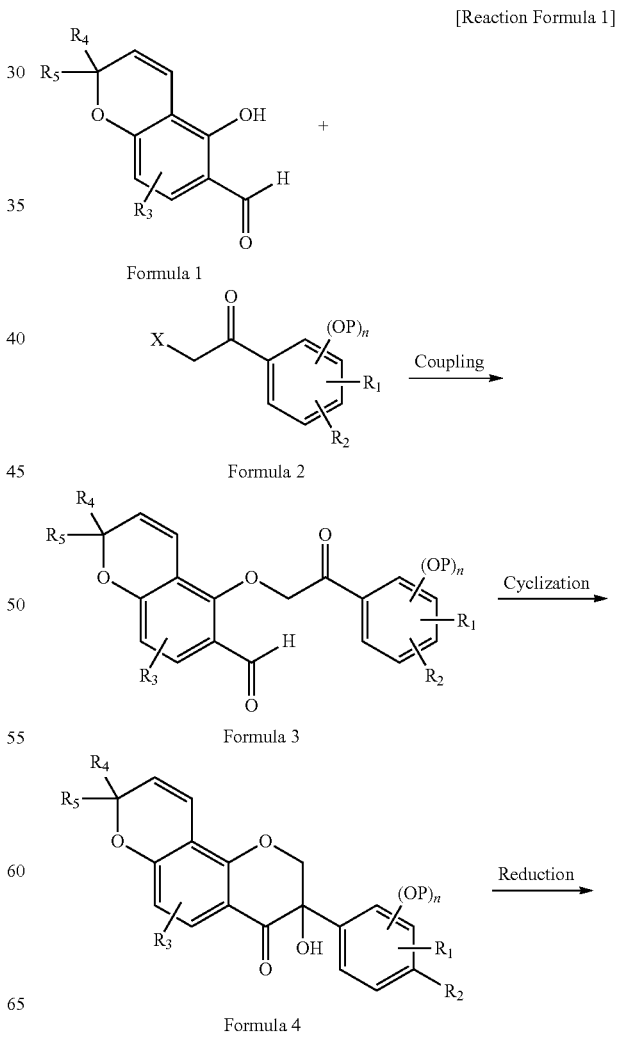

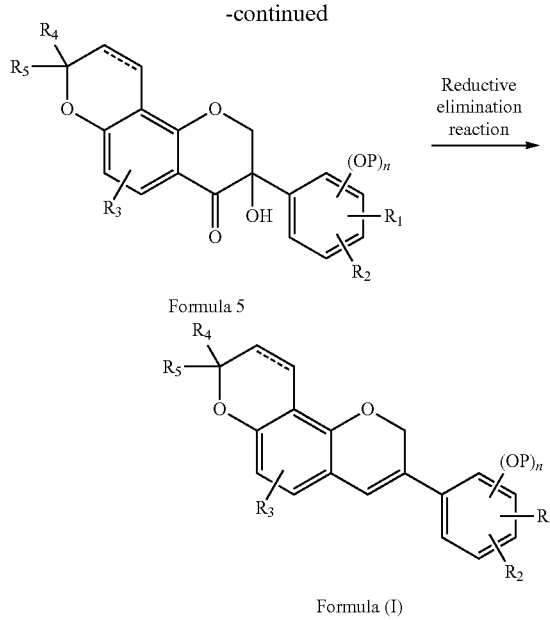

Formula 5

Formula (I)

in the formulae, $R_1$ and $R_2$ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

$R_3$ is a hydrogen atom, a $C_1$ to $C_2$ alkyl group, or a $C_1$ to $C_2$ alkoxy group;

$R_4$ and $R_5$ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

a dotted line is a selective double bond;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

The aforementioned "selective double bond" may mean a single bond or a double bond in some cases.

According to an exemplary embodiment of the present invention, the coupling reaction may be performed under basic conditions. Specifically, it is preferred that the coupling of the compound of Formula 1 with the compound of Formula 2 is performed under basic conditions, and it is further preferred that the coupling of the compound of Formula 1 with the compound of Formula 2 is performed by using a weak basic compound as a catalyst. In this case, an intramolecular aldol condensation reaction may prevent an undesired compound from being synthesized.

Furthermore, according to an exemplary embodiment of the present invention, the weak basic compound may be one or more selected from the group consisting of ammonia ($NH_3$), aluminum hydroxide ($Al_2(OH)_3$), magnesium hydroxide ($Mg(OH)_2$), ammonium hydroxide ($NH_3.H_2O$), and potassium carbonate ($K_2CO_3$), and is preferably potassium carbonate.

The derivatives of Formula 1 may be synthesized by the method of [Tetrahedron, 57 (2001), 5335~5338], and the derivatives of Formula 2 may be synthesized by allowing acetophenone derivatives, which may be synthesized by typical methods, to react with a bromination reagent such as tetrabutylammonium tribromide ($Bu_4NBr_3$) and benzyltrimethylammonium tribromide ($BnMe_3NBr_3$).

According to an exemplary embodiment of the present invention, the compound of Formula 4 may be obtained by adding a salt to the compound of Formula 3 and performing a cyclization process through a benzoin condensation reaction. Specifically, the salt may be a triazolium salt, a triazolium salt, or a 6,7-dihydro-5H-pyrrolo[2,1-c][1,2,4]triazolium salt.

According to an exemplary embodiment of the present invention, the compound represented by Formula 5 may be obtained by reducing a carbonyl group in the compound of Formula 4 to a hydroxyl group. Further, after a carbon-to-carbon double bond of a dihydropyran ring in the compound of Formula 4 is reduced in some cases, the compound represented by Formula 5 may be obtained by reducing a carbonyl group in the compound of Formula 4 to a hydroxyl group.

According to an exemplary embodiment of the present invention, the 3-phenyl-2,8-dihydropyrano[2,3-f]chromene derivative of Formula (I) may be synthesized from the compound of Formula 5 through a reductive elimination reaction.

According to an exemplary embodiment of the present invention, it is preferred that the reductive elimination reaction is performed in the presence of low valent titanium (LVT). Here, the low valent titanium means a zerovalent or monovalent titanium species produced when titanium tetrachloride ($TiCl_4$), titanium trichloride ($TiCl_3$), or the like is allowed to first react with a sufficient equivalent (two to three equivalents) of zinc (Zn), magnesium (Mg), lithium (Li), or the like.

According to an exemplary embodiment of the present invention, the 3-phenyl-2,8-dihydropyrano[2,3-f]chromene derivative may be a compound represented by the following Formula (I-a) or a compound represented by the following Formula (I-b).

[Formula (I-a)]

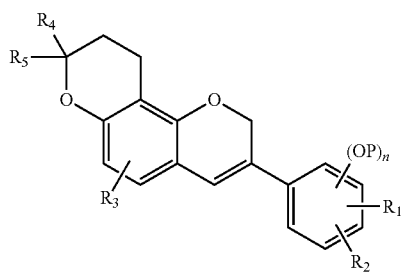

[Formula (I-b)]

In Formulae (I-a) and (I-b), $R_1$ to $R_5$, P, and n are the same as those defined in Formula (I).

An exemplary embodiment of the present invention provides a method for preparing a compound represented by Formula (I-a), the method including: a) preparing a compound of Formula 3 by coupling a compound represented by Formula 1 with a compound represented by Formula 2;

b) synthesizing a compound of Formula 4 by cyclizing the compound of Formula 3;

c) preparing a compound of Formula 5-a by reducing a carbonyl group in the compound of Formula 4 to a hydroxyl group; and d) preparing a compound of Formula (I-a) by subjecting the compound of Formula 5-a to a reductive elimination reaction:

[Reaction Formula 2]

Formula 1

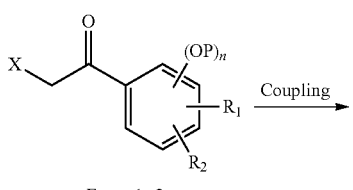

Formula 2

Coupling

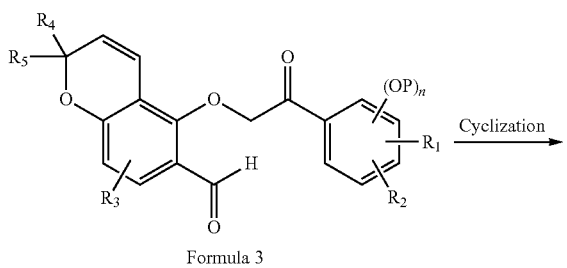

Formula 3

Cyclization

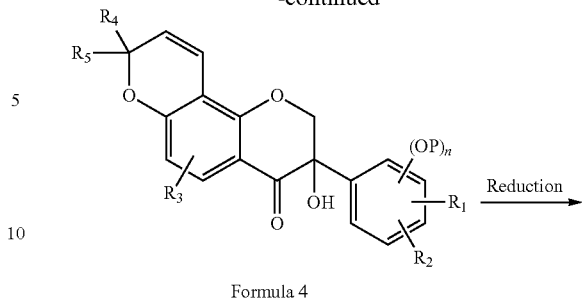

Formula 4

Reduction

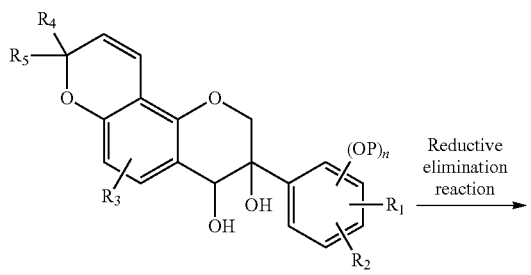

Formula 5-a

Reductive elimination reaction

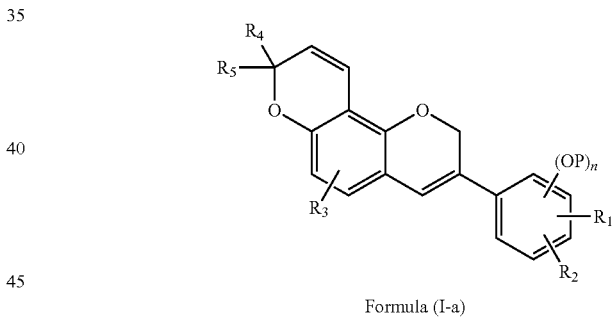

Formula (I-a)

In Reaction Formula 2, the coupling reaction, the cyclization reaction, and the reductive elimination reaction are the same as the above-described reactions in Reaction Formula 1.

According to an exemplary embodiment of the present invention, in Reaction Formula 2, the compound of Formula 5-a may be synthesized through a reaction of reducing a carbonyl group in the compound of Formula 4 to a hydroxyl group. Specifically, the reduction reaction may be performed by adding lithium borohydride ($LiBH_4$) or sodium borohydride ($NaBH_4$).

According to an exemplary embodiment of the present invention, in the method for synthesizing a 3-phenyl-2,8-dihydropyrano[2,3-f]chromene derivative, when the 3-phenyl-2,8-dihydropyrano[2,3-f]chromene derivative is the compound represented by Formula (I-b), Step C) may include preparing a compound represented by the following Formula 4-b by selectively reducing a carbon-to-carbon double bond of a dihydropyran ring in the compound represented by Formula 4.

[Formula 4-b]

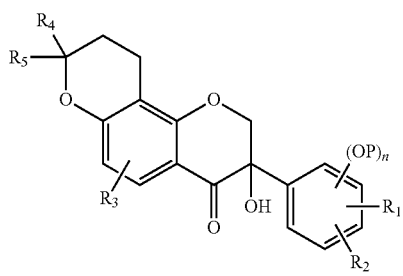

In Formula 4-b, $R_1$ to $R_5$, P, and n are the same as those defined in Formula (I).

That is, an exemplary embodiment of the present invention provides a method for preparing a compound represented by Formula (I-b), the method including: a') preparing a compound of Formula 3 by coupling a compound represented by Formula 1 with a compound represented by Formula 2;

b') synthesizing a compound of Formula 4 by cyclizing the compound of Formula 3;

c') preparing a compound of Formula 4-b by selectively reducing a carbon-to-carbon double bond of a dihydropyran ring in the compound of Formula 4;

d') preparing a compound of Formula 5-b by reducing a carbonyl group in the compound of Formula 4-b to a hydroxyl group; and e') preparing a compound of Formula (I-b) by subjecting the compound of Formula 5-b to a reductive elimination reaction:

[Reaction Formula 3]

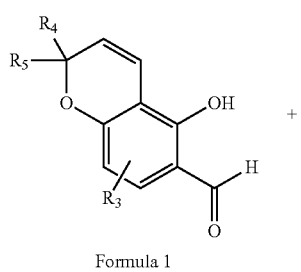

Formula 1

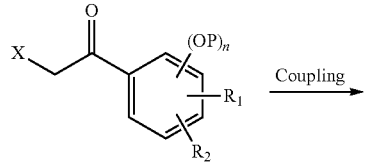

Formula 2

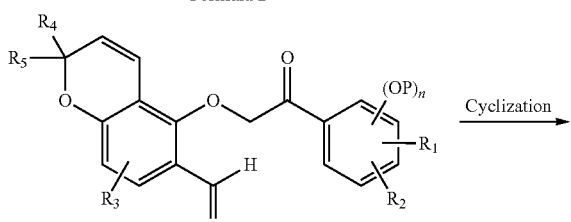

Formula 3

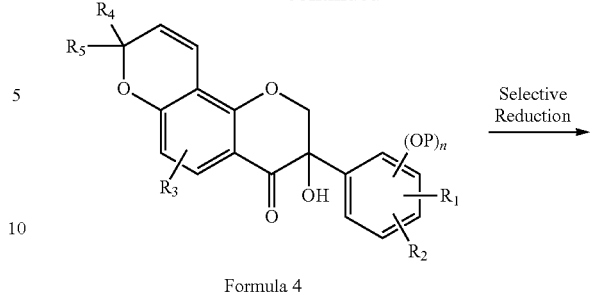

Formula 4

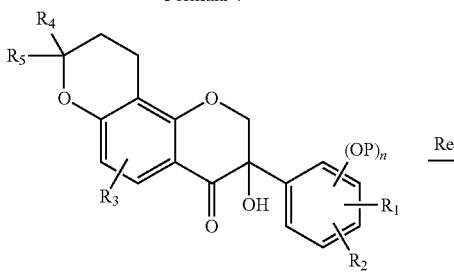

Formula 4-b

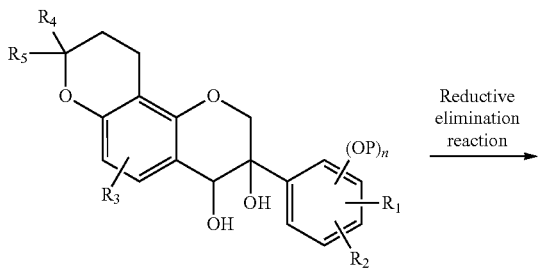

Formula 5-b

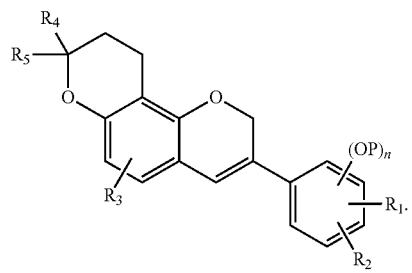

Formula (I-b)

In Reaction Formula 3, the coupling reaction, the cyclization reaction, and the reductive elimination reaction are the same as the above-described reactions in Reaction Formula 1. Further, in Reaction Formula 3, the reaction of reducing a carbonyl group in the compound of Formula 4-b to a hydroxyl group is the same as the above-described reaction in Reaction Formula 2.

According to an exemplary embodiment of the present invention, in Reaction Formula 3, the reaction of selectively reducing the carbon-to-carbon double bond of the dihydropyran ring in the compound of Formula 4 may be performed through a hydrogen addition reaction ($H_2$, Pd/C).

According to an exemplary embodiment of the present invention, during the selective reduction from Formula 4 to Formula 4-b, deprotection of a protecting group (P) in Formula 4 may be accompanied. In this case, an additional reaction of substituting the above-described protecting group may proceed at the position of a deprotected hydroxyl group.

According to an exemplary embodiment of the present invention, the compound of Formula (I-a) may be one or more of the following compounds:
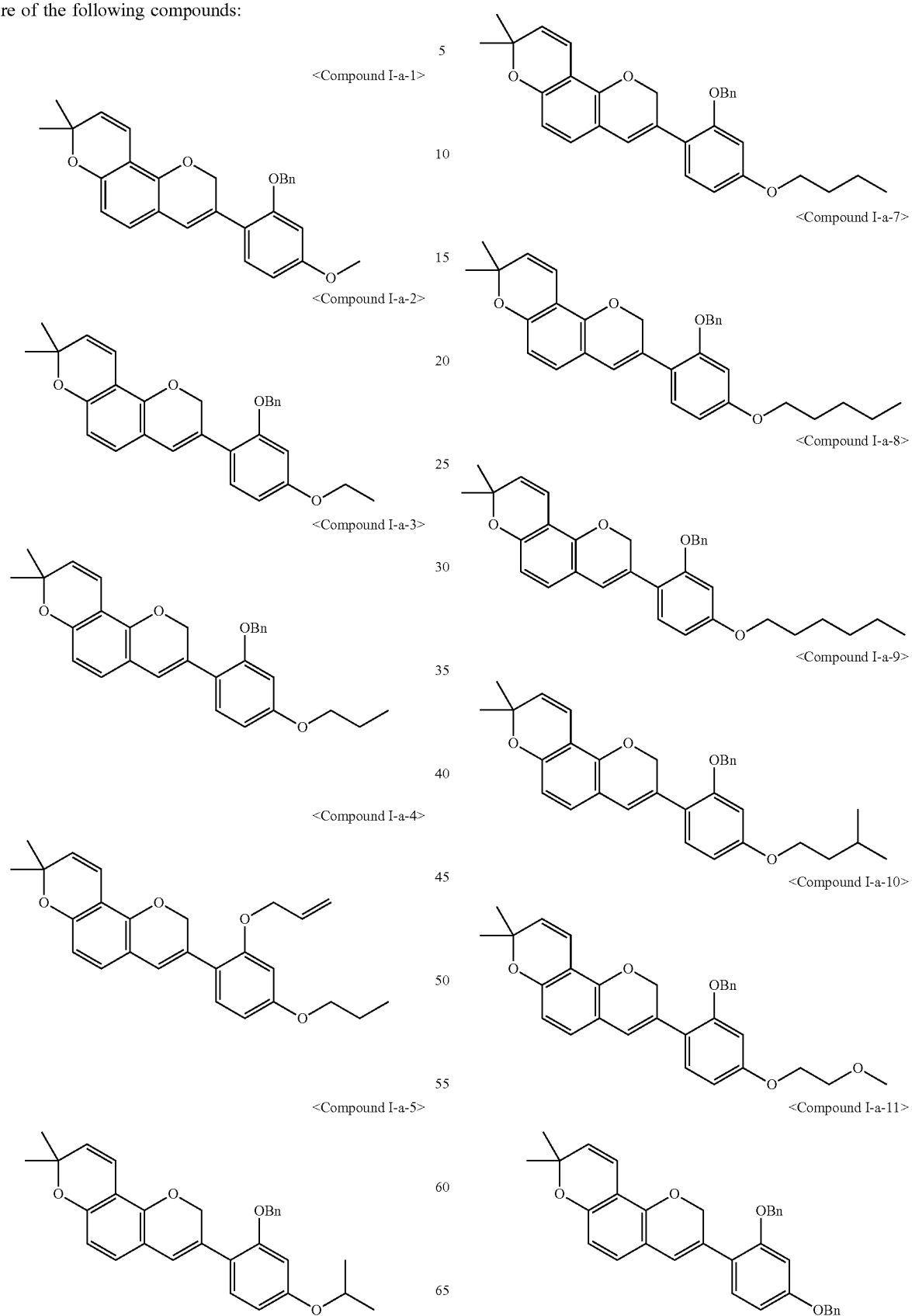

-continued
<Compound I-a-12>
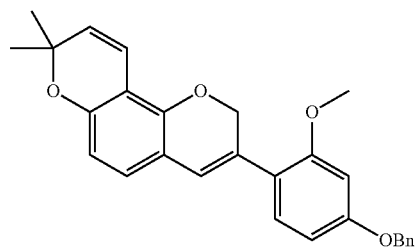
<Compound I-a-13>
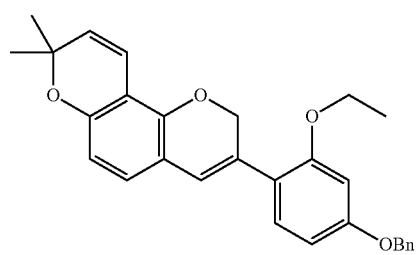
<Compound I-a-14>
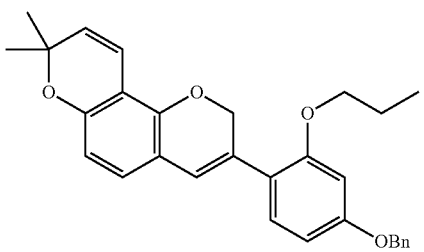
<Compound I-a-15>
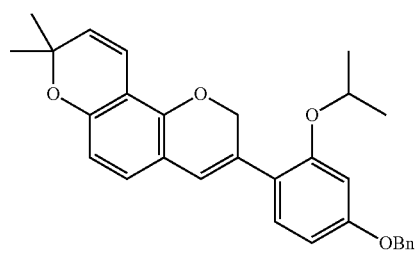
<Compound I-a-16>
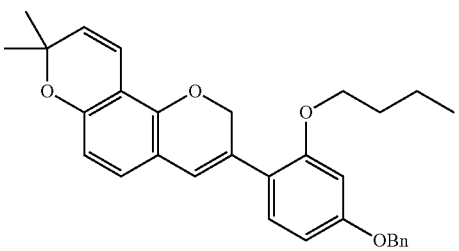
<Compound I-a-17>
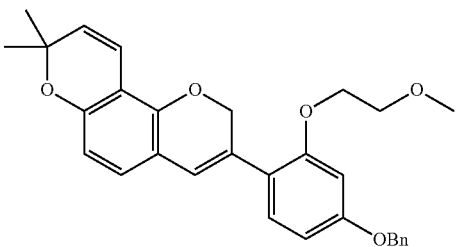
-continued
<Compound I-a-18>
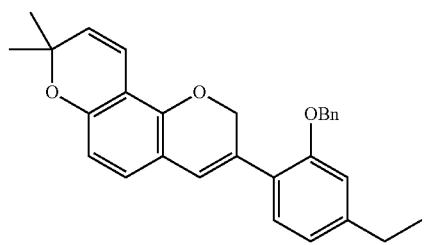
<Compound I-a-19>
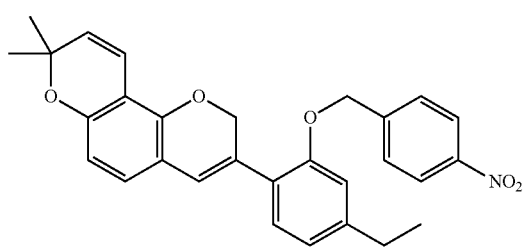
<Compound I-a-20>
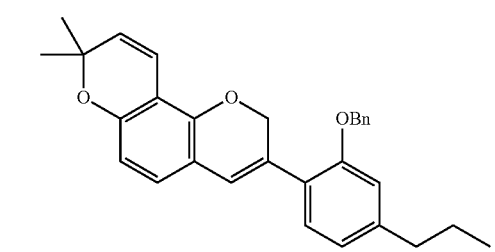
<Compound I-a-21>
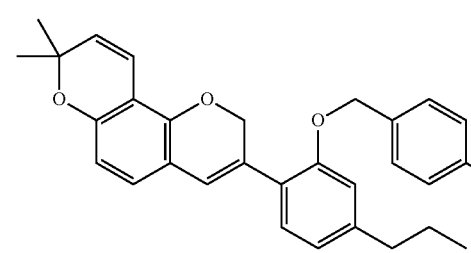
<Compound I-a-22>
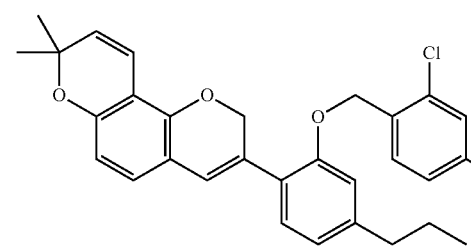
<Compound I-a-23>
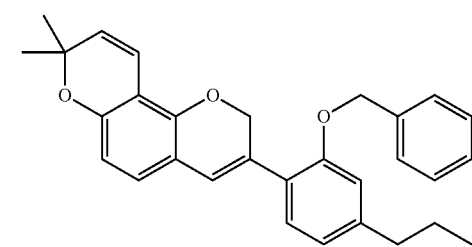

<Compound I-a-24>
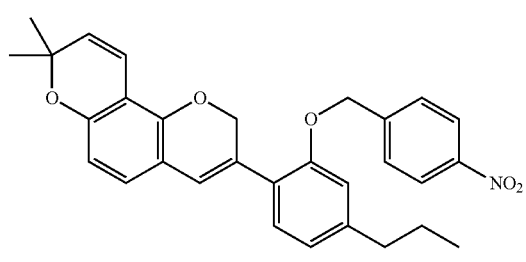
<Compound I-a-25>
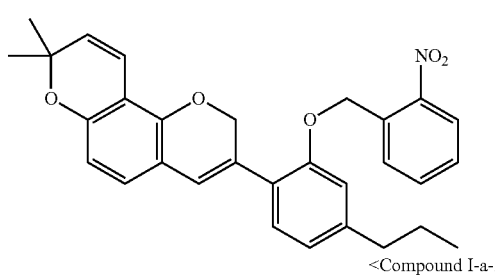
<Compound I-a-26>
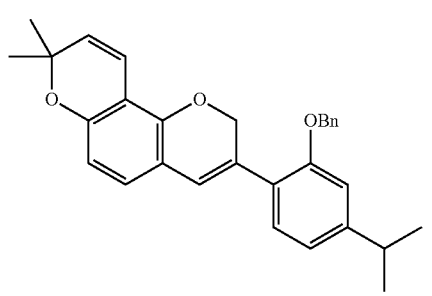
<Compound I-a-27>
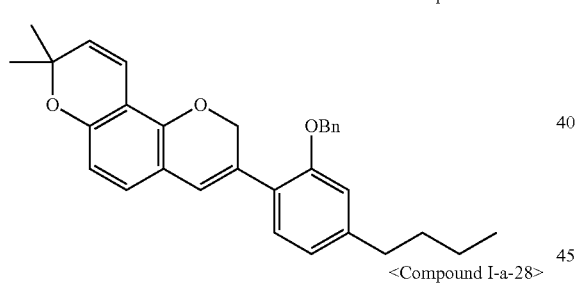
<Compound I-a-28>
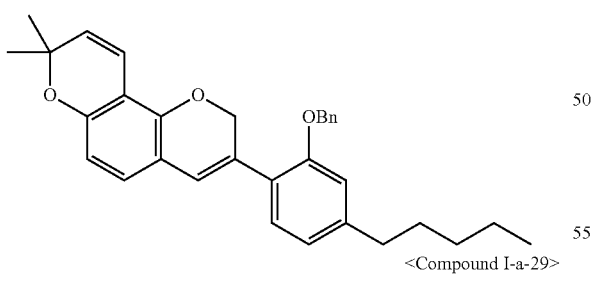
<Compound I-a-29>
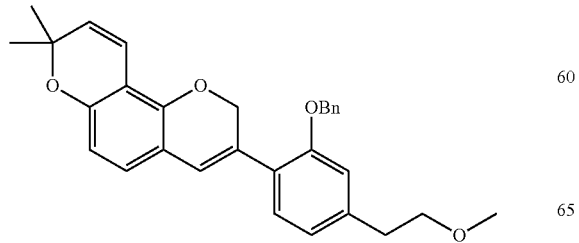
<Compound I-a-30>
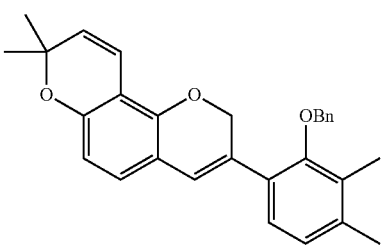
<Compound I-a-31>
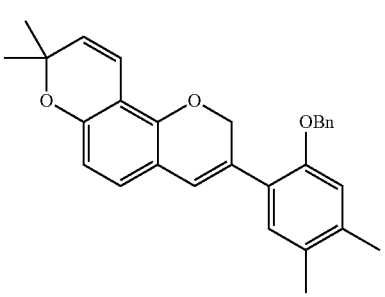
<Compound I-a-32>
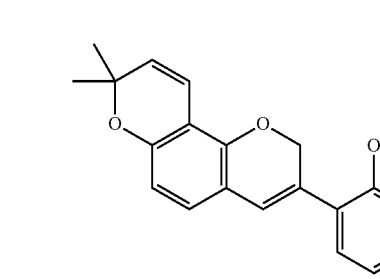
<Compound I-a-33>
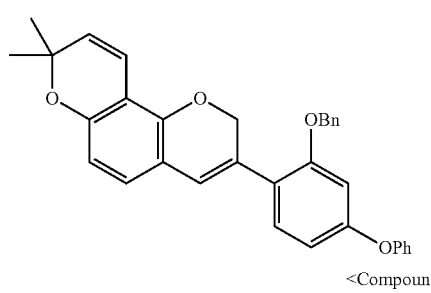
<Compound I-a-34>
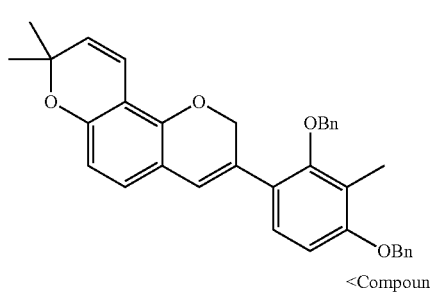
<Compound I-a-35>
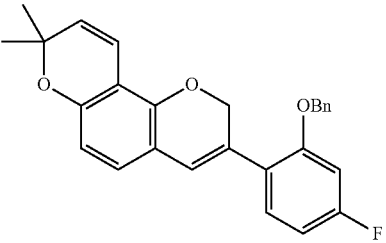

<Compound I-a-36>
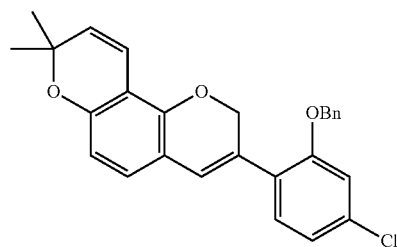
<Compound I-a-37>
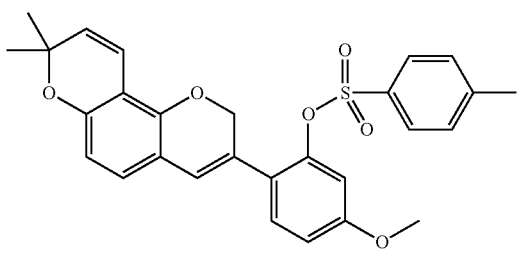
<Compound I-a-38>
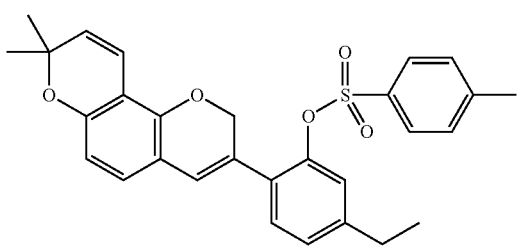
<Compound I-a-39>
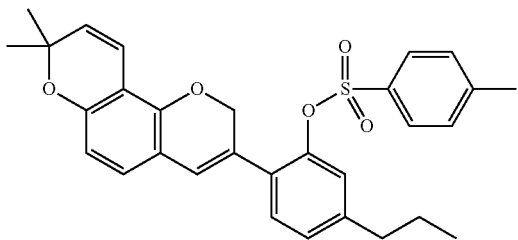
<Compound I-a-40>
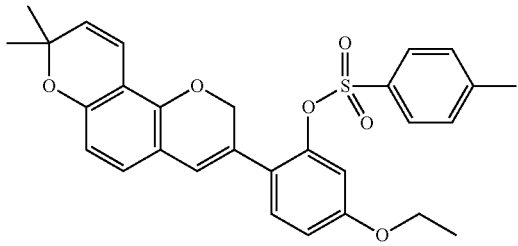
<Compound I-a-41>
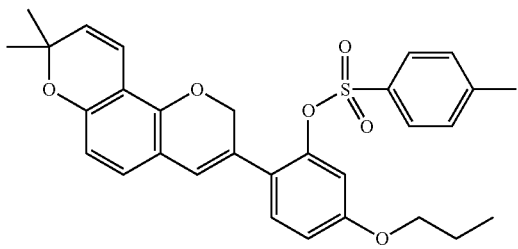
<Compound I-a-42>
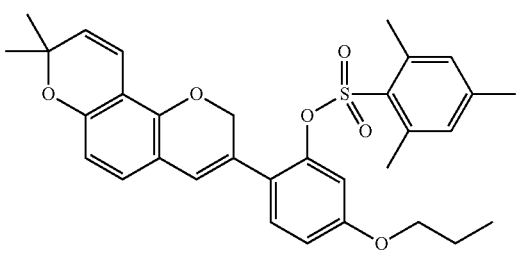
<Compound I-a-43>
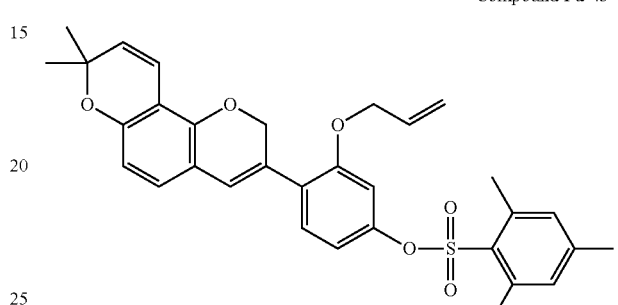
<Compound I-a-44>
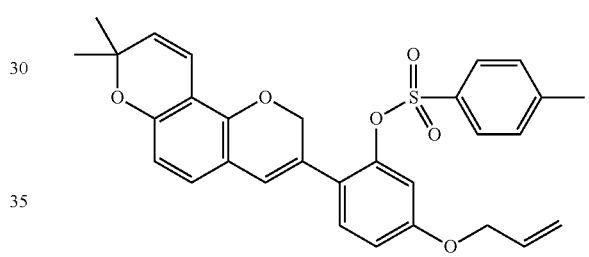
<Compound I-a-45>
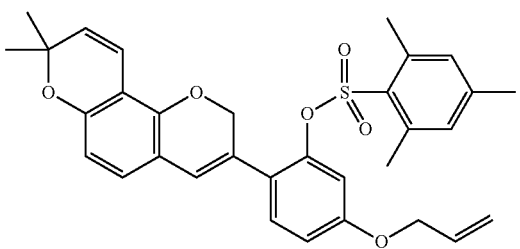
<Compound I-a-46>
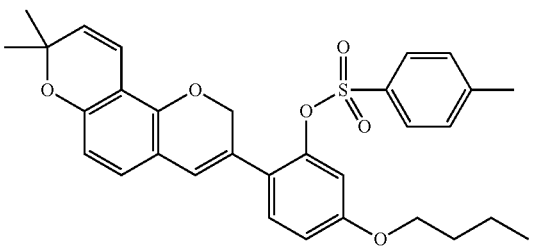

<Compound I-a-47>
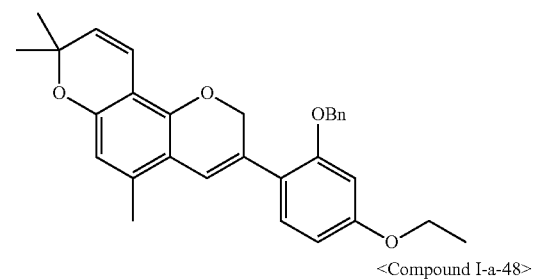
<Compound I-a-48>
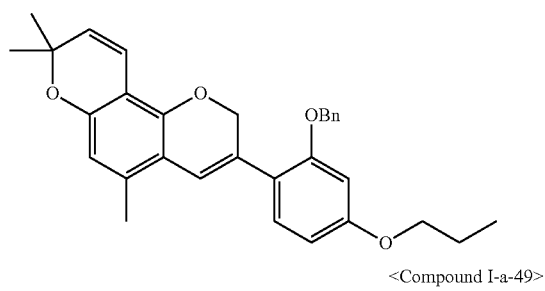
<Compound I-a-49>
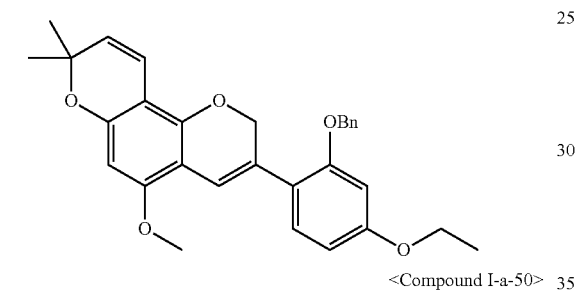
<Compound I-a-50>
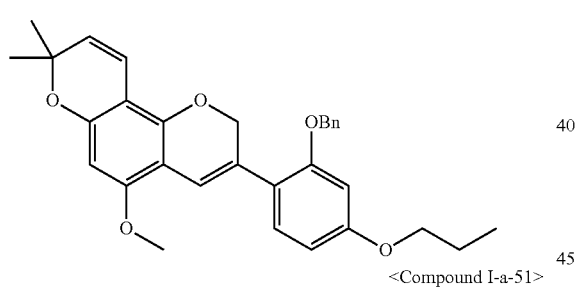
<Compound I-a-51>
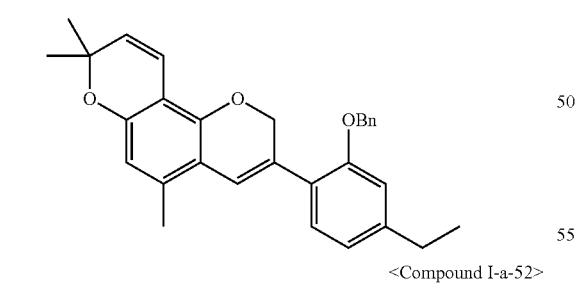
<Compound I-a-52>
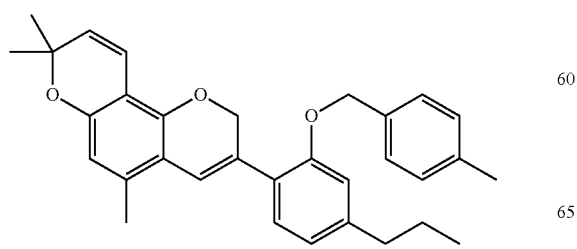
<Compound I-a-53>
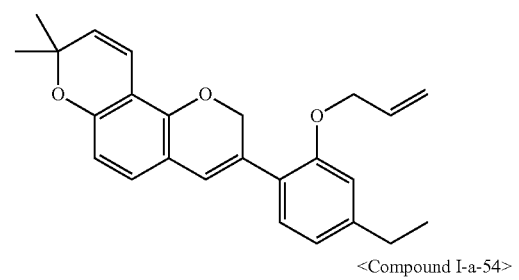
<Compound I-a-54>
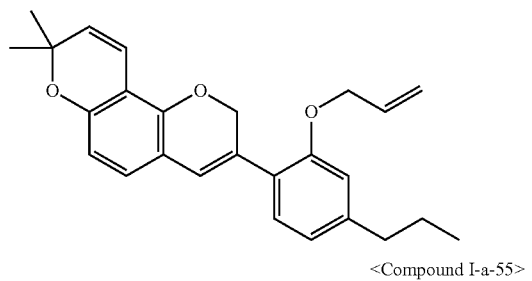
<Compound I-a-55>
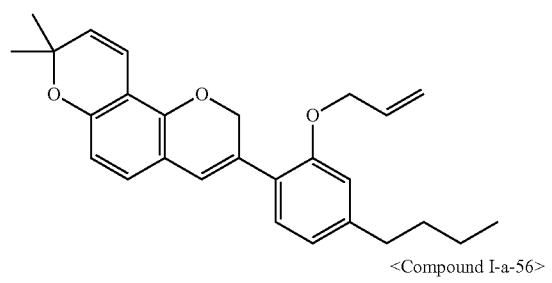
<Compound I-a-56>
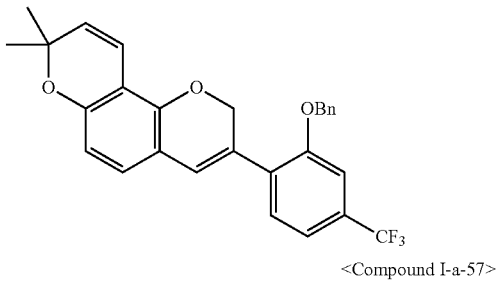
<Compound I-a-57>
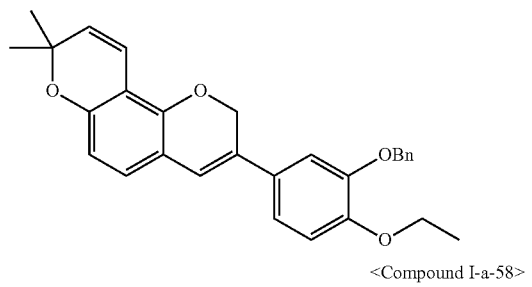
<Compound I-a-58>

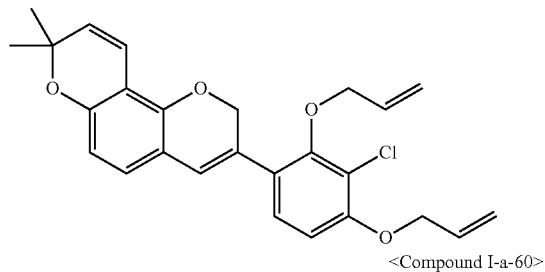

<Compound I-a-59>

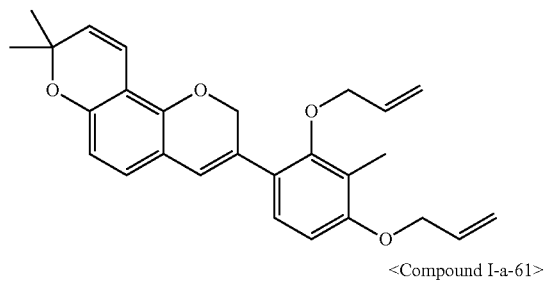

<Compound I-a-60>

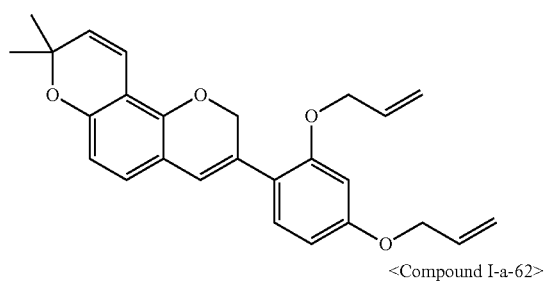

<Compound I-a-61>

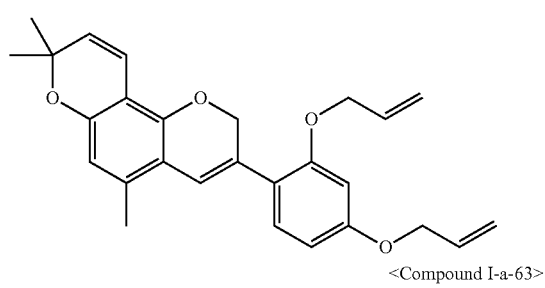

<Compound I-a-62>

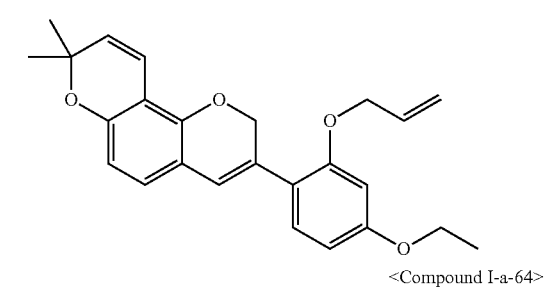

<Compound I-a-63>

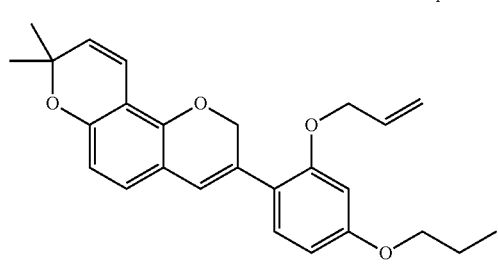

<Compound I-a-64>

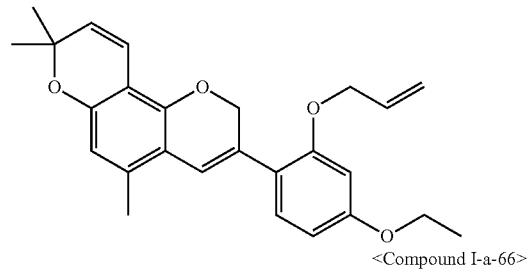

<Compound I-a-65>

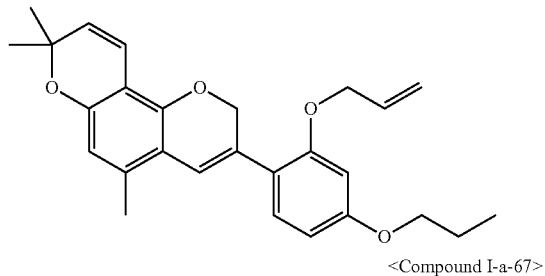

<Compound I-a-66>

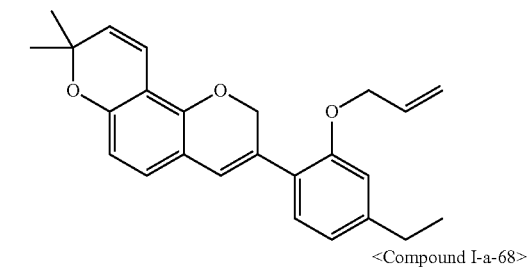

<Compound I-a-67>

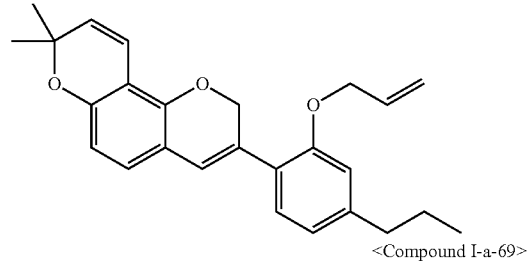

<Compound I-a-68>

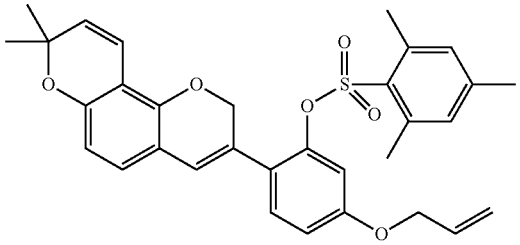

<Compound I-a-69>

According to an exemplary embodiment of the present invention, the compound of Formula (I-b) may corresponds to the respective Compounds I-a-1 to I-a-69, but be one or more of Compounds I-b-1 to I-b-69, which are compounds having no carbon-to-carbon double bond of a dihydropyran ring to which $R_4$ and $R_5$ are bonded.

According to an exemplary embodiment, it is possible to effectively synthesize a 3-phenyl-2,3,4,8,9,10-hexahydropyrano[2,3-f]chromene derivative of Formula (II), which is a pyranochromenyl phenol derivative having excellent anti-obese, anti-diabetic, and anti-inflammatory efficacies by using the compound of Formula (I).

[Formula (II)]

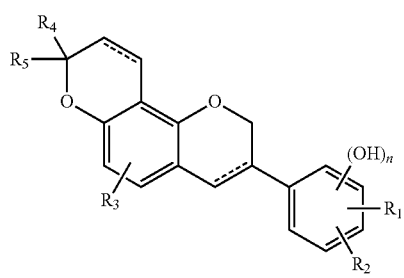

In Formula (II), the dotted line means a selective double bond. Further, in Formula (II), $R_1$ to $R_5$ and n are the same as those defined in Formula (I).

According to an exemplary embodiment of the present invention, the 3-phenyl-2,3,4,8,9,10-hexahydropyrano[2,3-f]chromene derivative of Formula (II) may be a compound represented by the following Formula (II-a), a compound represented by the following Formula (II-b), or a compound represented by the following Formula (II-c).

[Formula (II-a)]

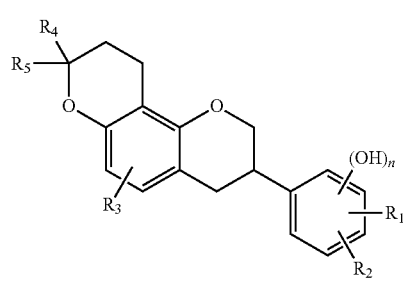

[Formula (II-b)]

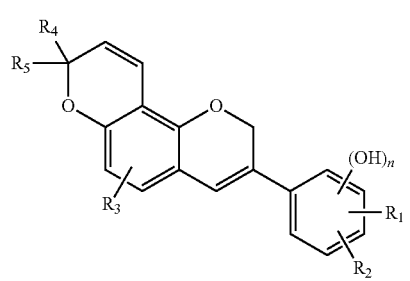

[Formula (II-c)]

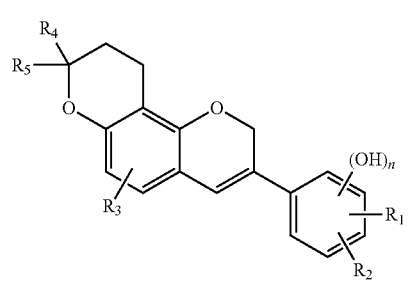

According to an exemplary embodiment of the present invention, the 3-phenyl-2,3,4,8,9,10-hexahydropyrano[2,3-f]chromene derivative of Formula (II-a) may be one or more of the following compounds:

<Compound II-a-1>

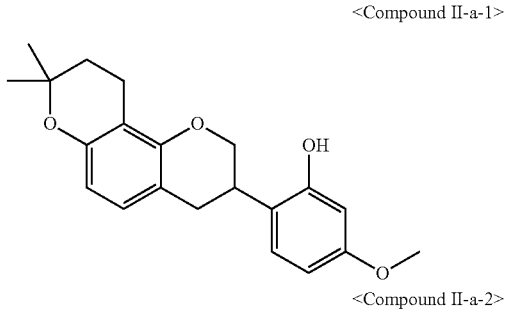

<Compound II-a-2>

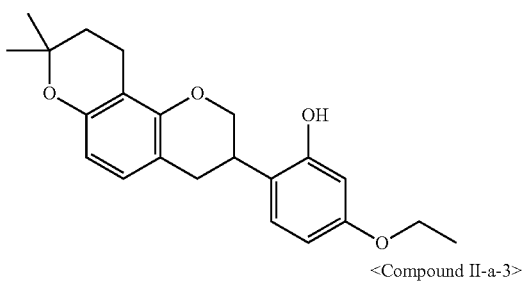

<Compound II-a-3>

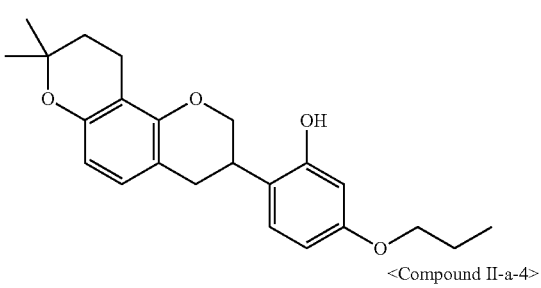

<Compound II-a-4>

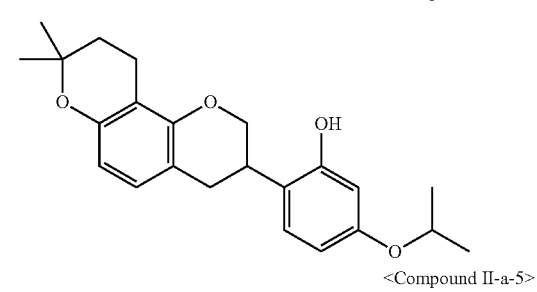

<Compound II-a-5>

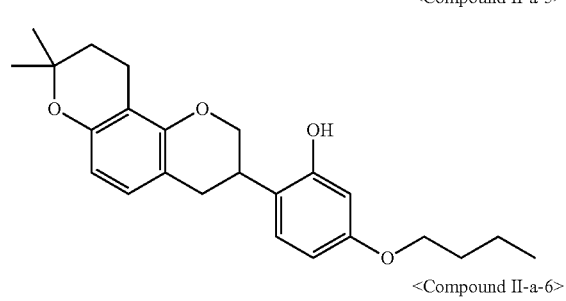

<Compound II-a-6>

-continued
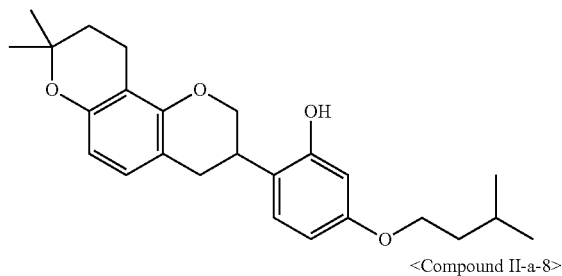
<Compound II-a-7>
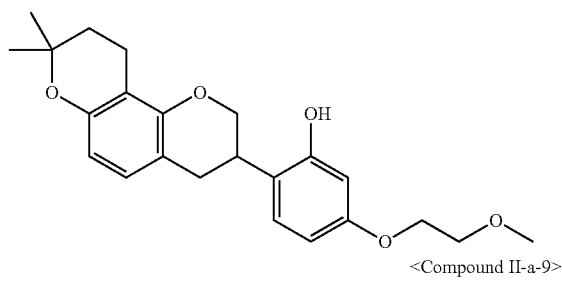
<Compound II-a-8>
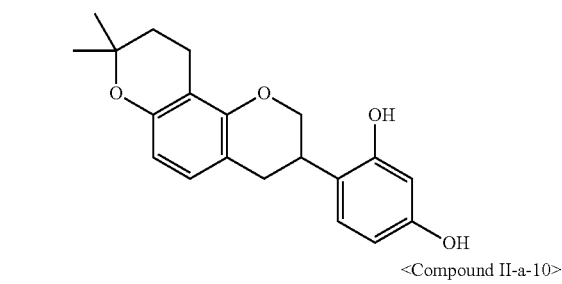
<Compound II-a-9>
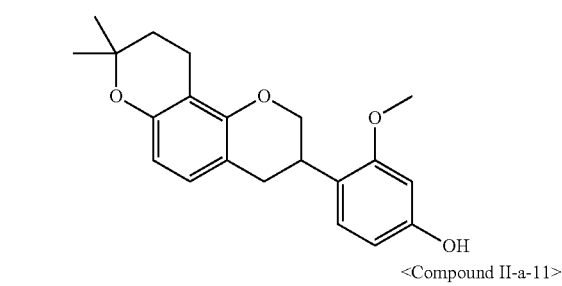
<Compound II-a-10>
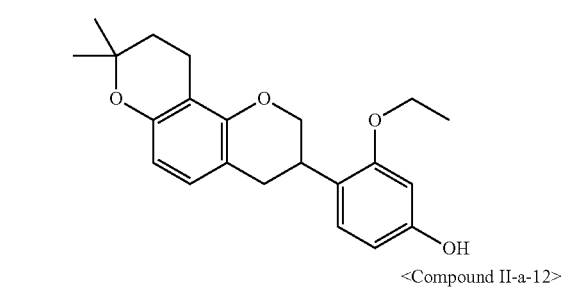
<Compound II-a-11>
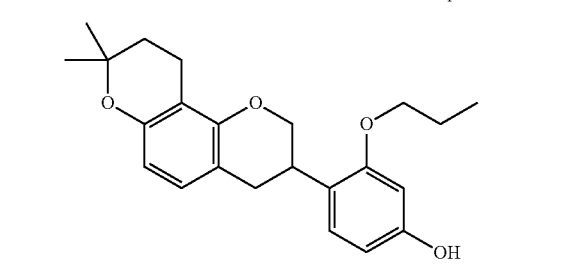
<Compound II-a-12>
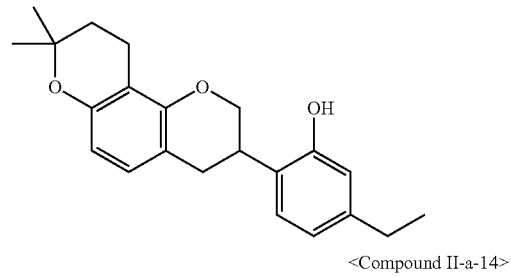
<Compound II-a-13>
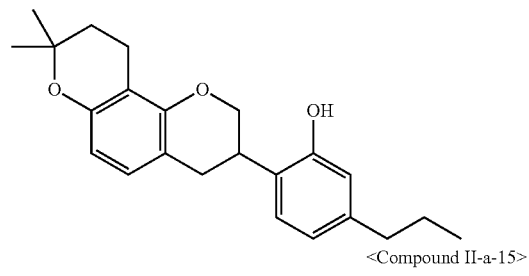
<Compound II-a-14>
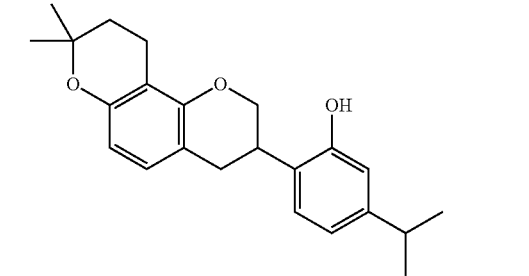
<Compound II-a-15>
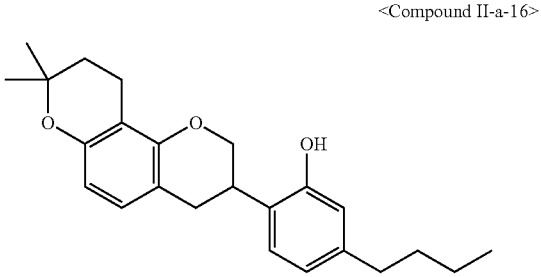
<Compound II-a-16>
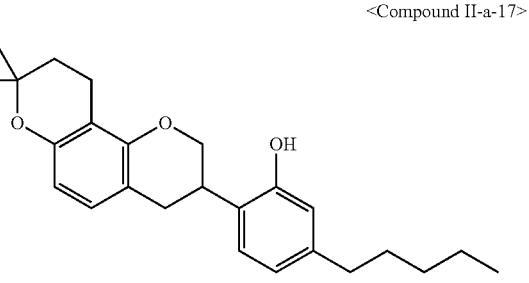
<Compound II-a-17>
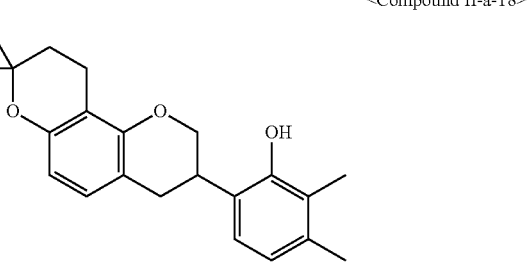
<Compound II-a-18>

<Compound II-a-19>
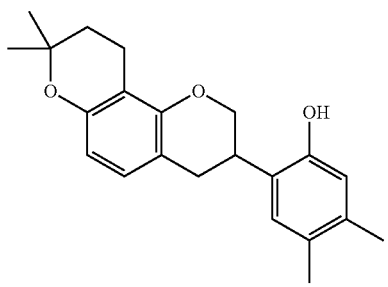
<Compound II-a-20>
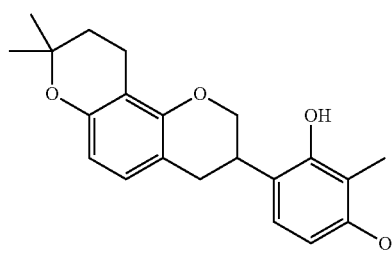
<Compound II-a-21>
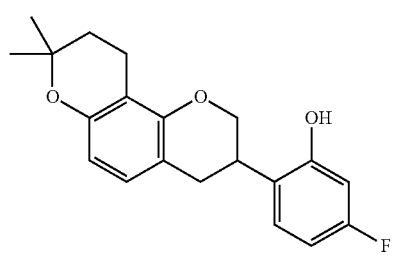
<Compound II-a-22>
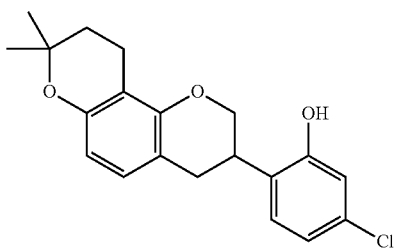
<Compound II-a-23>
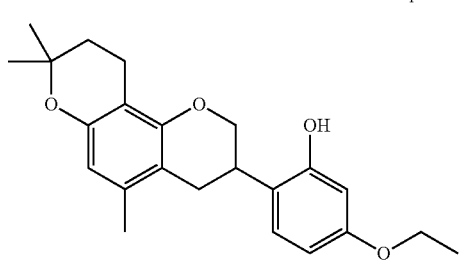
<Compound II-a-24>
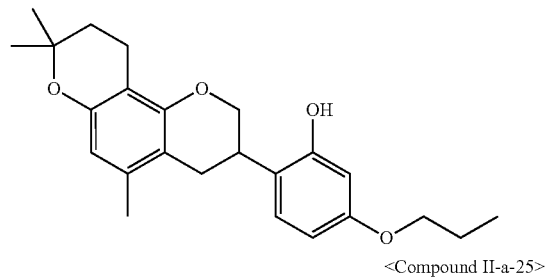
<Compound II-a-25>
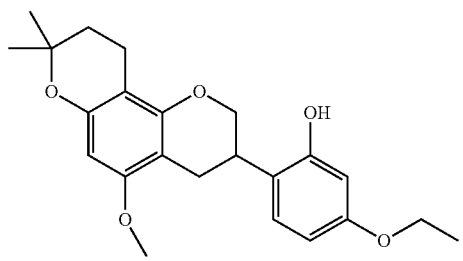
<Compound II-a-26>
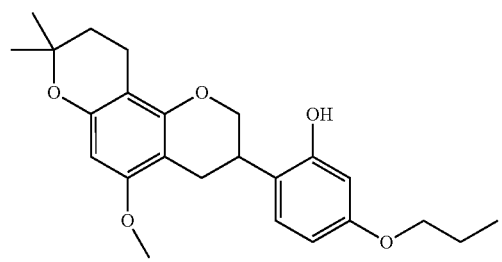
<Compound II-a-27>
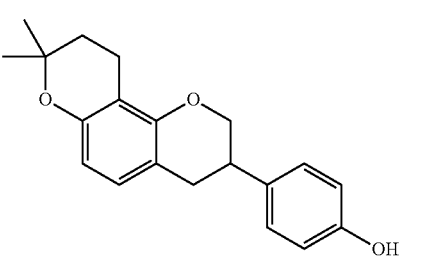
<Compound II-a-28>
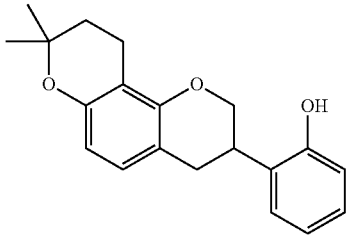
<Compound II-a-29>
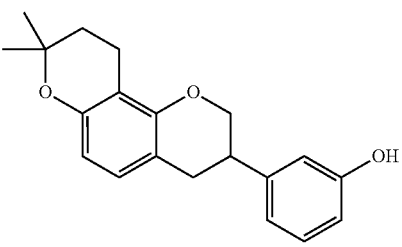

<Compound II-a-30>
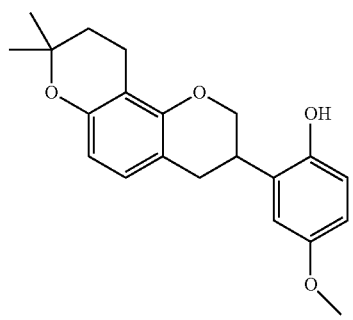
<Compound II-a-31>
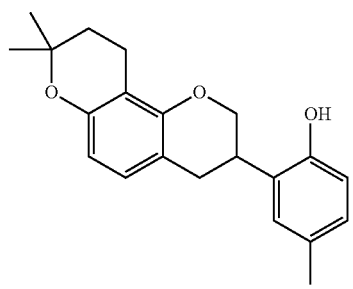
<Compound II-a-32>
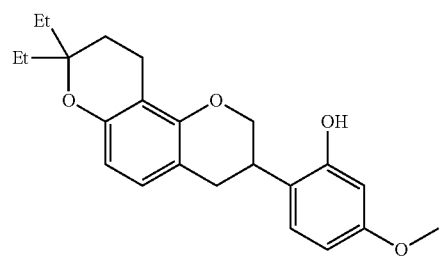
<Compound II-a-33>
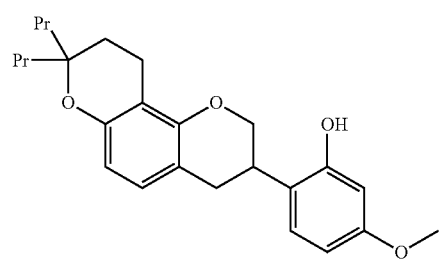
<Compound II-a-34>
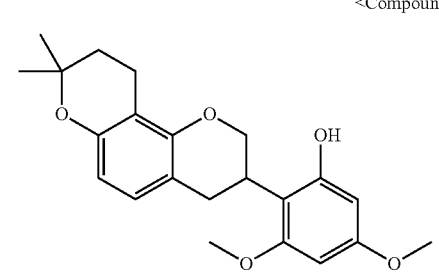
<Compound II-a-35>
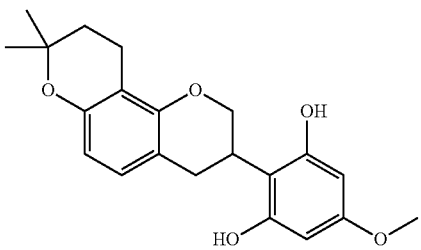
<Compound II-a-36>
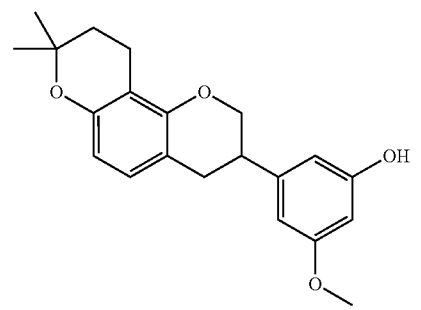
<Compound II-a-37>
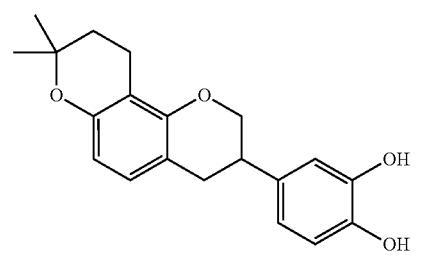
<Compound II-a-38>
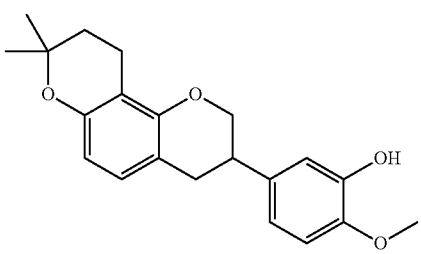
<Compound II-a-39>
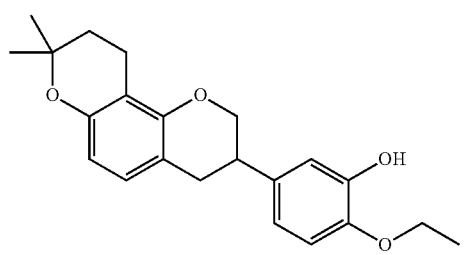

<Compound II-a-40>
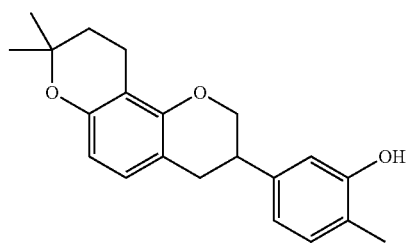
<Compound II-a-41>
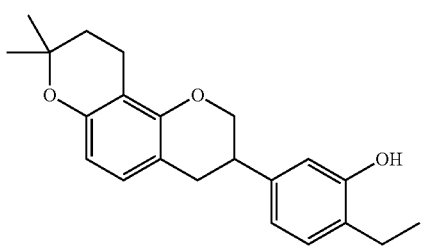
<Compound II-a-42>
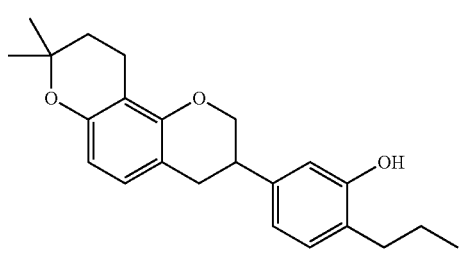
<Compound II-a-43>
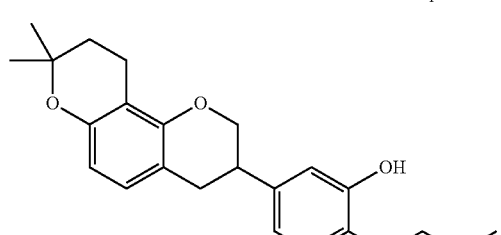
<Compound II-a-44>
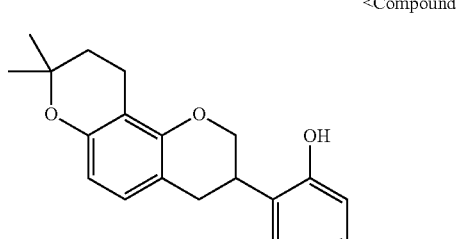
<Compound II-a-45>
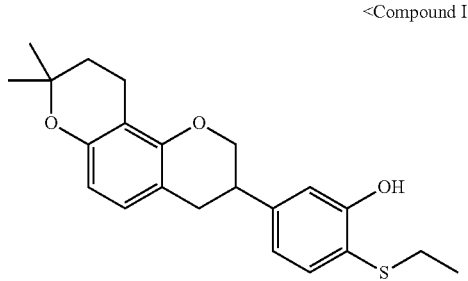
<Compound II-a-46>
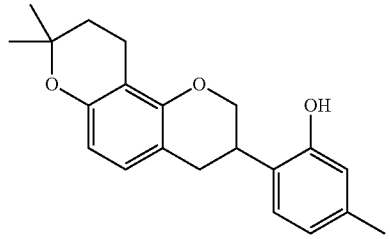
<Compound II-a-47>
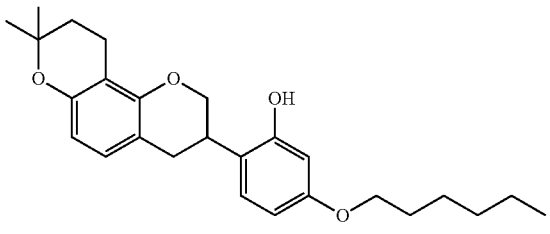
<Compound II-a-48>
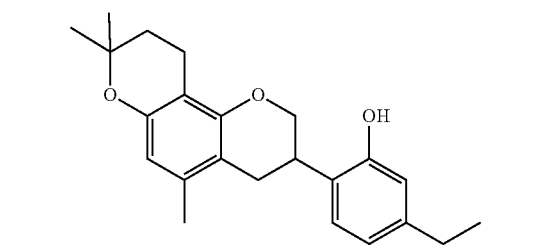
<Compound II-a-49>
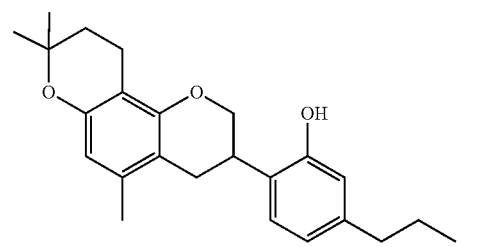
<Compound II-a-50>
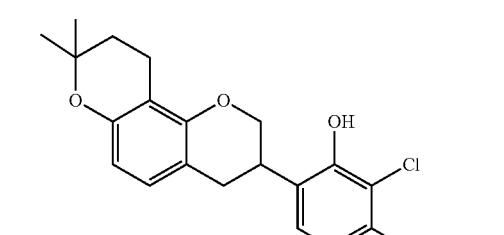
<Compound II-a-51>
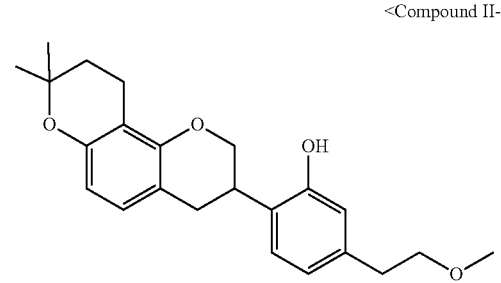

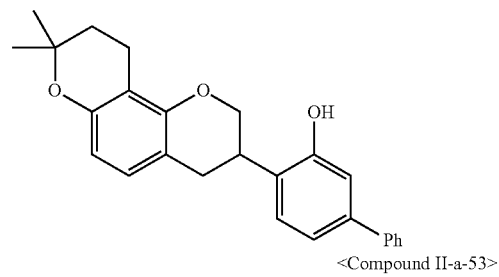
<Compound II-a-52>

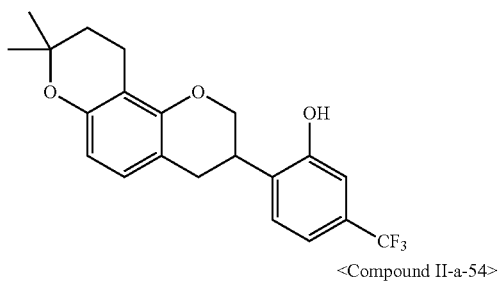
<Compound II-a-53>

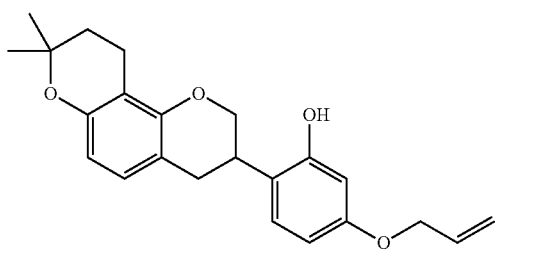
<Compound II-a-54>

According to an exemplary embodiment of the present invention, the compound of Formula (II-b) may correspond to the respective Compounds II-a-1 to II-a-54, but be one or more of Compounds II-b-1 to II-b-54, which have a fundamental skeleton of Formula (II-b).

For example, the compound of Formula (II-b) may include the following compounds.

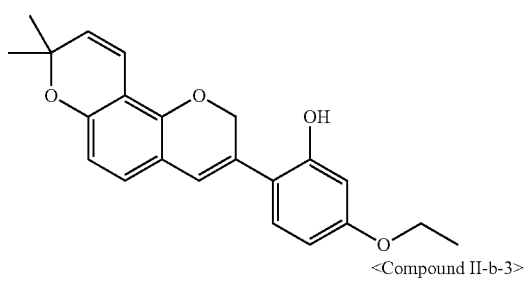
<Compound II-b-2>

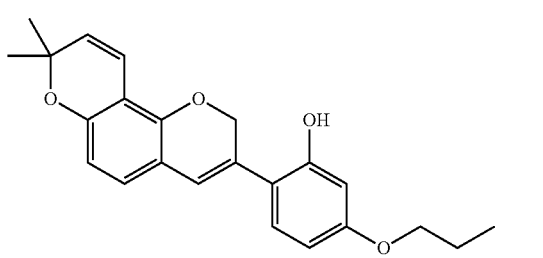
<Compound II-b-3>

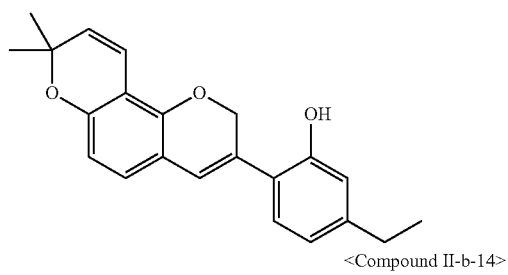
<Compound II-b-13>

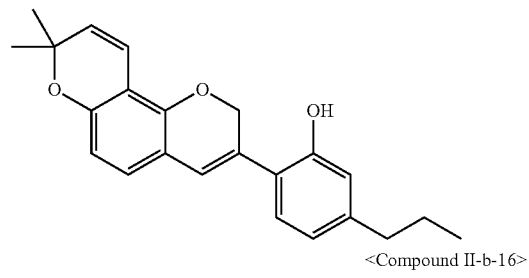
<Compound II-b-14>

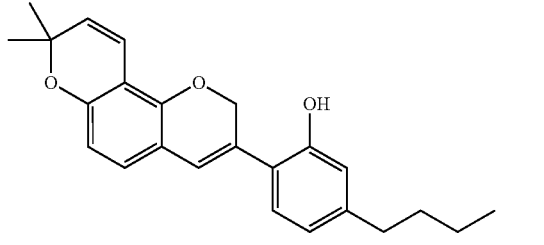
<Compound II-b-16>

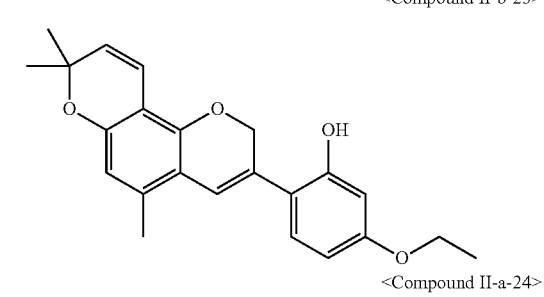
<Compound II-b-23>

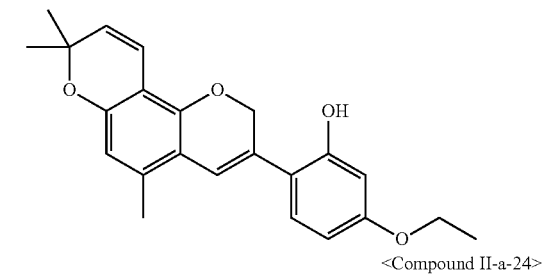
<Compound II-a-24>

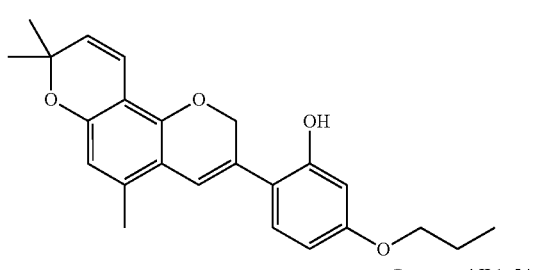
<Compound II-b-54>

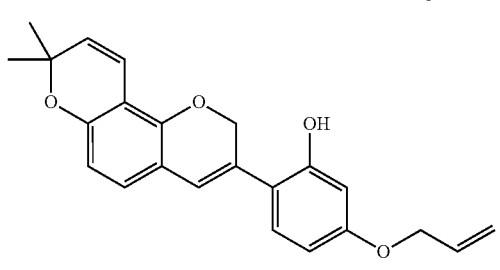

According to an exemplary embodiment of the present invention, the compound of Formula (II-c) may correspond to the respective Compounds II-a-1 to II-a-54, but be one or more of Compounds II-c-1 to II-c-54, which have a fundamental skeleton of Formula (II-c).

For example, the compound of Formula (II-c) may include the following compounds.

<Compound II-c-1>

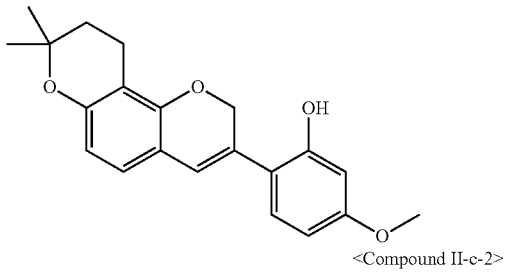

<Compound II-c-2>

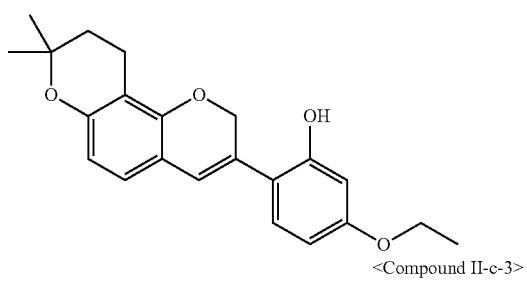

<Compound II-c-3>

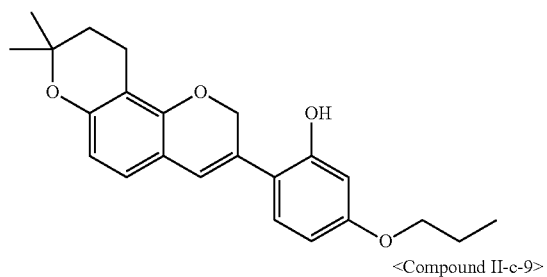

<Compound II-c-9>

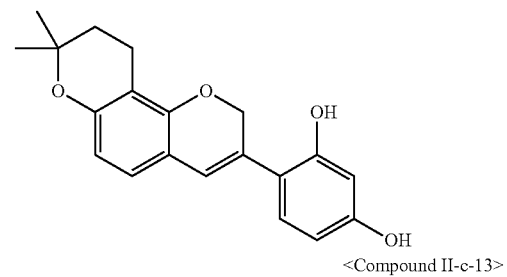

<Compound II-c-13>

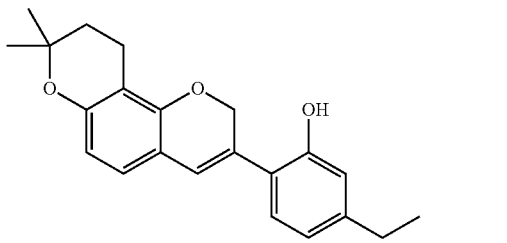

According to an exemplary embodiment of the present invention, when a benzyl group or an analogue thereof is used as a protecting group of the compound of Formula (I), the reduction procedure of the double bond and the procedure of the deprotecting group may be simultaneously performed through a hydrogen addition reaction using palladium on carbon (Pd/C) as a catalyst. If necessary, a pyranochromenyl phenol derivative in a state of having a protecting group may be synthesized, and the protecting group may be removed at an arbitrary time.

Furthermore, an exemplary embodiment of the present invention provides a compound represented by the following Formula 4, a salt or solvate thereof:

[Formula 4]

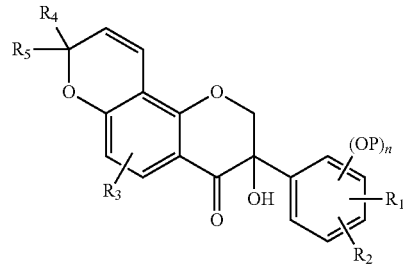

Further, an exemplary embodiment of the present invention provides a compound represented by the following Formula 4-b, a salt or solvate thereof:

[Formula 4-b]

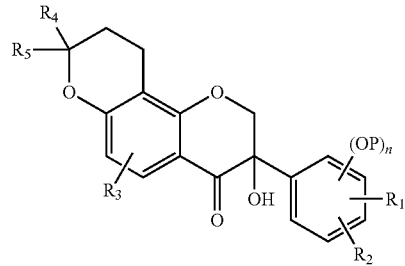

In Formulae 4 and 4-b, $R_1$ to $R_5$, P, and n are the same as those defined in Formula (I).

In addition, an exemplary embodiment of the present invention provides a compound represented by the following Formula 5, a salt or solvate thereof:

[Formula 5]

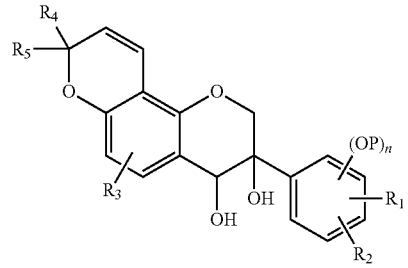

In Formula 5, the dotted line means a selective double bond, and $R_1$ to $R_5$, P, and n are the same as those defined in Formula (I).

Furthermore, the compound represented by Formula 5 may be a compound represented by the following Formula 5-a or a compound represented by the following Formula 5-b.

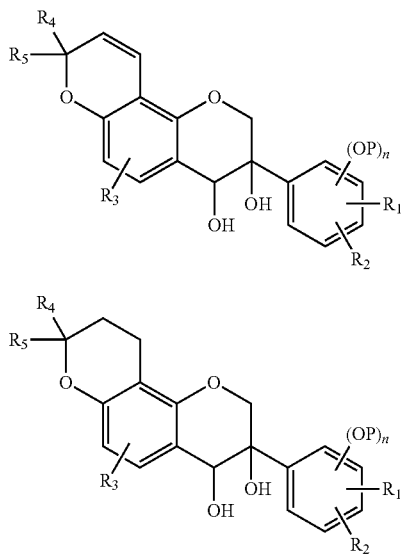

[Formula 5-a]

[Formula 5-b]

In Formulae 5-a and 5-b, $R_1$ to $R_5$, P, and n are the same as those defined in Formula (I).

The compound of Formula 4, Formula 4-b, Formula 5-a, or Formula 5-b according to the present invention may include all solvates including all salts and hydrates, which may be prepared by typical methods.

The compound of Formula 4, Formula 4-b, Formula 5-a, or Formula 5-b may be used as an intermediate in the synthesis method for preparing a compound of Formula (I).

Hereinafter, the present invention will be described in more detail by the following Examples. However, these Examples are provided merely for helping in understanding the present invention, and the scope of the present invention is not limited by these Examples in any sense.

As the reagents used in the following Examples, those purchased from Sigma-Aldrich, Inc. (USA) were used unless otherwise specifically indicated.

Example 1: Synthesis of 3-(2-(benzyloxy)-4-methoxyphenyl)-8,8-dimethyl-2,8-dihydropyrano[2,3-f]chromene (Compound I-a-1)

1-1: Preparation of 5-(2-(2-benzyloxy-4-methoxyphenyl)-2-oxoethoxy)-2,2-dimethyl-2H-chromene-6-carbaldehyde After 4.08 g (20.0 mmol) of 5-hydroxy-2,2-dimethyl-2H-chromene-6-carbaldehyde and 6.70 g (20.0 mmol) of 1-(2-(benzyloxy)-4-methoxyphenyl)-2-bromoethanone were dissolved in 20 ml of acetone ($CH_3COCH_3$), 2.76 g (20.0 mmol) of potassium carbonate ($K_2CO_3$) was added to the solution, and then the resulting mixture was vigorously stirred at room temperature for 12 hours. Thereafter, solid components were removed by filtering the reaction mixture, and the reaction solution was concentrated. The concentrate was dissolved again in 20 ml of ethyl acetate ($CH_3COOC_2H_5$), the resulting solution was washed with saturated brine, and then the organic layer was separated and dried over magnesium sulfate ($MgSO_4$). Thereafter, magnesium sulfate was removed by filtering the organic solution layer after drying the organic solution layer, and then the solution was concentrated and then recrystallized with isopropyl alcohol (IPA), thereby obtaining 7.46 g (16.3 mmol) of 5-(2-(2-(benzyloxy)-4-methoxyphenyl)-2-oxoethoxy)-2,2-dimethyl-2H-chromene-6-carbaldehyde (Yield: 81.4%).

$^1$H-NMR ($CDCl_3$): 10.152 (s, 1H), 8.066 (d, 1H, J=8.8 Hz), 7.618 (d, 1H, J=8.4 Hz), 7.280 (m, 5H), 6.629 (d, 1H, J=8.8 Hz), 6.582 (dd, 1H, J=8.8, 2.4 Hz), 6.562 (d, 1H, J=10.0 Hz), 6.500 (d, 1H, J=2.4 Hz), 5.567 (d, 1H, J=10.0 Hz), 5.084 (s, 2H), 5.070 (s, 2H), 3.846 (s, 3H), 1.406 (s, 6H).

$^{13}$C-NMR ($CDCl_3$): 192.083, 188.584, 165,281, 160.344, 159.600, 158.640, 135.146, 133.140, 130.319, 129.751, 128.704, 128.574, 127.759, 122.578, 117.958, 116.116, 114.234, 113.234, 106.271, 99.133, 82.035, 77.319, 71.020, 55.632, 28.108.

1-2: Preparation of 3-(2-(benzyloxy)-4-methoxyphenyl)-3-hydroxy-8,8-dimethyl-2,3-dihydropyrano[2,3-f]chromen-4(8M-one 36.3 mg (0.10 mmol) of 6,7-dihydro-2-pentafluorophenyl-5H-pyrrolo[2,1-c]-1,2,4-triazolium tetrafluoroborate was dissolved in 10 ml of tetrahydrofuran (THF), 21 mg (0.20 mmol) of triethylamine was added thereto, and then the resulting mixture was stirred at room temperature for 10 minutes. The solution and a solution of 7.46 g (16.3 mmol) of 5-(2-(2-benzyloxy-4-methoxyphenyl)-2-oxoethoxy)-2,2-dimethyl-2H-chromene-6-carbaldehyde obtained in Example 1-1 dissolved in 20 ml of THF were mixed, and then the resulting mixture was refluxed while being stirred for 15 hours. While being vigorously stirred, the reaction solution was cooled in an ice bath for 1 hour, a produced solid was filtered, and then the filtered solid was thoroughly washed with THF cooled to 0° C. The washed solid was dried well in vacuum, thereby obtaining 6.98 g (15.2 mmol) of 3-(2-(benzyloxy)-4-methoxyphenyl)-3-hydroxy-8,8-dimethyl-2,3-dihydropyrano[2,3-f]chromen-4(8H)-one (Yield: 93.5%).

$^1$H-NMR ($CDCl_3$): 7.660 (d, 1H, J=8.8 Hz), 7.446 (d, 1H, J=9.2 Hz), 7.262 (5H), 6.580 (d, 1H, J=10.0 Hz), 6.511 (s, 1H), 6.502 (d, 1H, J=9.2 Hz), 6.435 (d, 1H, J=8.8 Hz), 5.560 (d, 1H, J=10.0 Hz), 4.994 (s, 2H), 4.916 (d, 1H, J=11.8 Hz), 4.288 (d, 1H, J=11.8 Hz), 3.762 (s, 3H), 3.542 (b, 1H), 1.443 (s, 3H), 1.437 (s, 3H).

$^{13}$C-NMR ($CDCl_3$): 190.923, 161.056, 159,374, 157.106, 156.838, 136.028, 128.839, 128.624, 128.595, 128.439, 127.875, 127.344, 119.555, 115.782, 113.600, 111.430, 109.132, 104.829, 100.607, 77.493, 74.190, 73.969, 70.631, 55.348, 28.233, 28.193.

1-3: Preparation of 3-(2-(benzyloxy)-4-methoxyphenyl)-8,8-dimethyl-2,8-dihydropyrano[2,3-f]chromene 6.98 g (15.2 mmol) of the 3-(2-(benzyloxy)-4-methoxyphenyl)-3-hydroxy-8,8-dimethyl-2,3-dihydropyrano[2,3-f]chromen-4(8H)-one obtained in Example 1-2 was dissolved in 15 ml of THF, 17 ml (1.0 M) of a lithium borohydride ($LiBH_4$)-THF solution was added thereto, and then the resulting mixture was refluxed while being vigorously stirred for 1 hour. The reaction solution was cooled to room temperature, the reaction was terminated by adding 10 ml of concentrated brine thereto, and then the organic layer was separated. The aqueous layer was extracted once again by using 15 ml of THF, and then mixed with the organic mixture, and the resulting mixture was thoroughly dried over a sufficient amount of magnesium sulfate. The clear solution from which magnesium sulfate had been removed was distilled and concentrated to a volume of 15 ml under reduced pressure.

5.0 g (76 mmol) of powdered zinc (Zn, powder) and 20 ml of THF were charged into a separate reaction vessel and vigorously stirred, and the reaction mixture was refluxed for 1 hour by slowly adding 7.20 g (38 mmol) of titanium tetrachloride (TiCl$_4$) thereto at room temperature for 1 hour while stirring the resulting mixture, and then cooled to room temperature.

The THF solution concentrated to an amount of 15 ml was slowly added to a low valent titanium reaction mixture {Ti(O)}, which was prepared by the method, at room temperature for 30 minutes, and then the resulting mixture was vigorously stirred for 5 hours. Thereafter, the reaction was terminated by slowly adding 50 ml of water to the reaction solution, and then 100 ml of the organic layer was extracted three times by using methylene chloride (CH$_2$Cl$_2$). After the extracted organic layers were combined and then dried over a sufficient amount of magnesium sulfate, the clear solution from which magnesium chloride had been removed was distilled and concentrated under reduced pressure. 20 ml of ethanol was added to the concentrate, and the resulting mixture was refluxed for 1 hour while being vigorously stirred, and then stirred at room temperature for 1 hour. The produced solid was filtered, and the filtered solid was washed by using ethanol at 0° C. and then thoroughly dried in vacuum, thereby obtaining 3.45 g (8.1 mmol) of 3-(2-(benzyloxy)-4-methoxyphenyl)-8,8-dimethyl-2,8-dihydropyrano[2,3-f]chromene (Yield: 53.3%).

$^1$H-NMR (CDCl$_3$): 7.25-7.43 (m, 5H), 7.248 (d, 2H, J=8.8 Hz), 6.807 (d, 1H, J=8.0 Hz), 6.625 (d, 1H, J=10.0 Hz), 6.521 (s, 1H), 6.520 (d, 1H, J=2.4 Hz), 6.512 (dd, 1H, J=8.8, 2.4 Hz), 6.364 (d, 1H, J=8.0 Hz), 5.573 (d, 1H, J=10.0 Hz), 5.043 (s, 2H), 4.991 (s, 2H), 3.789 (s, 3H), 1.415 (s, 6H).

$^{13}$C-NMR (CDCl$_3$): 160.484, 157.297, 153.356, 149.196, 136.496, 129.335, 129.254, 128.603, 128.559, 127.994, 127.410, 126.520, 121.591, 121.314, 116.947, 116.641, 109.521, 109.211, 105.064, 99.963, 76.038, 70.414, 68.490, 55.402, 27.826.

Example 2: Synthesis of 3-(2-(benzyloxy)-4-ethoxyphenyl)-8,8-dimethyl-2,8-dihydropyrano[2,3-f]chromene (Compound I-a-2)

2-1: Preparation of 5-(2-(2-(benzyloxy)-4-ethoxyphenyl)-2-oxoethoxy)-2,2-dimethyl-2H-chromene-6-carbaldehyde 50 g (0.245 mol) of 5-hydroxy-2,2-dimethyl-2H-chromene-6-carbaldehyde and 89 g of (0.265 mol) of 1-(2-(benzyloxy)-4-ethoxyphenyl)-2-bromoethanone were used, thereby obtaining 97.41 g (0.206 mol) of 5-(2-(2-(benzyloxy)-4-ethoxyphenyl)-2-oxoethoxy)-2,2-dimethyl-2H-chromene-6-carbaldehyde in the same manner as in Example 1-1 (Yield 84.1%).

$^1$H-NMR (CDCl$_3$): 10.151 (s, 1H), 8.053 (d, 1H, J=8.8 Hz), 7.617 (d, 1H, J=8.8 Hz), 7.30 (m, 5H), 6.627 (d, 1H, J=8.8 Hz), 6.585 (dd, 1H, J=8.8, 2.4 Hz), 6.562 (d, 1H, J=10.0 Hz), 6.495 (d, 1H, J=2.4 Hz), 6.556 (d, 1H, J=10.0 Hz), 5.566 (d, 1H, J=10.0 Hz), 5.082 (s, 2H), 5.062 (s, 2H), 4.077 (q, 2H, J=7.2 Hz), 1.421 (t, 3H, J=7.2 Hz), 1.404 (s, 6H).

$^{13}$C-NMR (CDCl$_3$): 192.036, 188.581, 164,708, 160.366, 159.592, 158.671, 135.191, 133.108, 130.304, 129.706, 128.690, 128.550, 127.742, 122.585, 117.759, 116.122, 114.235, 113.226, 106.728, 99.482, 82.060, 77.320, 70.986, 63.973, 28.105, 14.578.

2-2: Preparation of 3-(2-(benzyloxy)-4-ethoxyphenyl)-3-hydroxy-8,8-dimethyl-2,3-dihydropyrano[2,3-f]chromen-4(8M-one 6,7-dihydro-2-pentafluorophenyl-5H-pyrrolo[2,1-c]-1,2,4-triazolium tetrafluoroborate and 100 g (0.212 mol) of the 5-(2-(2-(benzyloxy)-4-ethoxyphenyl)-2-oxoethoxy)-2,2-dimethyl-2H-chromene-6-carbaldehyde obtained in Example 2-1 were used in the same manner as in Example 1-2, thereby obtaining 93 g (0.197 mol) of 3-(2-(benzyloxy)-4-ethoxyphenyl)-3-hydroxy-8,8-dimethyl-2,3-dihydropyrano[2,3-f]chromen-4(8H)-one (Yield 93%).

$^1$H-NMR (CDCl$_3$): 7.661 (d, 1H, J=8.8 Hz), 7.424 (d, 1H, J=8.4 Hz), 7.26 (5H), 6.580 (d, 1H, J=10.0 Hz), 6.511 (d, 1H, J=2.0 Hz), 6.488 (d, 1H, J=8.4, 2.0 Hz), 6.435 (d, 1H, J=8.8 Hz), 5.558 (d, 1H, J=10.0 Hz), 4.993 (s, 2H), 4.919 (d, 1H, J=11.6 Hz), 4.288 (d, 1H, J=11.6 Hz), 3.988 (q, 2H, J=6.8 Hz), 3.526 (s, 1H), 1.443 (s, 3H), 1.437 (s, 3H), 1.379 (t, 3H, J=6.8 Hz).

$^{13}$C-NMR (CDCl$_3$): 190.971, 160.440, 159,368, 157.109, 156.863, 136.061, 128.829, 128.638, 128.553, 128.443, 127.868, 127.333, 119.317, 115.792, 113.609, 111.432, 109.142, 105.393, 100.982, 77.496, 74.200, 73.954, 70.597, 63.534, 28.229, 28.192, 14.751.

2-3: Preparation of 3-(2-(benzyloxy)-4-ethoxyphenyl)-8,8-dimethyl-2,8-dihydropyrano[2,3-f]chromene 15.66 g (0.033 mol) of the 3-(2-(benzyloxy)-4-ethoxyphenyl)-3-hydroxy-8,8-dimethyl-2,3-dihydropyrano[2,3-f]chromen-4(8H)-one obtained in Example 2-2 was used in the same manner as in Example 1-3, thereby obtaining 9.05 g (0.020 mol) of 3-(2-(benzyloxy)-4-ethoxyphenyl)-8,8-dimethyl-2,8-dihydropyrano[2,3-f]chromene (Yield 62%).

$^1$H-NMR (CDCl$_3$): 7.25-7.43 (m, 5H), 7.236 (d, 1H, J=8.8 Hz), 6.807 (d, 1H, J=8.0 Hz), 6.625 (d, 1H, J=10.0 Hz), 6.48-6.55 (m, 3H), 6.363 (d, 1H, J=8.0 Hz), 5.575 (d, 1H, J=10.0 Hz), 5.045 (s, 2H), 4.990 (s, 2H), 4.023 (q, 2H, J=6.8 Hz), 1.417 (s, 6H), 1.408 (t, 3H, J=6.8 Hz).

$^{13}$C-NMR (CDCl$_3$): 159.850, 157.304, 153.334, 149.196, 136.543, 129.306, 129.250, 128.615, 128.602, 127.980, 127.406, 126.503, 121.516, 121.140, 116.980, 116.655, 109.523, 109.199, 105.670, 100.370, 76.037, 70.391, 68.508, 63.596, 27.829, 14.790.

Examples 3 to 63

The 3-phenyl-2,8-dihydropyrano[2,3-f]chromene derivative of Formula (I-a) was synthesized in the same manner as in Example 1, except that in Example 1-1, a compound shown in the following Table 1 was used instead of 5-hydroxy-2,2-dimethyl-2H-chromene-6-carbaldehyde as the compound represented by Formula 1, and a compound shown in the following Table 1 was used instead of 1-(2-(benzyloxy)-4-methoxyphenyl)-2-bromoethanone as the compound represented by Formula 2.

TABLE 1

| No. | Compound represented by Formula 1 | Compound represented by Formula 2 |
|---|---|---|
| Example 1 | 5-hydroxy-2,2-dimethyl-2H-chromene-6-carbaldehyde | 1-(2-(benzyloxy)-4-methoxyphenyl)-2-bromoethanone |
| Example 2 | 5-hydroxy-2,2-dimethyl-2H-chromene-6-carbaldehyde | 1-(2-(benzyloxy)-4-ethoxypheny)-2-bromoethanone |
| Example 3 | 5-hydroxy-2,2-dimethyl1-2H-chromene-6-carbaldehyde | 1-(2-(benzyloxy)-4-propoxypheny1)-2-bromoethanone |
| Example 4 | 5-hydroxy-2,2-dimethyl1-2H-chromene-6-carbaldehyde | 1-(2-(allyloxy)-4-propoxypheny1)-2-bromoethanone |
| Example 5 | 5-hydroxy-2,2-dimethyl1-2H-chromene-6-carbaldehyde | 1-(2-(benzyloxy)-4-isopropoxypheny1)-2-bromoethanone |
| Example 6 | 5-hydroxy-2,2-dimethyl1-2H-chromene-6-carbaldehyde | 1-(2-(benzyloxy)-4-butoxypheny1)-2-bromoethanone |
| Example 7 | 5-hydroxy-2,2-dimethyl1-2H-chromene-6-carbaldehyde | 1-(2-(benzyloxy)-4-pentatoxypheny1)-2-bromoethanone |
| Example 8 | 5-hydroxy-2,2-dimethyl1-2H-chromene-6-carbaldehyde | 1-(2-(benzyloxy)-4-hexatoxypheny1)-2-bromoethanone |
| Example 9 | 5-hydroxy-2,2-dimethyl-2H-chromene-6-carbaldehyde | 1-(2-(benzyloxy)-4-isopentatoxypheny1)-2-bromoethanone |
| Example 10 | 5-hydroxy-2,2-dimethyl1-2H-chromene-6-carbaldehyde | 1-(2-(benzyloxy)-4-(2-methoxyethoxy)pheny1-2-bromoethanone |
| Example 11 | 5-hydroxy-2,2-dimethyl1-2H-chromene-6-carbaldehyde | 1-(2-benzyloxy-4-benzyloxypheny1)-2-bromoethanone |
| Example 12 | 5-hydroxy-2,2-dimethyl1-2H-chromene-6-carbaldehyde | 1-(4-(benzyloxy)-2-methoxypheny1)-2-bromoethanone |
| Example 13 | 5-hydroxy-2,2-dimethyl1-2H-chromene-6-carbaldehyde | 1-(4-(benzyloxy)-4-ethoxypheny1)-2-bromoethanone |
| Example 14 | 5-hydroxy-2,2-dimethyl1-2H-chromene-6-carbaldehyde | 1-(4-(benzyloxy)-2-propoxypheny1)-2-bromoethanone |
| Example 15 | 5-hydroxy-2,2-dimethyl1-2H-chromene-6-carbaldehyde | 1-(4-(benzyloxy)-2-isopropoxypheny1)-2-bromoethanone |
| Example 16 | 5-hydroxy-2,2-dimethyl1-2H-chromene-6-carbaldehyde | 1-(4-(benzyloxy)-2-butoxypheny1)-2-bromoethanone |
| Example 17 | 5-hydroxy-2,2-dimethyl1-2H-chromene-6-carbaldehyde | 1-(4-(benzyloxy)-2-(2-methoxyethoxy)pheny1-2-bromoethanone |
| Example 18 | 5-hydroxy-2,2-dimethyl-2H-chromene-6-carbaldehyde | 1-(2-(benzyloxy)-4-ethylpheny1)-2-bromoethanone |
| Example 19 | 5-hydroxy-2,2-dimethyl1-2H-chromene-6-carbaldehyde | 2-bromo-1-(4-ethy1-2-((4-nitrobenzyl)oxy)phenyl)ethanone |
| Example 20 | 5-hydroxy-2,2-dimethyl1-2H-chromene-6-carbaldehyde | 1-(2-(benzyloxy)-4-propylpheny1)-2-bromoethanone |
| Example 21 | 5-hydroxy-2,2-dimethyl1-2H-chromene-6-carbaldehyde | 2-bromo-1-(2-((4-chlorobenzyl)oxy)-4-propylphenyl)ethanone |
| Example 22 | 5-hydroxy-2,2-dimethyl1-2H-chromene-6-carbaldehyde | 2-bromo-1-(2-((2,4-dichlorobenzyl)oxy)-4-propylphenyl)ethanone |
| Example 23 | 5-hydroxy-2,2-dimethyl1-2H-chromene-6-carbaldehyde | 2-bromo-1-(2-((4-methylbenzyl)oxy)-4-propylphenyl)ethanone |
| Example 24 | 5-hydroxy-2,2-dimethyl-2H-chromene-6-carbaldehyde | 2-bromo-1-(2-((4-nitrobenzyl)oxy)-4-propylphenyl)ethanone |
| Example 25 | 5-hydroxy-2,2-dimethyl-2H-chromene-6-carbaldehyde | 2-bromo-1-(2-((2-nitrobenzyl)oxy)-4-propylphenyl)ethanone |
| Example 26 | 5-hydroxy-2,2-dimethyl-2H-chromene-6-carbaldehyde | 1-(2-(benzyloxy)-4-(isopropylphenyl)-2-bromoethanone |
| Example 27 | 5-hydroxy-2,2-dimethyl1-2H-chromene-6-carbaldehyde | 1-(2-(benzyloxy)-4-(butylpheny1)-2-bromoethanone |
| Example 28 | 5-hydroxy-2,2-dimethyl1-2H-chromene-6-carbaldehyde | 1-(2-(benzyloxy)-4-(pentylpheny1)-2-bromoethanone |
| Example 29 | 5-hydroxy-2,2-dimethyl1-2H-chromene-6-carbaldehyde | 1-(2-(benzyloxy)-4-(2-methoxyethyl)pheny1)-2-bromoethanone |
| Example 30 | 5-hydroxy-2,2-dimethyl1-2H-chromene-6-carbaldehyde | 1-(2-(benzyloxy)-3,4-dimethylpheny1)-2-bromoethanone |
| Example 31 | 5-hydroxy-2,2-dimethyl-2H-chromene-6-carbaldehyde | 1-(2-(benzyloxy)-4,5-dimethylpheny1)-2-bromoethanone |
| Example 32 | 5-hydroxy-2,2-dimethyl-2H-chromene-6-carbaldehyde | 1-(3-(benzyloxy)-[1,1'-biphenyl]-4-yl)-2-bromoethanone |
| Example 33 | 5-hydroxy-2,2-dimethyl-2H-chromene-6-carbaldehyde | 1-(2-(benzyloxy)-4-phenoxypheny1)-2-bromoethanone |
| Example 34 | 5-hydroxy-2,2-dimethyl-2H-chromene-6-carbaldehyde | 1-(2,4-bis(benzyloxy)-3-methylpheny1)-2-bromoethanone |
| Example 35 | 5-hydroxy-2,2-dimethyl-2H-chromene-6-carbaldehyde | 1-(2-(benzyloxy)-4-fluorophenyl)-2-bromoethanone |
| Example 36 | 5-hydroxy-2,2-dimethyl-2H-chromene-6-carbaldehyde | 1-(2-(benzyloxy)-4-chlorophenyl)-2-bromoethanone |
| Example 37 | 5-hydroxy-2,2-dimethyl1-2H-chromene-6-carbaldehyde | 2-(2-bromoacety1)-5-methoxypheny1-4-methylbenzenesulfonate |
| Example 38 | 5-hydroxy-2,2-dimethyl1-2H-chromene-6-carbaldehyde | 2-(2-bromoacety1)-5-ethylpheny1-4-methylbenzenesulfonate |
| Example 39 | 5-hydroxy-2,2-dimethyl1-2H-chromene-6-carbaldehyde | 2-(2-bromoacety1)-5-propylpheny1-4-methylbenzenesulfonate |
| Example 40 | 5-hydroxy-2,2-dimethyl1-2H-chromene-6-carbaldehyde | 2-(2-bromoacety1)-5-ethoxypheny1-4-methylbenzenesulfonate |
| Example 41 | 5-hydroxy-2,2-dimethyl1-2H-chromene-6-carbaldehyde | 2-(2-bromoacety1)-5-propoxypheny1-4-methylbenzenesulfonate |
| Example 42 | 5-hydroxy-2,2-dimethyl1-2H-chromene-6-carbaldehyde | 2-(2-bromoacety1)-5-propoxyphenyl 2,4,6-trimethylbenzenesulfonate |
| Example 43 | 5-hydroxy-2,2-dimethyl1-2H-chromene-6-carbaldehyde | 3-(allyloxy)-4-(2-bromoacetyl)phenyl 2,4,6-trimethylbenzenesulfonate |
| Example 44 | 5-hydroxy-2,2-dimethyl1-2H-chromene-6-carbaldehyde | 5-(allyloxy)-2-(2-bromoacetyl)phenyl 4-trimethylbenzenesulfonate |
| Example 45 | 5-hydroxy-2,2-dimethyl1-2H-chromene-6-carbaldehyde | 5-(allyloxy)-2-(2-bromoacetyl)phenyl 2,4,6-trimethylbenzenesulfonate |
| Example 46 | 5-hydroxy-2,2-dimethyl1-2H-chromene-6-carbaldehyde | 2-(2-bromoacety1)-5-butoxypheny1-4-methylbenzenesulfonate |
| Example 47 | 5-hydroxy-2,2,7-trimethyl-2H-chromene-6-carbaldehyde | 1-(2-(benzyloxy)-4-ethoxypheny1)-2-bromoethanone |
| Example 48 | 5-hydroxy-2,2,7-trimethyl-2H-chromene-6-carbaldehyde | 1-(2-(benzyloxy)-4-propoxypheny1)-2-bromoethanone |
| Example 49 | 5-hydroxy-7-methoxy-2,2-dimethyl-2H-chromene-6-carbaldehyde | 1-(2-(benzyloxy)-4-ethoxypheny1)-2-bromoethanone |
| Example 50 | 5-hydroxy-7-methoxy-2,2-dimethyl-2H-chromene-6-carbaldehyde | 1-(2-(benzyloxy)-4-propoxypheny1)-2-bromoethanone |

TABLE 1-continued

| No. | Compound represented by Formula 1 | Compound represented by Formula 2 |
|---|---|---|
| Example 51 | 5-hydroxy-2,2,7-trimethyl-2H-chromene-6-carbaldehyde | 1-(2-(benzyloxy)-4-ethylphenyl)-2-bromoethanone |
| Example 52 | 5-hydroxy-2,2,7-trimethyl-2H-chromene-6-carbaldehyde | 2-bromo-1-(2-((4-methylbenzyl)oxy)-4-propylphenyl)ethanone |
| Example 53 | 5-hydroxy-2,2-dimethyl-2H-chromene-6-carbaldehyde | 1-(2-(allyloxy)-4-ethylphenyl)-2-bromoethanone |
| Example 54 | 5-hydroxy-2,2-dimethyl-2H-chromene-6-carbaldehyde | 1-(2-(allyloxy)-4-propylphenyl)-2-bromoethanone |
| Example 55 | 5-hydroxy-2,2-dimethyl-2H-chromene-6-carbaldehyde | 1-(2-(allyloxy)-4-butylphenyl)-2-bromoethanone |
| Example 56 | 5-hydroxy-2,2-dimethyl-2H-chromene-6-carbaldehyde | 1-(2-(benzyloxy)-4-(trifluoromethyl)phenyl)-2-bromoethanone |
| Example 57 | 5-hydroxy-2,2-dimethyl-2H-chromene-6-carbaldehyde | 1-(3-(benzyloxy)-4-ethoxyphenyl)-2-bromoethanone |
| Example 58 | 5-hydroxy-2,2-dimethyl-2H-chromene-6-carbaldehyde | 1-(3-(benzyloxy)-4-ethylphenyl)-2-bromoethanone |
| Example 59 | 5-hydroxy-2,2-dimethyl-2H-chromene-6-carbaldehyde | 1-(2,4-bis(allyloxy)-3-chlorophenyl)-2-bromoethanone |
| Example 60 | 5-hydroxy-2,2-dimethyl-2H-chromene-6-carbaldehyde | 1-(2,4-bis(allyloxy)-3-methylphenyl)-2-bromoethanone |
| Example 61 | 5-hydroxy-2,2,7-trimethyl-2H-chromene-6-carbaldehyde | 1-(2,4-bis(allyloxy))-2-bromoethanone |
| Example 62 | 5-hydroxy-2,2,7-trimethyl-2H-chromene-6-carbaldehyde | 1-(2-(allyloxy)-4-ethoxyphenyl)-2-bromoethanone |
| Example 63 | 5-hydroxy-2,2,7-trimethyl-2H-chromene-6-carbaldehyde | 1-(2-(allyloxy)-4-propoxyphenyl)-2-bromoethanone |

H-NMR data and C-NMR data of the compounds prepared in Examples 1 to 63 and represented by Formula 4 are shown in the following Table 2.

TABLE 2

| No. | Chemical structure | $^1$H-NMR, $^{13}$C-NMR (CDCl$_3$, δ) |
|---|---|---|
| Example 1 | 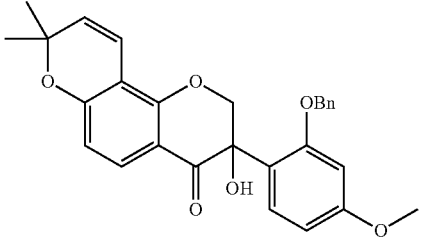 (Compound 4-1) | $^1$H-NMR (CDCl$_3$): 7.660 (d, 1H, J = 8.8 Hz), 7.446 (d, 1H, J = 9.2 Hz), 7.262 (5H), 6.580 (d, 1H, J = 10.0 Hz), 6.511 (s, 1H), 6.502 (d, 1H, J = 9.2 Hz), 6.435 (d, 1H, J = 8.8 Hz), 5.560 (d, 1H, J = 10.0 Hz), 4.994 (s, 2H), 4.916 (d, 1H, J = 11.6 Hz), 4.288 (d, 1H, J = 11.6 Hz), 3.762 (s, 3H), 3.542 (b, 1H), 1.443 (s, 3H), 1.437 (s, 3H). $^{13}$C-NMR (CDCl$_3$): 190.923, 161.056, 159.374, 157.106, 156.838, 136.028, 128.839, 128.624, 128.595, 128.439, 127.875, 127.344, 119.555, 115.782, 113.600, 111.430, 109.132, 104.829, 100.607, 77.493, 74.190, 73.969, 70.631, 55.348, 28.233, 28.193. |
| Example 2 | 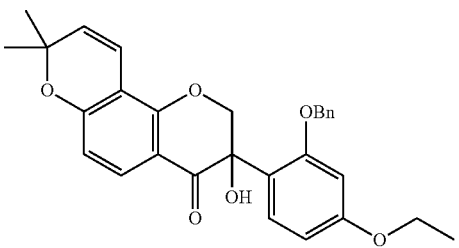 (Compound 4-2) | $^1$H-NMR (CDCl$_3$): 7.661 (d, 1H, J = 8.8 Hz), 7.424 (d, 1H, J = 8.4 Hz), 7.26 (5H), 6.580 (d, 1H, J = 10.0 Hz), 6.511 (d, 1H, J = 2.0 Hz), 6.488 (d, 1H, J = 8.4, 2.0 Hz), 6.435 (d, 1H, J = 8.8 Hz), 5.558 (d, 1H, J = 10.0 Hz), 4.993 (s, 2H), 4.919 (d, 1H, J = 11.6 Hz), 4.288 (d, 1H, J = 11.6 Hz), 3.988 (q, 2H, J = 6.8 Hz), 3.526 (s, 1H), 1.443 (s, 3H), 1.437 (s, 3H), 1.379 (t, 3H, J = 6.8 Hz). $^{13}$C-NMR (CDCl$_3$): 190.971, 160.440, 159.368, 157.109, 156.863, 136.061, 128.829, 128.638, 128.553, 128.443, 127.868, 127.333, 119.317, 115.792, 113.609, 111.432, 109.142, 105.393, 100.982, 77.496, 74.200, 73.954, 70.597, 63.534, 28.229, 28.192, 14.751. |

TABLE 2-continued

| No. | Chemical structure | $^1$H-NMR, $^{13}$C-NMR (CDCl$_3$, δ) |
|---|---|---|
| Example 3 | 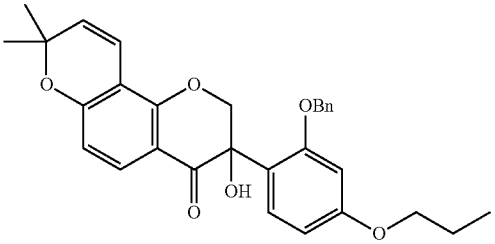<br>(Compound 4-3) | $^1$H-NMR (CDCl$_3$): 7.652 (d, 1H, J = 8.8 Hz), 7.420 (d, 1H, J = 8.4 Hz), 7.22~7.32 (m, 5H), 6.578 (d, 1H, J = 10.0 Hz), 6.519 (d, 1H, J = 2.0 Hz), 6.481 (d, 1H, J = 8.4, 2.0 Hz), 6.429 (d, 1H, J = 8.8 Hz), 5.553 (d, 1H, J = 10.0 Hz), 4.985 (s, 2H), 4.906 (d, 1H, J = 11.6 Hz), 4.279 (d, 1H, J = 11.6 Hz), 3.869 (t, 2H, J = 6.4 Hz), 3.583 (s, 1H), 1.768 (m, 2H), 1.440 (s, 3H), 1.433 (s, 3H), 1.006 (t, 3H, J = 7.6 Hz).<br>$^{13}$C-NMR (CDCl$_3$): 190.910, 160.606, 159.324, 157.094, 156.802, 136.073, 128.845, 128.568, 128.525, 128.390, 127.815, 127.337, 119.280, 115.796, 113.614, 111.368, 109.103, 105.463, 100.955, 77.450, 74.185, 73.967, 70.598, 69.548, 28.202, 28.172, 22.464, 10.473. |
| Example 4 | 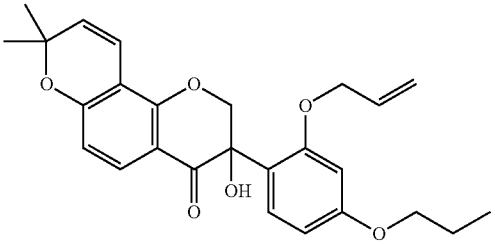<br>(Compound 4-4) | $^1$H-NMR (CDCl$_3$): 7.747 (d, 1H, J = 8.4 Hz), 7.386 (d, 1H, J = 8.4 Hz), 6.607 (d, 1H, J = 10.0 Hz), 6.499 (d, 1H, J = 8.4 Hz), 6.462 (d, 1H, J = 8.4 Hz), 6.451 (s, 1H), 5.877 (m, 1H), 5.578 (d, 1H, J = 10.0 Hz), 5.279 (d, 1H, J = 17.6 Hz), 5.167 (d, 1H, J = 10.8 Hz), 4.932 (d, 1H, J = 11.6 Hz), 4.464 (m, 2H), 4.304 (d, 1H, J = 11.6 Hz), 3.876 (t, 2H, J = 6.4 Hz), 3.672 (s, 1H), 1.778 (m, 2H), 1.447 (s, 3H), 1.440 (s, 3H), 1.012 (t, 3H, J = 7.2 Hz).<br>$^{13}$C-NMR (CDCl$_3$): 191.137, 160.580, 159.388, 157.173, 156.848, 132.574, 128.802, 128.636, 128.441, 119.383, 117.690, 115.770, 113.623, 111.395, 109.181, 105.524, 101.084, 77.509, 74.055, 73.965, 69.552, 69.490, 28.285, 28.183, 22.488, 10.475. |
| Example 9 | 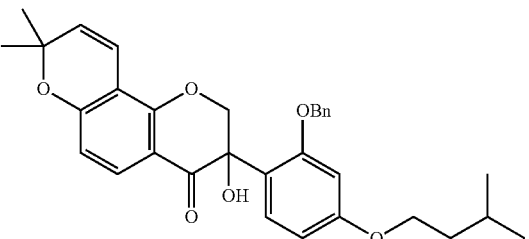<br>(Compound 4-9) | $^1$H-NMR (CDCl$_3$): 7.652 (d, 1H, J = 8.8 Hz), 7.420 (d, 1H, J = 8.4 Hz), 7.22~7.44 (5H), 6.577 (d, 1H, J = 10.0 Hz), 6.507 (d, 1H, J = 2.0 Hz), 6.481 (dd, 1H, J = 8.4, 2.0 Hz), 6.428 (d, 1H, J = 8.8 Hz), 5.551 (d, 1H, J = 10.0 Hz), 4.980 (s, 2H), 4.919 (d, 1H, J = 12.0 Hz), 4.287 (d, 1H, J = 12.0 Hz), 3.932 (t, 2H, J = 6.8 Hz), 3.588 (s, 1H), 1.801 (m, 1H), 1.633 (q, 2H, J = 6.8 Hz), 1.438 (s, 3H), 1.432 (s, 3H), 0.938 (d, 6H, J = 6.8 Hz).<br>$^{13}$C-NMR (CDCl$_3$): 190.897, 160.594, 159.318, 157.083, 156.771, 136.055, 128.842, 128.561, 128.514, 128.389, 127.815, 127.336, 119.232, 115.793, 113.601, 111.369, 109.103, 105.408, 100.926, 77.447, 74.184, 73.946, 70.576, 66.373, 37.847, 28.199, 28.165, 24.932, 22.519. |

TABLE 2-continued

| No. | Chemical structure | ¹H-NMR, ¹³C-NMR (CDCl₃, δ) |
|---|---|---|
| Example 11 | (Compound 4-11) | ¹H-NMR (CDCl₃): 7.661 (d, 1H, J = 8.8 Hz), 7.445 (d, 1H, J = 9.2 Hz), 7.22~7.43 (m, 10H), 6.53~6.59 (m, 3H), 6.420 (d, 1H, 8.0 Hz), 5.548 (d, 1H, J = 10.0 Hz), 4.993 (s, 2H), 4.959 (s, 2H), 4.901 (d, 1H, J = 11.8 Hz), 4.277 (d, 1H, J = 11.8 Hz), 3.596 (s, 1H), 1.437 (s, 3H), 1.429 (s, 3H). ¹³C-NMR (CDCl₃): 190.824, 160.221, 159.346, 157.079, 156.759, 136.607, 135.970, 128.852, 128.579, 128.399, 128.039, 127.831, 127.506, 127.298, 119.756, 115.768, 113.566, 111.398, 109.108, 105.716, 101.290, 77.466, 74.176, 73.924, 70.589, 70.092, 28.203, 28.166. |
| Example 18 | (Compound 4-18) | ¹H-NMR (CDCl₃): 7.648 (d, 1H, J = 8.8 Hz), 7.467 (d, 1H, J = 7.6 Hz), 7.22~7.45 (5H), 6.831 (dd, 1H, J = 7.6, 1.2 Hz), 6.792 (d, 1H, J = 1.2 Hz), 6.583 (d, 1H, J = 10.0 Hz), 6.424 (d, 1H, J = 8.8 Hz), 5.552 (d, 1H, J = 10.0 Hz), 5.003 (AB, 2H), 4.903 (d, 1H, J = 11.6 Hz), 4.296 (d, 1H, J = 11.6 Hz), 3.542 (s, 1H), 2.614 (q, 2H, 7.6 Hz), 1.443 (s, 3H), 1.432 (s, 3H), 1.206 (t, 3H, J = 7.6 Hz). ¹³C-NMR (CDCl₃): 190.631, 159.314, 157.053, 155.604, 146.342, 136.241, 128.893, 128.566, 128.360, 127.773, 127.680, 127.377, 124.416, 120.590, 115.816, 113.620, 112.425, 111.394, 109.120, 77.451, 74.444, 73.943, 70.583, 28.779, 28.215, 28.151, 15.285. |
| Example 24 | (Compound 4-2) | ¹H-NMR (CDCl₃): 8.102 (d, 2H, J = 8.8 Hz), 7.603 (d, 1H, J = 8.8 Hz), 7.518 (d, 1H. J = 7.6 Hz), 7.452 (d, 2H, J = 8.8 Hz), 6.870 (d, 1H, J = 7.6 Hz), 6.715 (s, 1H), 6.582 (d, 1H, J = 10.0 Hz), 6.418 (d, 1H, J = 8.8 Hz), 5.579 (d, 1H, J = 10.0 Hz), 5.116 (d, 1H, J = 12.8 Hz), 5.058 (d, 1H, J = 12.8 Hz), 4.879 (d, 1H, J = 12.0 Hz), 4.333 (d, 1H, J = 12.0 Hz), 3.445 (s, 1H), 2.550 (t, 2H, J = 7.6 Hz), 1.596 (m, 1H), 1.452 (s, 3H), 1.438 (s, 3H), 0.923 (t, 3H, J = 7.2 Hz). ¹³C-NMR (CDCl₃): 190.600, 159.641, 157.095, 154.916, 147.434, 145.028, 143.638, 128.917, 128.662, 127.806, 124.765, 123.591, 121.913, 115.557, 113.345, 113.006, 111.502, 109.187, 77.638, 74.290, 74.069, 69.448, 37.934, 28.200, 28.167, 24.292, 13.818. |

TABLE 2-continued

| No. | Chemical structure | $^1$H-NMR, $^{13}$C-NMR (CDCl$_3$, δ) |
|---|---|---|
| Example 36 | 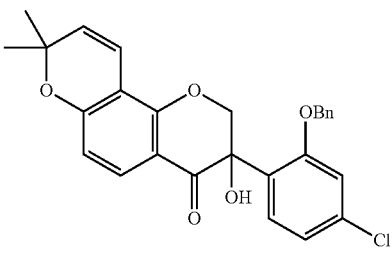<br>(Compound 4-36) | $^1$H-NMR (CDCl$_3$): 7.622 (d, 1H, J = 8.0 Hz), 7.523 (d, 1H, J = 8.4 Hz), 7.241 (s, 5H), 6.973 (dd, 1H, J = 8.0, 2.0 Hz), 6.934 (d, 1H, J = 2.0 Hz), 6.570 (d, 1H, J = 10.0 Hz), 6.430 (d, 1H, J = 8.4 Hz), 5.560 (d, 1H, J = 10.0 Hz), 4.971 (s, 1H), 4.842 (d, 1H, 12.0 Hz), 4.268 (d, 1H, J = 12.0 Hz), 3.577 (s, 1H), 1.450 (s, 3H), 1.437 (s, 3H).<br>$^{13}$C-NMR (CDCl$_3$): 190.007, 159.578, 157.000, 156.176, 135.401, 135.299, 128.914, 128.781, 128.489, 128.085, 127.439, 125.929, 121.300, 115.664, 113.338, 111.642, 109.167, 77.603, 74.293, 73.722, 71.034, 28.262, 28.197. |
| Example 43 | 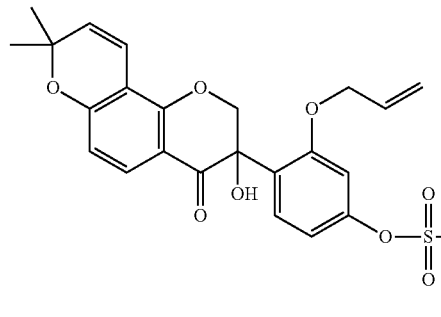<br>(Compound 4-43) | $^1$H-NMR (CDCl$_3$): 7.706 (d, 1H, J = 8.8 Hz), 7.421 (d, 1H, J = 8.8 Hz), 6.971 (s, 2H), 6.586 (d, 1H, J = 10.0 Hz), 6.555 (d, 1H, J = 2.0 Hz), 6.502 (d, 2H, J = 8.8 Hz), 5.749 (m, 1H), 5.584 (d, 1H, J = 10.0 Hz), 5.195 (dd, 1H, J = 17.2, 1.6 Hz), 5.134 (dd, 1H, J = 10.4, 1.6 Hz), 4.857 (d, 1H, J = 11.6 Hz), 4.263 (d, 1H, J = 11.6 Hz), 3.571 (s, 1H), 2.549 (s, 6H), 2.318 (s, 3H), 1.459 (s, 3H), 1.441 (s, 3H).<br>$^{13}$C-NMR (CDCl$_3$): 190.151, 159.631, 157.064, 156.242, 150.356, 143.897, 140.441, 131.800, 131.761, 130.582, 128.846, 128.787, 128.540, 126.105, 118.189, 115.572, 114.155, 113.310, 111.638, 109.214, 107.569, 77.661, 74.075, 73.679, 69.773, 28.338, 28.183, 22.678, 21.059. |
| Example 47 | 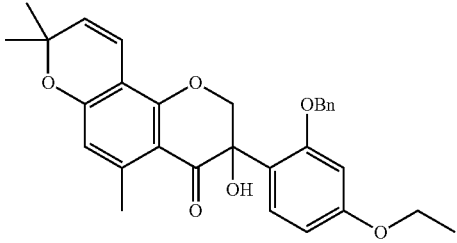<br>(Compound 4-47) | $^1$H-NMR (CDCl$_3$): 7.365 (d, 1H, J = 8.4 Hz), 7.22~7.30 (5H), 6.567 (d, 1H, J = 10.0 Hz), 6.477 (d, 1H, J = 2.4 Hz), 6.444 (dd, 1H, J = 8.4, 2.4 Hz), 6.221 (s, 1H), 5.509 (d, 1H, J = 10.0 Hz), 5.009 (AB, 2H), 4.967 (d, 1H, J = 11.6 Hz), 4.234 (d, 1H, J = 11.6 Hz), 3.959 (t, 2H, J = 7.2 Hz), 3.850 (s, 1H), 2.440 (s, 3H), 1.428 (s, 3H), 1.412 (s, 3H), 1.358 (t, 3H, J = 7.2 Hz).<br>$^{13}$C-NMR (CDCl$_3$): 193.202, 160.283, 157.922, 157.036, 143.900, 136.203, 128.621, 128.409, 127.844, 127.754, 127.031, 119.785, 115.965, 113.762, 112.438, 107.384, 105.264, 100.921, 77.316, 74.065, 73.085, 70.376, 63.472, 28.297, 28.213, 22.664, 147.722. |
| Example 48 | 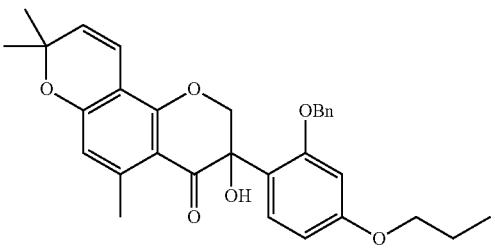<br>(Compound 4-48) | $^1$H-NMR (CDCl$_3$): 7.365 (d, 1H, J = 8.4 Hz), 7.22~7.30 (5H), 6.567 (d, 1H, J = 10.0 Hz), 6.489 (d, 1H, J = 2.4 Hz), 6.454 (dd, 1H, J = 8.4, 2.4 Hz), 6.219 (s, 1H), 5.509 (d, 1H, J = 10.0 Hz), 5.012 (AB, 2H), 4.969 (d, 1H, J = 11.6 Hz), 4.234 (d, 1H, J = 11.6 Hz), 3.852 (t, 2H, J = 6.4 Hz), 3.835 (s, 1H), 2.437 (s, 3H), 1.754 (m, 1H), 1.429 (s, 3H), 1.413 (s, 3H), 0.994 (t, 3H, J = 6.8 Hz).<br>$^{13}$C-NMR (CDCl$_3$): 193.222, 160.498, 157.904, 157.048, 143.905, 136.209, 128.606, 128.413, |

TABLE 2-continued

| No. | Chemical structure | $^1$H-NMR, $^{13}$C-NMR (CDCl$_3$, δ) |
|---|---|---|
| | | 127.847, 127.767, 127.069, 119.717, 115.978, 113.774, 112.446, 107.392, 105.318, 100.905, 77.317, 74.082, 73.085, 70.398, 69.526, 28.302, 28.220, 22.688, 22.460, 10.474. |
| Example 51 | (Compound 4-51) | $^1$H-NMR (CDCl$_3$): 7.420 (d, 1H, J = 8.0 Hz), 7.22~7.30 (5H), 6.803 (dd, 1H, J = 8.0, 1.2 Hz), 6.765 (d, 1H, J = 1.2 Hz), 6.577 (d, 1H, J = 10.0 Hz), 6.214 (s, 1H), 5.512 (d, 1H, J = 10.0 Hz), 5.027 (AB, 2H), 4.955 (d, 1H, J = 11.6 Hz), 4.255 (d, 1H, J = 11.6 Hz), 3.770 (s, 1H), 2.595 (q, 2H), 7.6 Hz), 1.436 (s, 3H), 1.412 (s, 3H), 1.190 (t, 3H, J = 7.6 Hz). |
| Example 56 | (Compound 4-56) | $^1$H-NMR (CDCl$_3$): 7.753 (d, 1H, J = 8.0 Hz), 7.612 (d, 1H, J = 8.8 Hz), 7.261 (d, 1H, J = 8.0 Hz), 7.233 (s, 5H), 7.166 (s, 1H), 6.572 (d, 1H, J = 10.0 Hz), 6.429 (d, 1H, J = 8.8 Hz), 5.572 (d, 1H, J = 10.0 Hz), 5.032 (AB, 1H, J = 11.2 Hz), 4.993 (AB, 1H, 11.2 Hz), 4.848 (d, 1H, J = 12.0 Hz), 4.279 (d, 1H, J = 12.0 Hz), 3.628 (s, 1H), 1.457 (s, 3H), 1.441 (s, 3H). $^{13}$C-NMR (CDCl$_3$): 189.497, 159.678, 156.947, 155.675, 135.164, 132.203, 131.250, 128.967, 128.866, 128.580, 128.499, 128.186, 127.595, 118.121, 115.622, 113.277, 111.771, 109.375, 109.195, 77.658, 74.552, 73.648, 71.160, 28.283, 28.199. |
| Example 57 | (Compound 4-57) | $^1$H-NMR (CDCl$_3$): 7.689 (d, 1H, J = 8.8 Hz), 7.25~7.40 (m, 5H), 7.077 (d, 1H, J = 2.4 Hz), 6.980 (dd, 1H, J = 8.4, 2.4 Hz), 6.797 (d, 1H, J = 8.4 Hz), 6.539 (d, 1H, J = 10.0 Hz), 6.489 (d, 1H, J = 8.8 Hz), 5.572 (d, 1H, J = 10.0 Hz), 5.072 (s, 2H), 4.751 (d, 1H, J = 11.6 Hz), 4.378 (d, 1H, J = 11.6 Hz), 4.159 (s, 1H), 4.049 (q, 2H, J = 6.8 Hz), 1.450 (s, 3H), 1.426 (s, 3H), 1.405 (t, 3H, J = 7.2 Hz). $^{13}$C-NMR (CDCl$_3$): 192.826, 160.225, 157.609, 149.492, 148.399, 137.089, 131.269, 128.873, 128.414, 128.372, 127.711, 127.322, 119.351, 115.360, 113.157, 112.688, 111.739, 109.148, 77.842, 74.089, 72.554, 71.290, 64.419, 28.415, 28.264, 14.801. |

TABLE 2-continued

| No. | Chemical structure | $^1$H-NMR, $^{13}$C-NMR (CDCl$_3$, δ) |
|---|---|---|
| Example 58 | 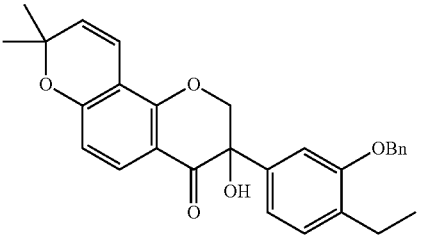<br>(Compound 4-58) | $^1$H-NMR (CDCl$_3$): 7.719 (d, 1H, J = 8.4 Hz), 7.27~7.40 (m, 5H), 7.092 (d, 1H, J = 8.0 Hz), 7.057 (d, 1H, J = 2.0 Hz), 6.978 (d, 1H, J = 8.0, 2.0 Hz), 6.559 (d, 1H, J = 10.0 Hz), 6.500 (d, 1H, J = 8.4 Hz), 5.572 (d, 1H, J = 10.0 Hz), 5.072 (s, 2H), 4.751 (d, 1H, J = 11.6 Hz), 4.378 (d, 1H, J = 11.6 Hz), 4.159 (s, 1H), 4.049 (q, 2H, J = 6.8 Hz), 1.450 (s, 3H), 1.426 (s, 3H), 1.405 (t, 3H, J = 7.2 Hz).<br>$^{13}$C-NMR (CDCl$_3$): 192.859, 160.279, 157.738, 156.562, 137.645, 137.167, 133.531, 128.984, 128.907, 128.446, 127.721, 127.162, 118.202, 115.372, 112.792, 111.784, 109.223, 109.196, 77.866, 74.242, 72.864, 69.748, 28.428, 28.262, 23.066, 13.863. |
| Example 59 | 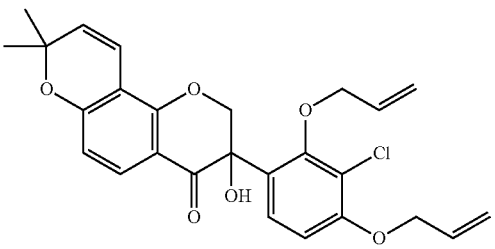<br>(Compound 4-59) | $^1$H-NMR (CDCl$_3$): 7.744 (d, 1H, J = 8.8 Hz), 7.165 (d, 1H, J = 8.4 Hz), 6.606 (d, 1H, J = 8.8 Hz), 6.539 (d, 1H, J = 10.0 Hz), 6.505 (d, 1H, J = 8.4 Hz), 6.027 (m, 2H), 5.553 (d, 1H, J = 10.0 Hz), 5.448 (dd, 1H, J = 17.2, 0.8 Hz), 5.356 (dd, 1H, J = 17.2, 0.8 Hz), 5.298 (dd, 1H, J = 10.4, 0.8 Hz), 5.194 (dd, 1H, J = 10.4, 0.8 Hz), 5.097 (d, 1H, J = 11.6 Hz), 4.680 (dd, 1H, J = 11.6, 5.6 Hz), 4.567 (d, 2H, J = 5.2 Hz), 4.428 (dd, 1H, J = 11.6, 5.6 Hz), 4.229 (d, 1H, J = 11.6 Hz), 4.052 (s, 1H), 1.436 (s, 3H), 1.431 (s, 3H).<br>$^{13}$C-NMR (CDCl$_3$): 192.126, 159.862, 157.589, 155.669, 154.610, 133.353, 132.350, 128.736, 128.631, 126.260, 125.898, 117.976, 117.700, 115.516, 113.212, 111.622, 109.150, 108.149, 77.738, 74.216, 74.038, 73.790, 69.739, 28.299. |
| Example 60 | 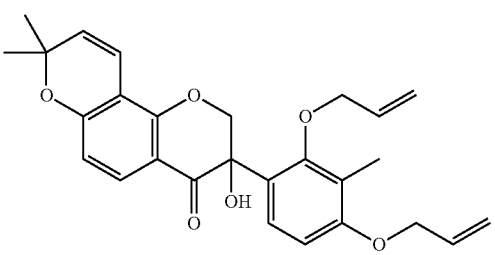<br>(Compound 4-60) | $^1$H-NMR (CDCl$_3$): 7.744 (d, 1H, J = 8.8 Hz), 7.090 (d, 1H, J = 8.4 Hz), 6.548 (d, 1H, J = 10.0 Hz), 6.532 (d, 1H, J = 8.4 Hz), 6.494 (d, 1H, J = 8.8 Hz), 5.98~6.07 (m, 2H), 5.538 (d, 1H, J = 10.0 Hz), 5.406 (dd, 1H, J = 12.8, 1.6 Hz), 5.363 (dd, 1H, J = 12.8, 1.6 Hz), 5.258 (dd, 1H, J = 10.8, 1.2 Hz), 5.196 (dd, 1H, J = 10.4, 1.2 Hz), 5.151 (d, 1H, J = 11.2 Hz), 4.493 (d, 2H, J = 5.2 Hz), 4.452 (dd, 1H, J = 12.0, 5.2 Hz), 4.247 (d, 1H, J = 11.2 Hz), 4.240 (dd, 1H, J = 12.0, 5.2 Hz), 4.065 (s, 1H), 2.149 (s, 3H), 1.434 (s, 3H), 1.419 (s, 3H).<br>$^{13}$C-NMR (CDCl$_3$): 192.945, 159.624, 158.261, 157.589, 156.700, 133.753, 133.236, 128.592, 128.577, 125.558, 124.195, 120.843, 117.116, 117.004, 115.685, 113.454, 111.430, 109.125, 106.755, 77.611, 74.309, 74.212, 73.853, 68.876, 28.301, 28.256, 9.992. |

H-NMR data and C-NMR data of the compounds prepared in Examples 1 to 63 and represented by Formula 5-a are shown in the following Table 3.

TABLE 3

| No. | Chemical structure | $^{1}$H-NMR, $^{13}$C-NMR (CDCl$_3$, δ) |
|---|---|---|
| Example 1 | 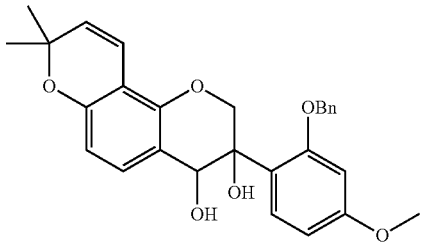<br>(Compound 5-a-1) | $^{1}$H-NMR(CDCl$_3$): 7.32~7.44 (m, 5H), 7.096(d, 1H, J = 8.4 Hz), 7.036(d, 1H, J = 8.4 Hz), 6.692(d, 1H, J = 10.0 Hz), 6.641(d, 1H, J = 2.0 Hz), 6.513(dd, 1H, J = 8.4, 2.0 Hz), 6.436(d, 1H, J = 8.4 Hz), 5.551(d, 1H, J = 10.0 Hz), 5.165(d, 1H, 11.6 Hz), 5.131(d, 1H, J = 11.6 Hz), 4.846(s, 1H), 4.648(d, 1H, J = 10.8 Hz), 4.401(d, 1H, J = 10.8 Hz), 4.334(s, 1H), 3.788(s, 3H), 1.947(s, 1H), 1.431(s, 3H), 1.410(s, 3H).<br>$^{13}$C-NMR(CDCl$_3$): 160.475, 157.687, 153.697, 149.086, 135.419, 130.332, 128.989, 128.624, 128.612, 128.157, 127.714, 120.161, 116.768, 115.127, 109.620, 109.492, 104.923, 100.815, 75.931, 71.679, 70.885, 69.744, 67.568, 55.365, 27.961, 27.704. |
| Example 2 | 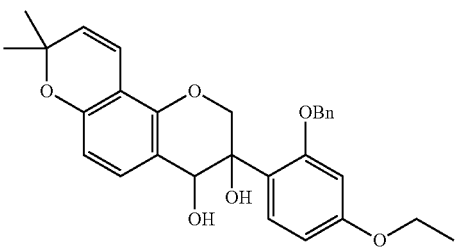<br>(Compound 5-a-2) | $^{1}$H-NMR(CDCl$_3$): 7.22~7.40(m, 5H), 7.064(d, 1H, J = 8.4 Hz), 7.016(d, 1H, J = 8.4 Hz), 6.671(d, 1H, J = 10.0 Hz), 6.628(d, 1H, J = 2.0 Hz), 6.484(d, 1H, J = 8.4, 2.0 Hz), 6.415(d, 1H, J = 8.4 Hz), 5.529(d, 1H, J = 10.0 Hz), 5.148(d, 1H, J = 11.2 Hz), 5.114(d, 1H, J = 11.2 Hz), 4.824(s, 1H), 4.632(d, 1H, J = 10.8 Hz), 4.385(d, 1H, J = 10.8 Hz), 4.310(s, 1H), 3.999(q, 2H, J = 7.2 Hz), 1.885(s, 1H), 1.411(s, 3H), 1.391(s, 3H), 1.391(t, 3H, J = 7.2 Hz).<br>$^{13}$C-NMR(CDCl$_3$): 159.851, 157.683, 153.672, 149.090, 135.449, 130.361, 128.968, 128.594, 128.575, 128.104, 127.698, 119.932, 116.778, 115.115, 109.590, 109.475, 105.516, 101.173, 75.913, 71.679, 70.848, 69.711, 67.543, 63.577, 27.954, 27.696, 14.707. |
| Example 3 | 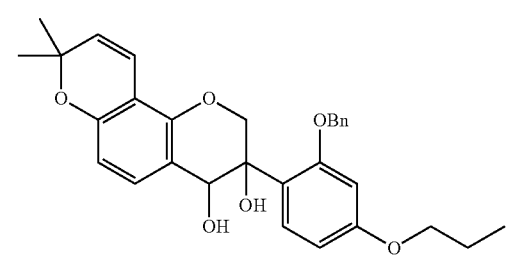<br>(Compound 5-a-3) | $^{1}$H-NMR(CDCl$_3$): 7.32~7.44(m, 5H), 7.079(d, 1H, J = 8.4 Hz), 7.032(d, 1H, J = 8.4 Hz), 6.682(d, 1H, J = 10.0 Hz), 6.655(d, 1H, J = 2.4 Hz), 6.501(d, 1H, J = 8.4, 2.4 Hz), 6.422(d, 1H, J = 8.4 Hz), 5.541(d, 1H, J = 10.0 Hz), 5.171(d, 1H, J = 11.2 Hz), 5.136(d, 1H, J = 11.2 Hz), 4.842(m, 1H), 4.651(dd, 1H, J = 10.8, 1.6 Hz), 4.403(d, 1H, J = 10.8, 1.6 Hz), 4.330(d, 1H, J = 1.6 Hz), 3.906(t, 2H, J = 6.4 Hz), 1.850(d, 1H, J = 3.2 Hz), 1.802(m, 2H), 1.422(s, 3H), 1.402(s, 3H), 1.036(t, 3H, J = 7.2 Hz).<br>$^{13}$C-NMR(CDCl$_3$): 160.066, 157.691, 153.678, 149.097, 135.443, 130.373, 128.981, 128.618, 128.582, 128.073, 127.742, 119.839, 116.784, 115.100, 109.601, 109.487, 105.584, 101.150, 75.922, 71.675, 70.874, 69.706, 69.616, 67.540, 27.958, 27.704, 22.457, 10.477. |

TABLE 3-continued

| No. | Chemical structure | $^1$H-NMR, $^{13}$C-NMR (CDCl$_3$, δ) |
|---|---|---|
| Example 4 | 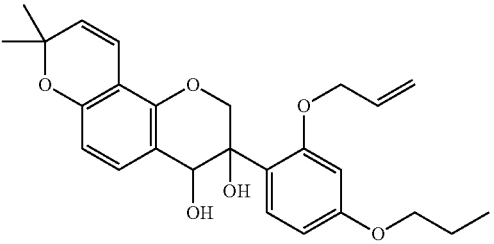<br>(Compound 5-a-4) | $^1$H-NMR(CDCl$_3$): 7.083(d, 1H, J = 8.4 Hz), 7.058(d, 1H, J = 8.4 Hz), 6.695(d, 1H, J = 10.0 Hz), 6.547(d, 1H, J = 2.0 Hz), 6.487(dd, 1H, J = 8.4, 2.0 Hz), 6.444(d, 1H, J = 8.4 Hz), 6.053(m, 1H), 5.547(d, 1H, J = 10.0 Hz), 5.421(dd, 1H, J = 17.2, 1.2 Hz), 5.333(dd, 1H, J = 10.8, 1.2 Hz), 4.871(s, 1H), 4.654(d, 1H, J = 10.8 Hz), 4.626(b, 2H), 4.403(d, 1H, J = 10.8 Hz), 4.372(s, 1H), 3.902(t, 2H, J = 6.8 Hz), 1.868(b, 1H), 1.800(m, 2H), 1.423(s, 3H), 1.407(s, 3H), 1.032(t, 3H, J = 7.2 Hz).<br>$^{13}$C-NMR(CDCl$_3$): 160.056, 157.453, 153.735, 149.163, 131.939, 130.451, 128.609, 128.002, 119.859, 119.102, 116.845, 115.133, 109.598, 109.548, 105.553, 101.042, 75.927, 71.684, 69.680, 69.618, 69.351, 67.502, 27.952, 27.669, 22.477, 10.474. |
| Example 9 | 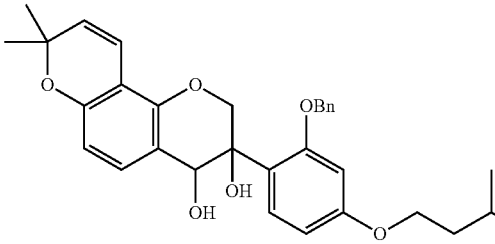<br>(Compound 5-a-9) | $^1$H-NMR(CDCl$_3$): 7.33~7.38(m, 5H), 7.072(d, 1H, J = 8.4 Hz), 7.022(d, 1H, J = 8.4 Hz), 6.672(d, 1H, J = 10.0 Hz), 6.635(d, 1H, J = 2.0 Hz), 6.501(d, 1H, J = 8.4, 2.0 Hz), 6.417(d, 1H, J = 8.4 Hz), 5.530(d, 1H, J = 10.0 Hz), 5.159(d, 1H, J = 11.2 Hz), 5.125(d, 1H, J = 11.2 Hz), 4.833(s, 1H), 4.642(d, 1H, J = 10.8 Hz), 4.392(d, 1H, J = 10.8 Hz), 4.313(s, 1H), 3.964(t, 2H, J = 6.8 Hz), 1.843(b, 1H), 1.829(m, 1H), 1.658(m, 2H), 1.412(s, 3H), 1.392(s, 3H), 0.956(d, 6H, J = 6.4 Hz).<br>$^{13}$C-NMR(CDCl$_3$): 160.082, 157.706, 153.699, 149.111, 135.465, 130.366, 128.988, 128.628, 128.592, 128.090, 127.753, 119.860, 116.795, 115.119, 109.614, 109.500, 105.605, 101.182, 75.930, 71.694, 70.897, 69.753, 67.577, 66.493, 37.847, 27.969, 27.718, 24.982, 22.526. |
| Example 11 | 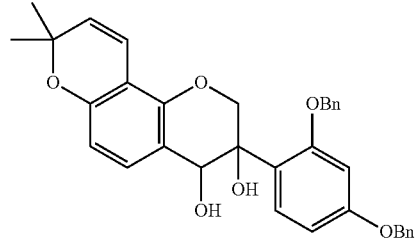<br>(Compound 5-a-11) | $^1$H-NMR(CDCl$_3$): 7.32~7.41(m, 10H), 7.085(d, 1H, J = 8.4 Hz), 7.021(d, 1H, J = 8.4 Hz), 6.713(d, 1H, J = 2.4 Hz), 6.679(d, 1H, J = 10.0 Hz), 6.575(dd, 1H, J = 8.4, 2.4 Hz), 6.419(d, 1H, J = 8.4 Hz), 5.531(d, 1H, J = 10.0 Hz), 5.137(d, 1H, 11.6 Hz), 5.004(d, 1H, J = 11.6 Hz), 5.031(s, 2H), 4.834(s, 1H), 4.640(d, 1H, J = 10.8 Hz), 4.387(d, 1H, J = 10.8 Hz), 4.296(s, 1H), 1.858(s, 1H), 1.411(s, 3H), 1.391(s, 3H).<br>$^{13}$C-NMR(CDCl$_3$): 159.685, 157.709, 153.719, 149.088, 136.513, 130.331, 128.995, 128.651, 128.176, 128.144, 127.721, 127.499, 120.426, 116.769, 115.113, 109.640, 109.506, 105.984, 101.557, 75.945, 71.694, 70.912, 70.187, 69.763, 67.571, 27.969, 27.717. |

TABLE 3-continued

| No. | Chemical structure | ¹H-NMR, ¹³C-NMR (CDCl₃, δ) |
|---|---|---|
| Example 18 | 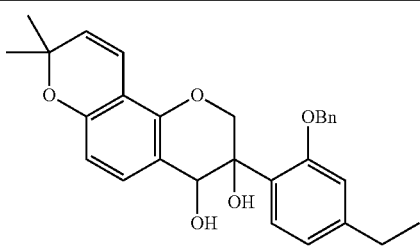<br>(Compound 5-a-18) | ¹H-NMR(CDCl₃): 7.32~7.40(m, 5H), 7.079(d, 1H, J = 8.4 Hz), 7.013(d, 1H, J = 8.4 Hz), 6.916(d, 1H, J = 1.2 Hz), 6.6840(dd, 1H, J = 8.4, 1.2 Hz), 6.677(d, 1H, J = 10.0 Hz), 6.416(d, 1H, J = 8.4 Hz), 5.530(d, 1H, J = 10.0 Hz), 5.197(d, 1H, J = 11.2 Hz), 5.162(d, 1H, J = 11.2 Hz), 4.849(s, 1H), 4.673(d, 1H, J = 10.8 Hz), 4.448(s, 1H), 4.413(d, 1H, J = 10.8 Hz), 2.638(q, 2H, J = 7.2 Hz), 1.823(s, 1H), 1.412(s, 3H), 1.391(s, 3H), 1.229(t, 3H, J = 7.2 Hz).<br>¹³C-NMR(CDCl₃): 156.634, 153.719, 149.113, 145.909, 135.645, 130.419, 128.973, 128.590, 127.775, 127.281, 125.042, 120.866, 116.801, 115.110, 109.607, 109.607, 109.517, 75.935, 71.818, 70.822, 69.657, 67.448, 28.718, 27.972, 27.712, 15.229. |
| Example 24 | 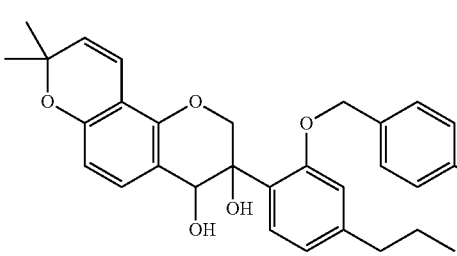<br>(Compound 5-a-24) | ¹H-NMR(CDCl₃): 8.242(d, 2H, J = 8.8 Hz), 7.594(d, 2H, J = 8.8 Hz), 7.137(d, 1H, J = 8.0 Hz), 7.021(d, 1H, J = 8.0 Hz), 6.861(dd, 1H, J = 8.0, 1.2 Hz), 6.794(d, 1H, J = 1.2 Hz), 6.678(d, 1H, J = 10.0 Hz), 6.435(d, 1H, J = 8.0 Hz), 5.554(d, 1H, J = 10.0 Hz), 5.295(s, 2H), 4.869(s, 1H), 4.697(d, 1H, J = 10.8 Hz), 4.442(d, 1H, J = 10.8 Hz), 4.076(s, 1H), 2.553(t, 2H, J = 7.2 Hz), 1.882(b, 1H), 1.606(m, 2H), 1.421(s, 3H), 1.399(s, 3H), 0.919(t, 3H, J = 7.2 Hz).<br>¹³C-NMR(CDCl₃): 156.010, 153.877, 149.017, 147.829, 144.598, 143.162, 130.422, 128.833, 127.886, 127.525, 125.225, 124.168, 122.079, 116.627, 114.924, 113.016, 109.863, 109.606, 76.025, 71.954, 69.775, 69.392, 67.480, 37.817, 27.972, 27.688, 24.207, 13.764. |
| Example 36 | 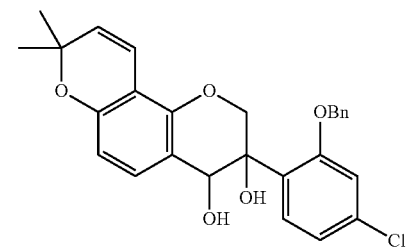<br>(Compound 5-a-36) | ¹H-NMR(CDCl₃): 7.30~7.48(m, 5H), 7.131(d, 1H, J = 8.4 Hz), 7.064(d, 1H, J = 2.0 Hz), 7.015(d, 1H, J = 8.4 Hz), 6.976(dd, 1H, J = 8.4, 2.0 Hz), 6.646(d, 1H, J = 10.0 Hz), 6.427(d, 1H, J = 8.4 Hz), 5.541(d, 1H, J = 10.0 Hz), 5.164(d, 1H, J = 11.2 Hz), 5.129(d, 1H, J = 11.2 Hz), 4.830(s, 1H), 4.629(d, 1H, J = 10.8 Hz), 4.587(s, 1H), 4.365(d, 1H, J = 10.8 Hz), 4.217(d, 1H), 1.921(d, 1H, J = 3.6 Hz), 1.413(s, 1H), 1.393(s, 3H).<br>¹³C-NMR(CDCl₃): 157.197, 153.814, 134.893, 130.037, 129.084, 128.863, 128.823, 128.702, 128.614, 128.542, 127.829, 126.683, 121.470, 116.594, 115.038, 113, 435, 109.829, 76.028, 71.714, 71.314, 69.823, 67.479, 27.969, 27.732. |

TABLE 3-continued

| No. | Chemical structure | $^1$H-NMR, $^{13}$C-NMR (CDCl$_3$, δ) |
|---|---|---|
| Example 47 | 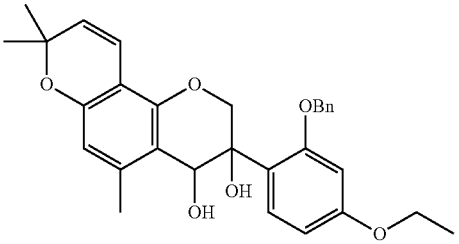<br>(Compound 5-a-47) | $^1$H-NMR(CDCl$_3$): 7.22~7.41(5H), 7.047(d, 1H, J = 8.4 Hz), 6.675(d, 1H, J = 10.0 Hz), 6.658(d, 1H, J = 2.4 Hz), 6.528(dd, 1H, J = 8.4, 2.4 Hz), 6.275(s, 1H), 5.475(d, 1H, J = 10.0 Hz), 5.148(d, 1H, J = 11.2 Hz), 5.094(d, 1H, J = 11.2 Hz), 4.943(t, 1H, J = 1.6 Hz), 4.609(dd, 1H, J = 10.4, 1.6 Hz), 4.431(dd, 1H, J = 10.4, 1.6 Hz), 4.062(d, 1H, J = 1.6 Hz), 4.029(q, 2H, J = 7.2 Hz), 2.216(s, 3H), 1.414(t, 3H, J = 7.2 Hz), 1.397(s, 3H), 1.378(s, 3H).<br>$^{13}$C-NMR(CDCl$_3$): 159.953, 157.649, 153.179, 149.228, 139.803, 135.375, 128.973, 128.688, 127.949, 127.842, 127.545, 120.120, 116.849, 113.010, 111.290, 107.461, 105.524, 101.031, 75.858, 71.685, 70.768, 66.361, 66.232, 63.621, 28.021, 27.783, 18.305, 14.722. |
| Example 48 | 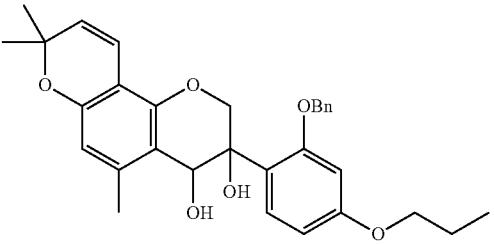<br>(Compound 5-a-48) | $^1$H-NMR(CDCl$_3$): 7.22~7.41(5H), 7.044(d, 1H, J = 8.4 Hz), 6.676(d, 1H, J = 10.0 Hz), 6.667(d, 1H, J = 2.4 Hz), 6.533(dd, 1H, J = 8.4, 2.4 Hz), 6.274(s, 1H), 5.474(d, 1H, J = 10.0 Hz), 5.151(d, 1H, J = 10.8 Hz), 5.097(d, 1H, J = 10.8 Hz), 4.941(t, 1H, J = 1.6 Hz), 4.607(dd, 1H, J = 10.4, 1.6 Hz), 4.429(dd, 1H, J = 10.4, 1.6 Hz), 4.050(d, 1H, J = 1.6 Hz), 3.919(t, 2H, J = 6.8 Hz), 2.214(s, 3H), 1.802(m, 2H), 1.607(d, 1H, J = 2.4 Hz), 1.397(s, 3H), 1.377(s, 3H), 1.039(t, 3H, J = 7.2 Hz).<br>$^{13}$C-NMR(CDCl$_3$): 160.176, 157.675, 153.191, 149.247, 139.810, 135.406, 128.976, 128.692, 127.971, 127.831, 127.547, 120.083, 116.861, 113.031, 111.292, 107.468, 105.626, 101.034, 75.865, 71.700, 70.804, 69.662, 66.387, 66.262, 28.031, 27.797, 22.472, 18.300, 10.485. |
| Example 56 | 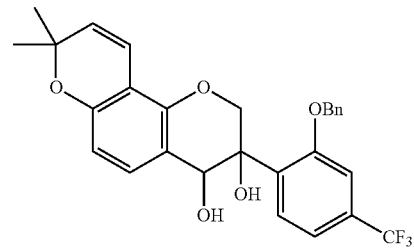<br>(Compound 5-a-56) | $^1$H-NMR(CDCl$_3$): 7.24~7.44(m, 8H), 7.023(d, 1H, J = 8.4 Hz), 6.642(d, 1H, J = 10.0 Hz), 6.436(d, 1H, J = 8.4 Hz), 5.547(d, 1H, J = 10.0 Hz), 5.226(d, 1H, J = 11.2 Hz), 5.191(d, 1H, 11.2 Hz), 4.871(s, 1H), 4.678(d, 1H, J = 10.8 Hz), 4.587(s, 1H), 4.394(d, 1H, J = 10.8 Hz), 4.284(s, 1H), 1.417(s, 3H), 1.397(s, 3H).<br>$^{13}$C-NMR(CDCl$_3$): 156.787, 153.882, 148, 842, 134.727, 132.127, 129.926, 129.119, 128.968, 128.931, 128.360, 127.969, 118.209, 116.518, 115.012, 109.932, 109.564, 109.449, 76.085, 71.870, 71.417, 69.862, 67.450, 27.974, 27.719. |

TABLE 3-continued

| No. | Chemical structure | $^1$H-NMR, $^{13}$C-NMR (CDCl$_3$, δ) |
|---|---|---|
| Example 57 | 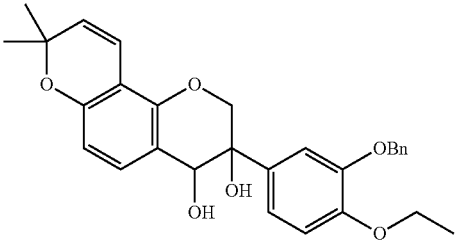<br>(Compound 5-a-57) | $^1$H-NMR(CDCl$_3$): 7.25~7.46(m, 5H), 7.138(d, 1H, J = 2.0 Hz), 7.010(d, 1H, J = 8.4 Hz), 6.987(dd, 1H, J = 8.4, 2.0 Hz), 6.891(d, 1H, J = 8.4 Hz), 6.662(d, 1H, J = 10.0 Hz), 6.455(d, 1H, J = 8.4 Hz), 5.581(d, 1H, J = 10.0 Hz), 5.142(s, 2H), 4.590(d, 1H, J = 10.8 Hz), 4.322(s, 1H), 4.06-4.15(m, 3H), 1.799(d, 1H, J = 2.4 Hz), 1.453(t, 3H, J = 6.8 Hz), 1.425(s, 3H), 1.422(s, 3H).<br>$^{13}$C-NMR(CDCl$_3$): 153.991, 149.223, 148.662, 148.410, 137.104, 132.191, 131.060, 129.142, 128.424, 127.811, 127.436, 119.029, 116.428, 114.270, 113.348, 113.328, 110.308, 109.663, 76.076, 71.363, 71.317, 70.952, 67.852, 64.555, 27.822, 27.781, 14.852. |
| Example 58 | 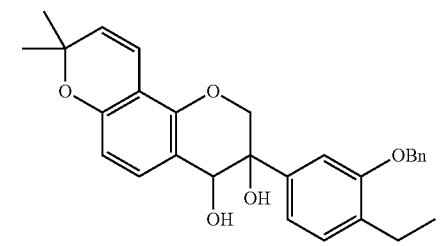<br>(Compound 5-a-58) | $^1$H-NMR(CDCl$_3$): 7.28~7.46(m, 5H), 7.192(d, 1H, J = 8.0 Hz), 7.192(d, 1H, J = 8.0 Hz), 7.160(d, 1H, J = 1.6 Hz), 7.041(d, 1H, J = 8.4 Hz), 6.971(d, 1H, J = 8.0, 1.6 Hz), 6.681(d, 1H, J = 10.0 Hz), 6.473(d, 1H, J = 8.0 Hz), 5.588(d, 1H, J = 10.0 Hz), 5.102(s, 2H), 4.670(d, 1H, J = 11.2 Hz), 4.396(s, 1H), 4.192(d, 1H, J = 11.2 Hz), 2.708(q, 2H, J = 7.6 Hz), 1.850(s, 1H), 1.432(s, 3H), 1.426(s, 3H), 1.222(t, 3H, J = 7.6 Hz).<br>$^{13}$C-NMR(CDCl$_3$): 156.716, 154.040, 148.703, 138.474, 137.190, 132.770, 131.095, 129.187, 129.052, 128.507, 127.799, 127.198, 117.947, 116.437, 114.297, 110.373, 109.715, 109.224, 76.104, 71.599, 71.061, 69.833, 67.913, 27.840, 27.807, 23.090, 14.004. |
| Example 59 | 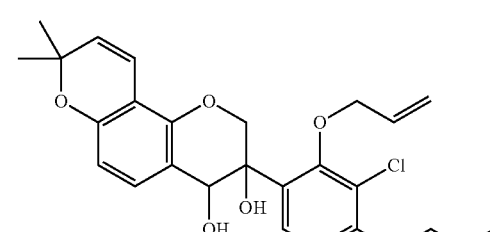<br>(Compound 5-a-59) | $^1$H-NMR(CDCl$_3$): 7.085(d, 1H, J = 8.8 Hz), 7.055(d, 1H, J = 8.4 Hz), 6.720(d, 1H, J = 8.8 Hz), 6.681(d, 1H, J = 10.0 Hz), 6.466(d, 1H, J = 8.4 Hz), 6.0-6.2(m, 2H), 5.574(d, 1H, J = 10.0 Hz), 5.479(m, 2H), 5.324(m, 2H), 4.799(s, 1H), 4.70~4.77(AB, 2H), 4.623(s, 1H), 4.608(m, 2H), 4.410(dd, 1H, J = 10.8, 1.6 Hz), 3.739(s, 1H), 1.965(d, 1H, J = 3.2 Hz), 1.432(s, 3H), 1.417(s, 3H).<br>$^{13}$C-NMR(CDCl$_3$): 155.282, 154.793, 153.887, 148.865, 132.796, 132.277, 130.591, 128.988, 126.606, 125.646, 118.812, 118.106, 117.877, 116.528, 114.859, 110.141, 109.631, 108.594, 76.079, 74.831, 72.043, 70.237, 69.802, 67.795, 27.957, 27.704. |

TABLE 3-continued

| No. | Chemical structure | $^1$H-NMR, $^{13}$C-NMR (CDCl$_3$, δ) |
|---|---|---|
| Example 60 | (Compound 5-a-60) | $^1$H-NMR(CDCl$_3$): 7.067(d, 1H, J = 8.4 Hz), 6.991(d, 1H, J = 8.8 Hz), 6.697(d, 1H, J = 10.0 Hz), 6.635(d, 1H, J = 8.8 Hz), 6.458(d, 1H, J = 8.4 Hz), 6.02~6.11(m, 2H), 5.562(d, 1H, J = 10.0 Hz), 5.41~5.58(m, 2H), 5.27~5.33(m, 2H), 4.775(d, 1H, J = 1.2 Hz), 4.53~4.63(m, 4H), 4.39~4.47(m, 2H), 2.210(s, 3H), 1.429(s, 3H), 1.414(s, 3H). $^{13}$C-NMR(CDCl$_3$): 157.865, 156.792, 153.785, 149.056, 133.140, 132.952, 130.750, 128.782, 124.796, 124.561, 120.995, 117.956, 117.253, 116.694, 114.995, 109.925, 109.594, 107.198, 76.000, 74.782, 72.076, 70.422, 68.947, 67.935, 27.956, 27.696, 10.031. |

H-NMR data and C-NMR data of various 3-phenyl-2,8-dihydropyrano[2,3-f]chromene derivatives (compounds represented by Formula (I-a)) prepared in Examples 1 to 63 are shown in the following Table 4.

TABLE 4

| No. | Chemical structure | $^1$H-NMR, $^{13}$C-NMR (CDCl$_3$, δ) |
|---|---|---|
| Example 1 | (Compound I-a-1) | $^1$H-NMR(CDCl$_3$): 7.25~7.43(m, 5H), 7.248(d, 1H, J = 8.8 Hz), 6.807(d, 1H, J = 8.0 Hz), 6.625(d, 1H, J = 10.0 Hz), 6.521(s, 1H), 6.520(d, 1H, J = 2.4 Hz), 6.512(dd, 1H, J = 8.8, 2.4 Hz), 6.364(d, 1H, J = 8.0 Hz), 5.573(d, 1H, J = 10.0 Hz), 5.043(s, 2H), 4.991(s, 2H), 3.789(s, 3H), 1.415(s, 6H). $^{13}$C-NMR(CDCl$_3$): 160.484, 157.297, 153.356, 149.196, 136.496, 129.335, 129.254, 128.603, 128.559, 127.994, 127.410, 126.520, 121.591, 121.314, 116.947, 116.641, 109.521, 109.211, 105.064, 99.963, 76.038, 70.414, 68.490, 55.402, 27.826. |
| Example 2 | (Compound I-a-2) | $^1$H-NMR(CDCl$_3$): 7.25~7.43(m, 5H), 7.236(d, 1H, J = 8.8 Hz), 6.807(d, 1H, J = 8.0 Hz), 6.625(d, 1H, J = 10.0 Hz), 6.48~6.55(m, 3H), 6.363(d, 1H, J = 8.0 Hz), 5.575(d, 1H, J = 10.0 Hz), 5.045(s, 2H), 4.990(s, 2H), 4.023(q, 2H, J = 6.8 Hz), 1.417(s, 6H), 1.408(t, 3H, J = 6.8 Hz). $^{13}$C-NMR(CDCl$_3$): 159.850, 157.304, 153.334, 149.196, 136.543, 129.306, 129.250, 128.615, 128.602, 127.980, 127.406, 126.503, 121.516, 121.140, 116.980, 116.655, 109.523, 109.199, 105.670, 100.370, 76.037, 70.391, 68.508, 63.596, 27.829, 14.790. |

TABLE 4-continued

| No. | Chemical structure | $^1$H-NMR, $^{13}$C-NMR (CDCl$_3$, δ) |
|---|---|---|
| Example 3 | 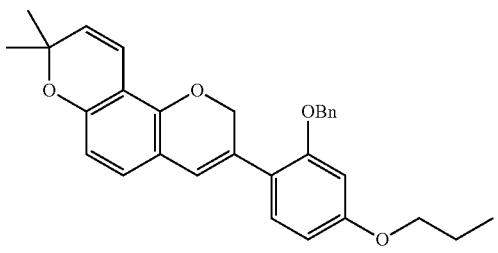<br>(Compound I-a-3) | $^1$H-NMR(CDCl$_3$): 7.25~7.43(m, 5H), 7.233(d, 1H, J = 8.8 Hz), 6.805(d, 1H, J = 8.0 Hz), 6.624(d, 1H, J = 10.0 Hz), 6.523(d, 1H, J = 2.4 Hz), 6.516(s, 1H), 6.505(dd, 1H, J = 8.0, 2.4 Hz), 6.362(d, 1H, J = 8.0 Hz), 5.573(d, 1H, J = 10.0 Hz), 5.043(s, 2H), 4.987(s, 2H), 3.908(t, 2H, J = 6.4 Hz), 1.798(m, 2H), 1.415(s, 6H), 1.032(t, 3H, J = 7.2 Hz).<br>$^{13}$C-NMR(CDCl$_3$): 160.064, 157.309, 153.326, 149.193, 136.551, 129.292, 129.241, 128.629, 128.593, 127.975, 127.427, 126.500, 121.489, 121.085, 116.984, 116.658, 109.518, 109.194, 105.749, 100.360, 76.032, 70.407, 69.656, 68.517, 27.829, 22.535, 10.512. |
| Example 4 | 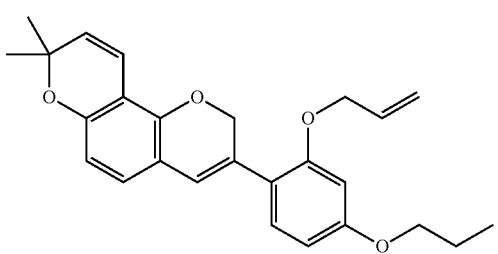<br>(Compound I-a-4) | $^1$H-NMR(CDCl$_3$): 7.216(d, 1H, J = 8.0 Hz), 6.825(d, 1H, J = 8.0 Hz), 6.653(d, 1H, J = 10.0 Hz), 6.498(s, 1H), 6.486(dd, 1H, J = 8.0, 2.4 Hz), 6.453(d, 1H, J = 2.4 Hz), 6.372(d, 1H, J = 8.0 Hz), 6.026(m, 1H), 5.589(d, 1H, J = 10.0 Hz), 5.395(m, 1H, J = 17.2 Hz, 1.6 Hz), 5.272(m, 1H, J = 14.8, 1.6 Hz), 5.028(s, 2H), 4.523(m, 2H, J = 5.2, 1.6 Hz), 3.918(t, 2H, J = 6.4 Hz), 1.810(m, 2H), 1.425(s, 6H), 1.040(t, 3H, J = 7.2 Hz).<br>$^{13}$C-NMR(CDCl$_3$): 160.051, 157.161, 153.327, 149.178, 132.919, 129.275, 128.859, 126.494, 121.412, 120.975, 117.754, 116.993, 116.680, 109.562, 109.212, 105.663, 100.250, 76.029, 69.644, 69.184, 68.492, 27.813, 22.557, 10.514. |
| Example 5 | 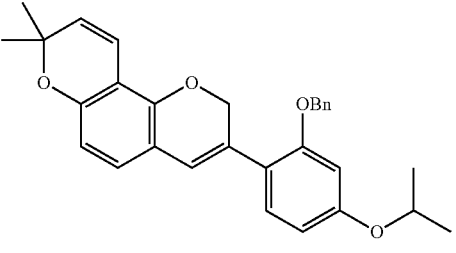<br>(Compound I-a-5) | $^1$H-NMR(CDCl$_3$): 7.25~7.43(m, 5H), 7.227(d, 1H, J = 8.8 Hz), 6.805(d, 1H, J = 8.0 Hz), 6.626(d, 1H, J = 10.0 Hz), 6.519(d, 1H, J = 2.4 Hz), 6.509(s, 1H), 6.500(dd, 1H, J = 8.8, 2.4 Hz), 6.362(d, 1H, J = 8.0 Hz), 5.573(d, 1H, J = 10.0 Hz), 5.035(s, 2H), 4.991(s, 2H), 4.526(m, 1H, J = 6.0 Hz), 1.415(s, 6H), 1.327(d, 6H, J = 6.0 Hz).<br>$^{13}$C-NMR(CDCl$_3$): 158.785, 157.373, 153.323, 149.193, 136.580, 129.256, 129.229, 128.632, 128.585, 127.957, 127.399, 126.492, 121.475, 120.365, 116.986, 116.661, 109.513, 109.184, 106.974, 101.569, 76.025, 70.400, 69.997, 27.826, 22.021. |
| Example 6 | 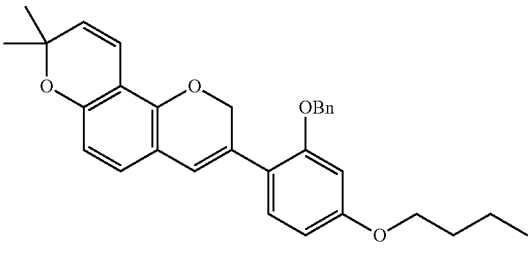<br>(Compound I-a-6) | $^1$H-NMR(CDCl$_3$): 7.25~7.43(m, 5H), 7.231(d, 1H, J = 8.8 Hz), 6.803(d, 1H, J = 8.0 Hz), 6.627(d, 1H, J = 10.0 Hz), 6.520(d, 1H, J = 2.4 Hz), 6.514(s, 1H), 6.510(dd, 1H, J = 8.8, 2.4 Hz), 6.361(d, 1H, J = 8.0 Hz), 5.570(d, 1H, J = 10.0 Hz), 5.040(s, 2H), 4.985(s, 2H), 3.947(t, 2H, J = 8.4 Hz), 1.744(m, 2H), 1.483(m, 2H), 1.435(s, 6H), 0.973(t, 3H, J = 7.4 Hz).<br>$^{13}$C-NMR(CDCl$_3$): 160.078, 157.305, 153.323, 149.192, 136.552, 129.290, 129.245, 128.638, 128.596, 127.977, 127.429, 126.499, 121.486, 121.074, |

TABLE 4-continued

| No. | Chemical structure | $^1$H-NMR, $^{13}$C-NMR (CDCl$_3$, δ) |
|---|---|---|
| | | 116.988, 116.659, 109.520, 109.197, 105.728, 100.344, 76.036, 70.401, 68.518, 67.837, 31.261, 27.830, 19.224, 13.841. |
| Example 7 | 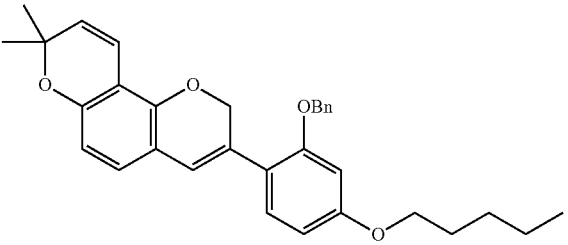<br>(Compound I-a-7) | $^1$H-NMR (CDCl$_3$): 7.25~7.43(m, 5H), 7.246(d, 1H, J = 8.8 Hz), 6.819(d, 1H, J = 8.0 Hz), 6.638(d, 1H, J = 10.0 Hz), 6.535(d, 1H, J = 2.4 Hz), 6.529(s, 1H), 6.518 (dd, 1H, J = 8.8, 2.4 Hz), 6.377(d, 1H, J = 8.0 Hz), 5.586(d, 1H, J = 10.0 Hz), 5.058(s, 2H), 5.002(s, 2H), 3.955(t, 2H, J = 8.4 Hz), 1.790(m, 2H), 1.37~1.44(m, 4H), 1.430(s, 6H), 0.949 (t, 3H, J = 7.4 Hz).<br>$^{13}$C-NMR (CDCl$_3$): 160.062, 157.296, 153.316, 149.183, 136.544, 129.276, 129.225, 128.616, 128.578, 127.961, 127.412, 126.491, 121.472, 121.052, 116.976, 116.651, 109.505, 109.184, 105.732, 100.346, 76.018, 70.393, 68.506, 68.133, 28.906, 28.156, 27.819, 22.430, 14.008. |
| Example 8 | 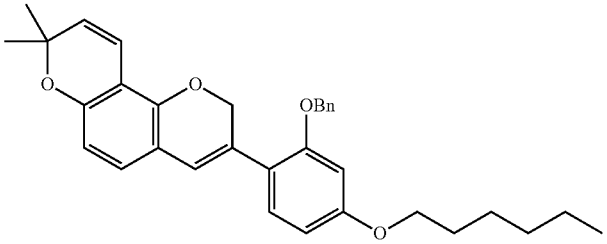<br>(Compound I-a-8) | $^1$H-NMR(CDCl$_3$): 7.25~7.43(m, 5H), 7.231(d, 1H, J = 8.8 Hz), 6.803(d, 1H, J = 8.0 Hz), 6.623(d, 1H, J = 10.0 Hz), 6.520(d, 1H, J = 2.4 Hz), 6.514(s, 1H), 6.503(dd, 1H, J = 8.8, 2.4 Hz), 6.361(d, 1H, J = 8.0 Hz), 5.561(d, 1H, J = 10.0 Hz), 5.041(s, 2H), 4.986(s, 2H), 3.939(t, 2H, J = 8.4 Hz), 1.766(m, 2H), 1.37~1.50(m, 2H), 1.415(s, 6H), 1.30~1.40(m, 4H), 0.910(t, 3H, J = 7.4 Hz).<br>$^{13}$C-NMR(CDCl$_3$): 160.062, 157.296, 153.316, 149.183, 136.544, 129.276, 129.225, 128.616, 128.578, 127.961, 127.412, 126.491, 121.472, 121.052, 116.976, 116.651, 109.505, 109.184, 105.732, 100.346, 76.018, 70.393, 68.506, 68.133, 28.906, 28.156, 27.819, 22.430, 14.008. |
| Example 9 | 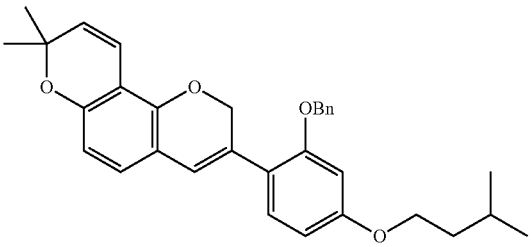<br>(Compound I-a-9) | $^1$H-NMR(CDCl$_3$): 7.25~7.43(m, 5H), 7.231(d, 1H, J = 8.4 Hz), 6.802(d, 1H, J = 8.0 Hz), 6.623(d, 1H, J = 10.0 Hz), 6.45~6.53(m, 3H), 6.361(d, 1H, J = 8.0 Hz), 5.578(d, 1H, J = 10.0 Hz), 5.040(s, 2H), 4.987(s, 2H), 3.971(t, 2H, J = 6.4 Hz), 1.828(m, 1H), 1.663(m, 2H), 1.414(s, 6H), 0.959(d, 6H, J = 6.8 Hz).<br>$^{13}$C-NMR(CDCl$_3$): 160.067, 157.311, 153.338, 149.202, 136.560, 129.287, 129.224, 128.620, 128.589, 127.972, 127.427, 126.504, 121.497, 121.088, 116.982, 116.666, 109.517, 109.195, 105.751, 100.389, 76.024, 70.416, 68.518, 66.509, 37.928, 27.834, 25.010, 22.565. |

TABLE 4-continued

| No. | Chemical structure | $^1$H-NMR, $^{13}$C-NMR (CDCl$_3$, δ) |
|---|---|---|
| Example 10 | 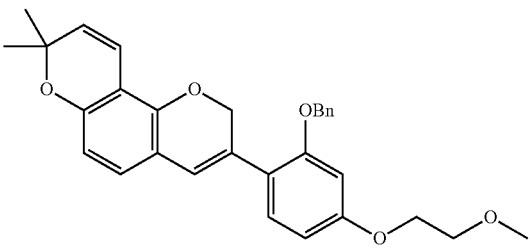<br>(Compound I-a-10) | $^1$H-NMR(CDCl$_3$): 7.25~7.43(m, 5H), 7.235(d, 1H, J = 8.4 Hz), 6.806(d, 1H, J = 8.0 Hz), 6.627(d, 1H, J = 10.0 Hz), 6.587(d, 1H, J = 2.4 Hz), 6.520(s, 1H), 6.517(dd, 1H, J = 8.4, 2.4 Hz), 6.362(d, 1H, J = 8.0 Hz), 5.578(d, 1H, J = 10.0 Hz), 5.036(s, 2H), 4.986(s, 2H), 4.108(t, 2H, J = 4.4 Hz), 3.740(t, 2H, J = 4.4 Hz), 3.447(s, 3H), 1.416(s, 6H).<br>$^{13}$C-NMR(CDCl$_3$): 159.651, 157.280, 153.364, 149.209, 136.493, 129.249, 128.595, 128.520, 127.982, 127.387, 126.524, 121.640, 121.522, 116.945, 116.640, 109.516, 109.205, 105.609, 100.711, 76.041, 70.941, 70.405, 68.477, 67.356, 59.200, 27.830. |
| Example 11 | 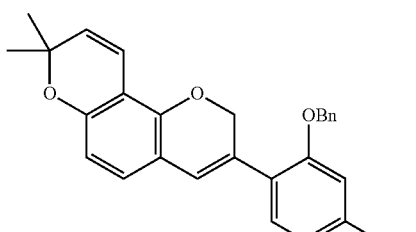<br>(Compound I-a-11) | $^1$H-NMR(CDCl$_3$): 7.28~7.43(m, 10H), 7.241(d, 1H, J = 8.0 Hz), 6.805(d, 1H, J = 8.0 Hz), 6.628(d, 1H, J = 10.0 Hz), 6.600(d, 1H, J = 2.0 Hz), 6.585(dd, 1H, J = 8.0, 2.0 Hz), 6.518(s, 1H), 6.364(d, 1H, J = 8.0 Hz), 5.573(d, 1H, J = 10.0 Hz), 5.046(s, 2H), 5.027(s, 2H), 4.988(s, 2H), 1.416(s, 6H).<br>$^{13}$C-NMR(CDCl$_3$): 159.666, 157.308, 153.382, 149.212, 136.727, 136.473, 129.318, 129.262, 128.625, 128.615, 128.518, 128.071, 128.000, 127.519, 127.409, 126.537, 121.678, 121.555, 116.941, 116.647, 109.531, 109.221, 106.077, 100.760, 76.051, 70.421, 70.203, 68.481, 27.836. |
| Example 12 | 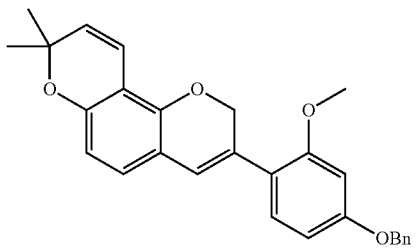<br>(Compound I-a-12) | $^1$H-NMR(CDCl$_3$): 7.30~7.45(m, 5H), 7.205(d, 2H, J = 8.4 Hz), 6.817(d, 1H, J = 8.4 Hz), 6.649(d, 1H, J = 10.0 Hz), 6.551(dd, 1H, J = 8.4, 2.4 Hz), 6.542(d, 1H, J = 2.4 Hz), 6.485(s, 1H), 6.370(d, 1H, J = 8.4 Hz), 5.587(d, 1H, J = 10.0 Hz), 5.065(s, 3H), 5.004(s, 3H), 3.781(s, 3H), 1.420(s, 6H).<br>$^{13}$C-NMR(CDCl$_3$): 159.793, 158.233, 153.368, 149.135, 136.749, 129.302, 129.223, 128.786, 128.618, 128.064, 127.530, 126.532, 121.573, 121.047, 116.894, 116.659, 109.584, 109.236, 105.488, 99.537, 76.032, 70.185, 68.353, 55.374, 27.786. |
| Example 13 | 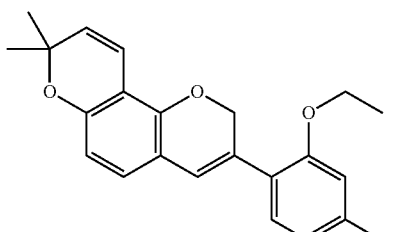<br>(Compound I-a-13) | $^1$H-NMR(CDCl$_3$): 7.30~7.45(m, 5H), 7.215(d, 2H, J = 8.4 Hz), 6.822(d, 1H, J = 8.4 Hz), 6.652(d, 1H, J = 10.0 Hz), 6.547(dd, 1H, J = 8.4, 2.4 Hz), 6.512(d, 1H, J = 2.4 Hz), 6.490(s, 1H), 6.373(d, 1H, J = 8.4 Hz), 5.587(d, 1H, J = 10.0 Hz), 5.053(s, 3H), 5.029(s, 3H), 3.987(q, 2H, J = 6.8 Hz), 1.423(s, 6H), 1.391(t, 3H, J = 6.8 Hz).<br>$^{13}$C-NMR(CDCl$_3$): 159.723, 157.565, 153.336, 149.196, 136.787, 129.292, 129.108, 128.970, 128.606, 128.039, 127.517, 126.519, 121.350, 121.326, 116.998, 116.667, 109.553, 109.223, 105.537, 100.155, 76.031, 70.158, 68.443, 63.757, 27.809, 14.730. |

TABLE 4-continued

| No. | Chemical structure | $^1$H-NMR, $^{13}$C-NMR (CDCl$_3$, δ) |
|---|---|---|
| Example 14 | 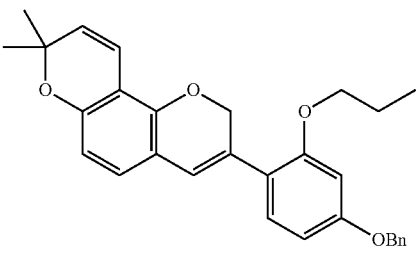<br>(Compound I-a-14) | $^1$H-NMR(CDCl$_3$): 7.30~7.45(m, 5H), 7.222(d, 2H, J = 8.4 Hz), 6.823(d, 1H, J = 8.4 Hz), 6.659(d, 1H, J = 10.0 Hz), 6.546(dd, 1H, J = 8.4, 2.4 Hz), 6.522(d, 1H, J = 2.4 Hz), 6.498(s, 1H), 6.375(d, 1H, J = 8.4 Hz), 5.589(d, 1H, J = 10.0 Hz), 5.058(s, 3H), 5.026(s, 3H), 3.885(t, 2H, J = 6.4 Hz), 1.794(m, 2H), 1.425(s, 6H), 1.024(t, 3H, J = 7.2 Hz).<br>$^{13}$C-NMR(CDCl$_3$): 159.732, 157.763, 153.337, 149.218, 136.812, 129.281, 129.105, 128.897, 128.612, 128.043, 127.521, 126.521, 121.357, 121.261, 117.026, 116.683, 109.553, 109.219, 105.449, 100.108, 76.044, 70.167, 69.824, 68.513, 27.832, 22.517, 10.802. |
| Example 15 | 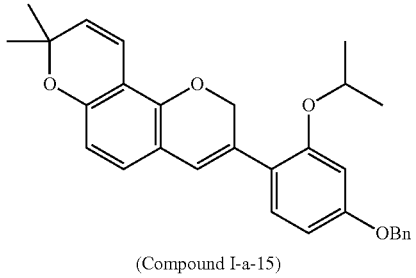 [SMILES: CC(C)Oc1cc(OCc2ccccc2)ccc1C1=Cc2ccc3c(c2OC1)C=CC(C)(C)O3]<br>(Compound I-a-15) | $^1$H-NMR(CDCl$_3$): 7.30~7.45(m, 5H), 7.219(d, 2H, J = 8.4 Hz), 6.824(d, 1H, J = 8.4 Hz), 6.657(d, 1H, J = 10.0 Hz), 6.547(dd, 1H, J = 8.4, 2.4 Hz), 6.511(d, 1H, J = 2.4 Hz), 6.467(s, 1H), 6.374(d, 1H, J = 8.4 Hz), 5.588(d, 1H, J = 10.0 Hz), 5.053(s, 3H), 5.013(s, 3H), 4.501(m, 1H, J = 6.0 Hz), 1.423(s, 6H), 1.307(d, 6H, J = 6.0 Hz).<br>13C-NMR(CDCl$_3$): 159.646, 156.361, 153.301, 149.208, 136.818, 129.350, 129.296, 129.262, 128.618, 128.042, 127.522, 126.478, 122.274, 121.161, 117.059, 116.673, 109.558, 109.213, 105.618, 101.356, 76.025, 70.234, 70.192, 68.537, 27.815, 21.983. |
| Example 16 | 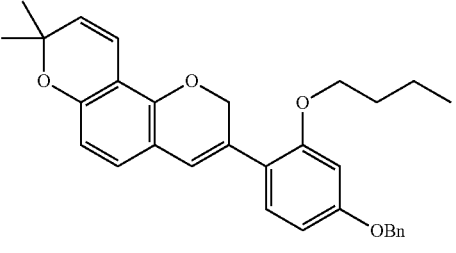<br>(Compound I-a-16) | $^1$H-NMR(CDCl$_3$): 7.30~7.45(m, 5H), 7.219(d, 2H, J = 8.4 Hz), 6.823(d, 1H, J = 8.4 Hz), 6.664(d, 1H, J = 10.0 Hz), 6.540(dd, 1H, J = 8.4, 2.4 Hz), 6.527(d, 1H, J = 2.4 Hz), 6.496(s, 1H), 6.375(d, 1H, J = 8.4 Hz), 5.589(d, 1H, J = 10.0 Hz), 5.056(s, 3H), 5.016(s, 3H), 3.921(t, 2H, J = 6.4 Hz), 1.751(m, 2H), 1.467(m, 2H), 1.426(s, 6H), 9.55(t, 3H, J = 7.2 Hz).<br>$^{13}$C-NMR(CDCl$_3$): 159.721, 157.763, 153.329, 149.217, 136.806, 129.263, 129.088, 128.853, 128.598, 128.029, 127.512, 126.517, 121.339, 121.254, 117.018, 116.678, 109.536, 109.211, 105.409, 100.094, 76.034, 70.158, 68.488, 67.934, 31.204, 27.830, 19.359, 13.808. |
| Example 17 | 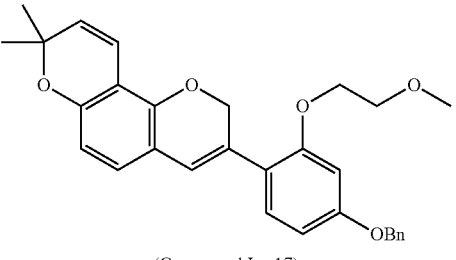<br>(Compound I-a-17) | $^1$H-NMR(CDCl$_3$): 7.30~7.45(m, 5H), 7.222(d, 2H, J = 8.4 Hz), 6.820(d, 1H, J = 8.4 Hz), 6.662(d, 1H, J = 10.0 Hz), 6.571(dd, 1H, J = 8.4, 2.4 Hz), 6.534(d, 1H, J = 2.4 Hz), 6.516(s, 1H), 6.372(d, 1H, J = 8.4 Hz), 5.588(d, 1H, J = 10.0 Hz), 5.057(s, 3H), 5.030(s, 3H), 4.075(t, 2H, J = 4.8 Hz), 3.716(t, 2H, J = 4.8 Hz), 3.417(s, 6H), 1.426(s, 6H).<br>$^{13}$C-NMR(CDCl$_3$): 159.631, 157.399, 153.348, 149.248, 136.737, 129.240, 129.175, 128.634, |

TABLE 4-continued

| No. | Chemical structure | ¹H-NMR, ¹³C-NMR (CDCl₃, δ) |
|---|---|---|
| | | 128.613, 128.053, 127.506, 126.530, 121.569 121.476, 117.000, 116.693, 109.534, 109.191, 106.098, 100.507, 76.037, 70.856, 70.180, 68.405, 67.595, 59.105, 27.827. |
| Example 18 | 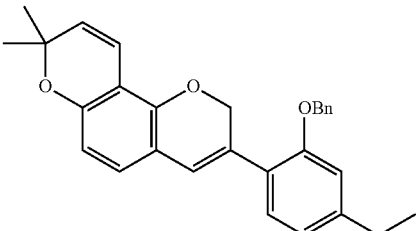<br>(Compound I-a-18) | ¹H-NMR(CDCl₃): 7.30~7.45(m, 5H), 7.269(d, 2H, J = 7.2 Hz), 6.848(d, 1H, J = 7.2 Hz), 6.831(d, 1H, J = 8.0 Hz), 6.821(s, 1H), 6.647(d, 1H, J = 10.0 Hz), 6.582(s, 1H), 6.385(d, 1H, J = 8.0 Hz), 5.591(d, 1H, J = 10.0 Hz), 5.091(s, 2H), 5.029(s, 2H), 2.661(q, 2H, J = 7.6 Hz), 1.437(s, 6H), 1.258(t, 3H, J = 7.6 Hz).<br>¹³C-NMR(CDCl₃): 156.345, 153.498, 149.352, 145.527, 136.824, 129.242, 128.850, 128.721, 128.572, 127.924, 127.459, 126.647, 125.831, 122.230, 120.671, 116.927, 116.664, 112.085, 109.547, 109.230, 76.069, 70.449, 68.484, 28.892, 27.856, 15.468. |
| Example 19 | 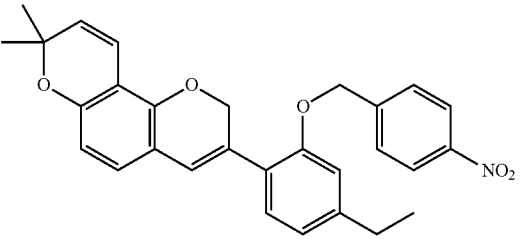<br>(Compound I-a-19) | ¹H-NMR(CDCl₃): 8.241(d, 2H, J = 8.8 Hz), 7.794(d, 2H, J = 8.8 Hz), 7.268(d, 1H, J = 8.0 Hz), 6.882(d, 1H, J = 8.0 Hz), 6.837(d, 1H, J = 8.0 Hz), 6.763(s, 1H), 6.635(d, 1H, J = 10.0 Hz), 6.571(s, 1H), 6.395(d, 1H, J = 8.0 Hz), 5.605(d, 1H, J = 10.0 Hz), 5.190(s, 2H), 5.010(s, 2H), 2.650(q, 2H, J = 7.6 Hz), 1.436(s, 6H), 1.243(t, 3H, J = 7.6 Hz).<br>¹³C-NMR(CDCl₃): 155.619, 153.656, 149.223, 147.562, 145.681, 144.206, 129.448, 129.089, 128.357, 127.662, 126.670, 125.875, 123.867, 122.720, 121.343, 116.696, 116.482, 112.132, 109.596, 109.411, 76.156, 69.267, 68.325, 28.849, 27.860, 15.464. |
| Example 20 | 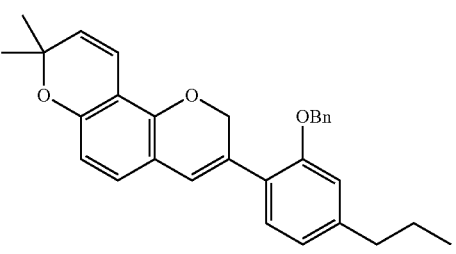<br>(Compound I-a-20) | ¹H-NMR(CDCl₃): 7.30~7.45(m, 5H), 7.252(d, 1H, J = 7.2 Hz), 6.825(d, 1H, J = 7.2 Hz), 6.820(d, 1H, J = 8.0 Hz), 6.793(s, 1H), 6.642(d, 1H, J = 10.0 Hz), 6.580(s, 1H), 6.370(d, 1H, J = 8.0 Hz), 5.587(d, 1H, J = 10.0 Hz), 5.082(s, 2H), 5.025(s, 2H), 2.589(t, 2H, J = 7.6 Hz), 1.655(m, 2H, J = 7.6 Hz), 1.433(s, 6H), 0.958(t, 3H, J = 7.6 Hz).<br>¹³C-NMR(CDCl₃): 156.249, 153.492, 149.357, 143.970, 136.831, 129.235, 128.862, 128.593, 128.565, 127.914, 127.456, 126.642, 125.820, 122.222, 121.337, 116.936, 116.668, 112.668, 109.542, 109.224, 76.066, 70.449, 68.486, 38.060, 27.859, 24.436, 13.828. |

TABLE 4-continued

| No. | Chemical structure | $^1$H-NMR, $^{13}$C-NMR (CDCl$_3$, δ) |
|---|---|---|
| Example 21 | 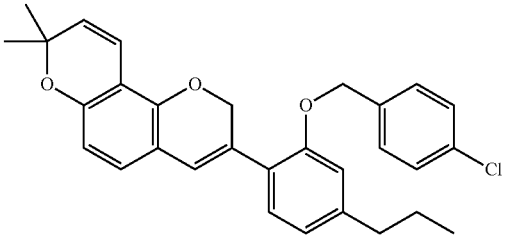<br>(Compound I-a-21) | $^1$H-NMR(CDCl$_3$): 7.343(s, 4H), 7.239(d, 1H, J = 8.0 Hz), 6.819(d, 2H, J = 8.0 Hz), 6.745(s, 1H), 6.629(d, 1H, J = 10.0 Hz), 6.550(s, 1H), 6.374(d, 1H, J = 8.0 Hz), 5.587(d, 1H, J = 10.0 Hz), 5.031(s, 2H), 4.981(s, 2H), 2.574(t, 2H, J = 7.2 Hz), 1.639(m, 2H), 1.425(s, 6H), 0.945(t, 3H, J = 7.2 Hz). |
| Example 22 | 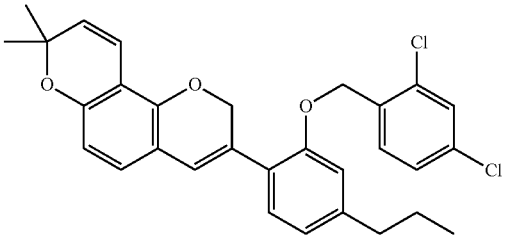<br>(Compound I-a-22) | $^1$H-NMR(CDCl$_3$): 7.472(d, 1H, J = 8.0 Hz), 7.421(d, 1H, J = 2.0 Hz), 7.250(dd, 1H, J = 8.0, 2.0 Hz), 7.238(d, 1H, J = 8.0 Hz), 6.834(d, 1H, J = 8.0 Hz), 6.828(d, 1H, J = 8.0 Hz), 6.744(s, 1H), 6.636(d, 1H, J = 10.0 Hz), 6.557(s, 1H), 6.381(d, 1H, J = 8.0 Hz), 5.595(d, 1H, J = 10.0 Hz), 5.123(s, 2H), 5.000(s, 2H), 2.582(t, 2H, J = 7.2 Hz), 1.643(m, 2H), 1.429(s, 6H), 0.948(t, 3H, J = 7.2 Hz). |
| Example 23 | 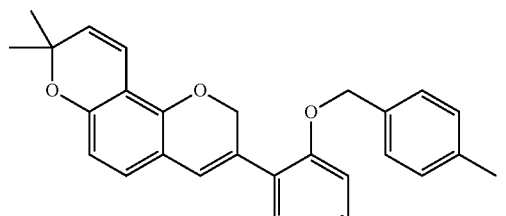<br>(Compound I-a-23) | $^1$H-NMR(CDCl$_3$): 7.289(d, 2H, J = 8.0 Hz), 7.234(d, 1H, J = 8.4 Hz), 7.170(d, 2H, J = 8.0 Hz), 6.809(d, 1H, J = 8.4 Hz), 6.793(dd, 1H, J = 8.4, 2.0 Hz), 6.778(d, 1H, J = 2.0 Hz), 6.625(d, 1H, J = 10.0 Hz), 6.548(s, 1H), 6.362(d, 1H, J = 8.4 Hz), 5.571(d, 1H, J = 10.0 Hz), 5.012(s, 2H), 4.993(s, 2H), 2.572(t, 2H, J = 7.6 Hz), 2.349(s, 3H), 1.642(m, 2H, J = 7.6 Hz), 1.415(s, 6H), 0.946(t, 3H, J = 7.2 Hz).<br>$^{13}$C-NMR(CDCl$_3$): 156.286, 153.417, 149.335, 143.948, 137.651, 133.719, 129.221, 128.974, 128.524, 127.591, 126.612, 125.784, 122.081, 121.208, 116.958, 116.667, 112.522, 109.514, 109.186, 76.040, 70.301, 68.478, 38.060, 27.829, 24.468, 13.854. |
| Example 24 | 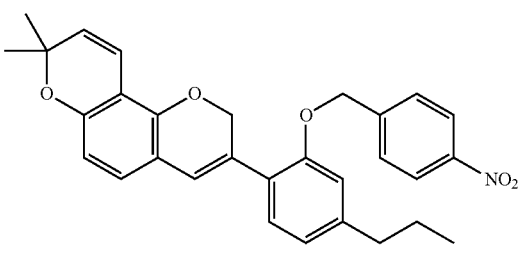<br>(Compound I-a-24) | $^1$H-NMR(CDCl$_3$): 8.231(d, 2H, J = 8.8 Hz), 7.587(d, 2H, J = 8.8 Hz), 7.250(d, 1H, J = 8.0 Hz), 6.847(d, 1H, J = 8.0 Hz), 6.820(d, 1H, J = 8.0 Hz), 6.728(s, 1H), 6.629(d, 1H, J = 10.0 Hz), 6.566(s, 1H), 6.387(d, 1H, J = 8.0 Hz), 5.597(d, 1H, J = 10.0 Hz), 5.176(s, 2H), 5.003(s, 2H), 2.572(t, 2H, J = 7.2 Hz), 1.630(m, 2H), 1.428(s, 6H), 0.938(t, 3H, J = 7.6 Hz).<br>$^{13}$C-NMR(CDCl$_3$): 155.522, 153.649, 149.224, 147.548, 144.214, 144.120, 129.433, 128.954, 128.364, 127.656, 126.663, 125.854, 123.850, 122.705, 121.992, 116.702, 116.485, 112.695, 109.588, 109.399, 76.144, 69.253, 68.321, 37.985, 27.860, 24.427, 13.791. |

TABLE 4-continued

| No. | Chemical structure | $^1$H-NMR, $^{13}$C-NMR (CDCl$_3$, δ) |
|---|---|---|
| Example 25 | 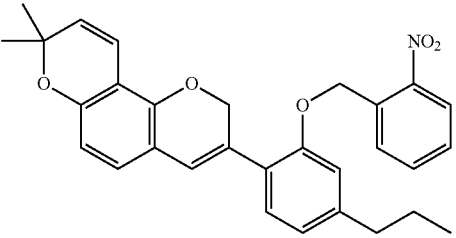<br>(Compound I-a-25) | $^1$H-NMR(CDCl$_3$): 8.172(d, 1H, J = 8.0 Hz), 7.895(d, 1H, J = 8.0 Hz), 7.658(t, 1H, J = 8.0 Hz), 7.478(t, 1H, J = 8.0 Hz), 7.243(d, 1H, J = 8.0 Hz), 6.848(d, 2H, J = 8.0 Hz), 6.752(s, 1H), 6.648(d, 1H, J = 10.0 Hz), 6.586(s, 1H), 6.392(d, 1H, J = 8.0 Hz), 5.599(d, 1H, J = 10.0 Hz), 5.510(s, 2H), 5.042(s, 2H), 2.569(t, 2H, J = 7.2 Hz), 1.625(m, 2H), 1.433(s, 6H), 0.936(t, 3H, J = 7.6 Hz).<br>$^{13}$C-NMR(CDCl$_3$): 155.504, 153.590, 149.288, 146.781, 144.288, 134.182, 133.766, 129.380, 128.983, 128.630, 128.479, 128.311, 126.677, 125.737, 124.973, 122.756, 121.887, 116.793, 116.543, 112.905, 109.587, 109.346, 76.121, 68.356, 67.312, 37.992, 27.872, 24.480, 13.801. |
| Example 26 | 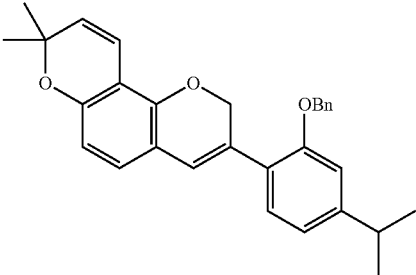<br>(Compound I-a-26) | $^1$H-NMR(CDCl$_3$): 7.30~7.45(m, 5H), 7.281(d, 1H, J = 7.2 Hz), 6.877(d, 1H, J = 7.2 Hz), 6.843(s, 1H), 6.833(d, 1H, J = 8.0 Hz), 6.646(d, 1H, J = 10.0 Hz), 6.582(s, 1H), 6.385(d, 1H, J = 8.0 Hz), 5.593(d, 1H, J = 10.0 Hz), 5.096(s, 2H), 5.031(s, 2H), 2.910(m, 1H, J = 7.0 Hz), 1.436(s, 6H), 1.267(d, 6H, J = 7.0 Hz).<br>$^{13}$C-NMR(CDCl$_3$): 156.295, 153.471, 150.198, 149.340, 136.814, 129.240, 128.873, 128.691, 128.564, 127.924, 127.501, 126.636, 125.938, 122.224, 119.160, 116.925, 116.659, 110.754, 109.543, 109.216, 76.062, 70.446, 68.453, 34.166, 27.840, 23.914. |
| Example 27 | 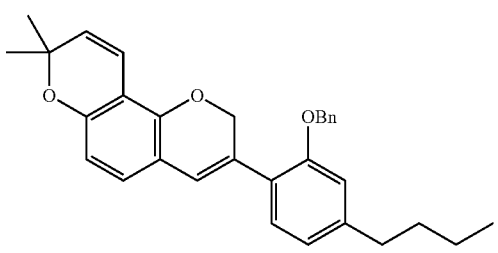<br>(Compound I-a-27) | $^1$H-NMR(CDCl$_3$): 7.30~7.45(m, 5H), 7.264(d, 1H, J = 7.2 Hz), 6.840(d, 1H, J = 7.2 Hz), 6.832(d, 1H, J = 8.0 Hz), 6.804(s, 1H), 6.654(d, 1H, J = 10.0 Hz), 6.590(s, 1H), 6.394(d, 1H, J = 8.0 Hz), 5.598(d, 1H, J = 10.0 Hz), 5.091(s, 2H), 5.036(s, 2H), 2.622(t, 2H, J = 7.6 Hz), 1.623(m, 2H), 1.444(s, 6H), 1.375(m, 2H), 0.954(t, 3H, J = 7.6 Hz).<br>$^{13}$C-NMR(CDCl$_3$): 156.212, 153.455, 149.331, 144.180, 136.791, 129.229, 128.867 128.588, 128.553, 127.902, 127.449, 126.626, 125.728, 122.179, 121.252, 116.929, 116.652, 112.540, 109.529, 109.213, 76.054, 70.380, 68.463, 35.669, 33.512, 27.837, 22.345, 13.954. |

TABLE 4-continued

| No. | Chemical structure | $^1$H-NMR, $^{13}$C-NMR (CDCl$_3$, δ) |
|---|---|---|
| Example 28 | 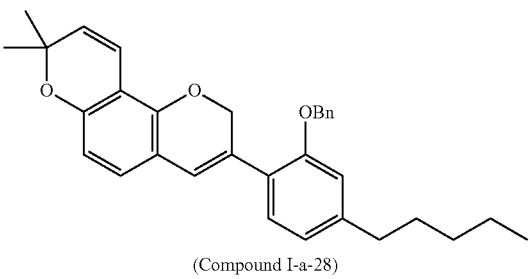 [SMILES: CCCCCc1ccc(C2=Cc3ccc4c(c3OC2)C=CC(C)(C)O4)c(OCc2ccccc2)c1]<br>(Compound I-a-28) | $^1$H-NMR (CDCl$_3$): 7.30~7.45 (m, 5H), 7.250(d, 1H, J = 7.2 Hz), 6.825(d, 1H, J = 7.2 Hz), 6.816(d, 1H, J = 8.0 Hz), 6.787(s, 1H), 6.635(d, 1H, J = 10.0 Hz), 6.574(s, 1H), 6.375(d, 1H, J = 8.0 Hz), 5.585(d, 1H, J = 10.0 Hz), 5.080(s, 2H), 5.018(s, 2H), 2.598(t, 2H, J = 7.6 Hz), 1.618(m, 2H), 1.428(s, 6H), 1.325(m, 4H), 0.906(t, 3H, J = 6.8 Hz).<br>$^{13}$C-NMR(CDCl$_3$): 156.212, 153.449, 149.330, 144.237, 136.793, 129.239, 128.881, 128.595, 128.561, 127.912, 127.452, 126.627, 125.728, 122.179, 121.238, 116.934, 116.651, 112.504, 109.533, 109.215, 76.059, 70.372, 68.464, 35.956, 31.479, 31.068, 27.837, 22.538, 14.036. |
| Example 29 | 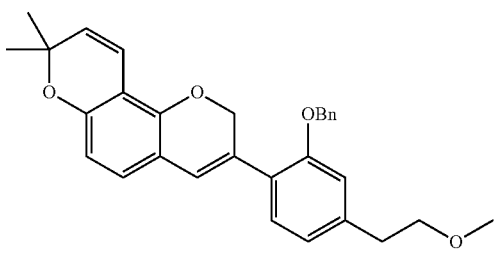<br>(Compound I-a-29) | $^1$H-NMR(CDCl$_3$): 7.30~7.45(m, 5H), 7.271(d, 1H, J = 7.2 Hz), 6.860(d, 1H, J = 7.2 Hz), 6.851(s, 1H), 6.833(d, 1H, J = 8.0 Hz), 6.638(d, 1H, J = 10.0 Hz), 6.577(s, 1H), 6.383(d, 1H, J = 8.0 Hz), 5.592(d, 1H, J = 10.0 Hz), 5.085(s, 2H), 5.016(s, 2H), 3.616(t, 2H, J = 6.8 Hz), 3.368(s, 3H), 2.887(t, 2H, J = 6.8 Hz), 1.433(s, 6H).<br>$^{13}$C-NMR(CDCl$_3$): 156.258, 153.509, 149.343, 140.209, 136.709, 129.253, 128.726, 128.566, 127.931, 127.447, 126.663, 126.362, 122.375, 121.594, 116.867, 116.621, 112.952, 109.534, 109.237, 76.068, 73.341, 70.385, 68.401, 58.694, 36.173, 27.835. |
| Example 30 | 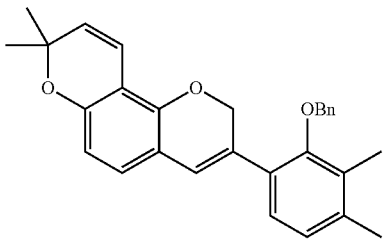<br>(Compound I-a-30) | $^1$H-NMR(CDCl$_3$): 7.30~7.45(m, 5H), 7.100(d, 1H, J = 8.0 Hz), 6.981(d, 1H, J = 8.0 Hz), 6.851(d, 1H, J = 8.0 Hz), 6.672(d, 1H, J = 10.0 Hz), 6.643(s, 1H), 6.409(d, 1H, J = 8.0 Hz), 5.613(d, 1H, J = 10.0 Hz), 5.078(s, 2H), 4.770(s, 2H), 2.306(s, 3H), 2.230(s, 3H), 1.455(s, 6H).<br>$^{13}$C-NMR(CDCl$_3$): 154.695, 153.636, 149.312, 138.313, 137.128, 129.312, 128.827, 128, 679, 128.498, 128.425, 128.176, 127.986, 126.703, 126.018, 125.858, 122.605, 116.661, 116.609, 109.601, 109.266, 76.131, 74.894, 68.268, 27.878, 20.124, 12.428. |
| Example 31 | 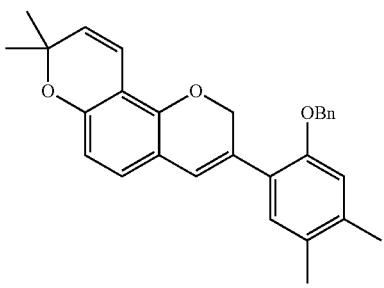<br>(Compound I-a-31) | $^1$H-NMR(CDCl$_3$): 7.30~7.45(m, 5H), 7.125(s, 1H), 6.838(d, 1H, J = 8.0 Hz), 6.780(s, 1H), 6.652(d, 1H, J = 10.0 Hz), 6.581(s, 1H), 6.390(d, 1H, J = 8.0 Hz), 5.597(d, 1H, J = 10.0 Hz), 5.061(s, 2H), 5.033(s, 2H), 2.275(s, 3H), 2.237(s, 3H), 1.438(s, 6H).<br>$^{13}$C-NMR(CDCl$_3$): 154.361, 153.428, 149.310, 137.257, 136.995, 129.915, 129.224, 129.077, 128.861, 128.541, 127.843, 127.370, 126.605, 125.653, 122.002, 116.932, 116.666, 114.121, 109.528, 109.200, 76.049, 70.647, 68.528, 27.838, 19.986, 18.803. |

TABLE 4-continued

| No. | Chemical structure | $^1$H-NMR, $^{13}$C-NMR (CDCl$_3$, δ) |
|---|---|---|
| Example 32 | 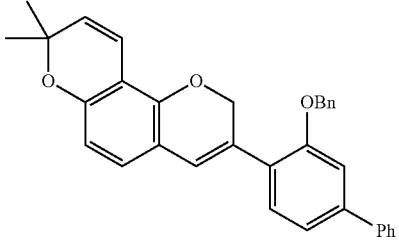<br>(Compound I-a-32) | $^1$H-NMR(CDCl$_3$): 7.598(d, 2H, J = 7.2 Hz), 7.30~7.50(m, 9H), 7.246(d, 1H, J = 7.2 Hz), 7.202(s, 1H), 6.875(d, 1H, J = 7.2 Hz), 6.688(s, 1H), 6.676(d, 1H, J = 10.0 Hz), 6.422(d, 1H, J = 8.0 Hz), 5.818(d, 1H, J = 10.0 Hz), 5.176(s, 2H), 5.091(s, 2H), 1.461(s, 6H).<br>$^{13}$C-NMR(CDCl$_3$): 156.596, 153.662, 149.427, 141.997, 140.685, 136.574, 129.294, 129.086, 128.793, 128.627, 128.339, 128.034, 127.496, 127.344, 127.004, 126.802, 122.871, 120.081, 116.828, 116.601, 111.175, 109.560, 109.334, 76.121, 70.551, 68.363, 27.860. |
| Example 33 | 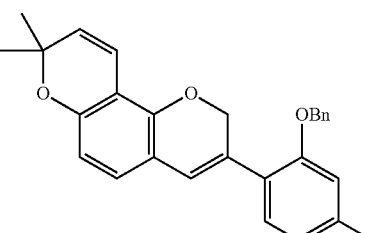<br>(Compound I-a-33) | $^1$H-NMR(CDCl$_3$): 7.30~7.45(m, 5H), 7.273(d, 1H, J = 7.2 Hz), 7.140(t, 1H, J = 7.2 Hz), 7.030(d, 2H, J = 7.2 Hz), 6.835(d, 1H, J = 8.0 Hz), 6.659(d, 1H, J = 2.4 Hz), 6.641(d, 1H, J = 10.0 Hz), 6.587(dd, 1H, J = 8.0, 2.4 Hz), 6.562(s, 1H), 6.386(d, 1H, J = 8.0 Hz), 5.595(d, 1H, J = 10.0 Hz), 5.021(s, 2H), 5.018(s, 2H), 1.433(s, 6H).<br>$^{13}$C-NMR(CDCl$_3$): 158.032, 157.286, 156.689, 153.527, 149.284, 136.226, 129.791, 129.487, 129.306, 128.620, 128.283, 128.044, 127.691, 127.471, 126.652, 123.538, 123.433, 122.286, 119.085, 116.823, 116.603, 110.737, 109.552, 109.291, 76.098, 70.450, 68.380, 27.846. |
| Example 34 | 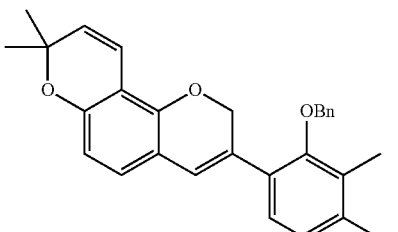<br>(Compound I-a-34) | $^1$H-NMR(CDCl$_3$): 7.30~7.45(m, 10H), 7.133(d, 2H, J = 8.4 Hz), 6.840(d, 1H, J = 8.0 Hz), 6.750(d, 1H, J = 8.4 Hz), 6.669(d, 1H, 10.0 Hz), 6.605(s, 1H), 6.405(d, 1H, J = 8.0 Hz), 5.613(d, 1H, J = 10.0 Hz), 5.115(s, 2H), 5.062(s, 2H), 4.796(s, 2H), 2.247(s, 3H), 1.426(s, 6H).<br>$^{13}$C-NMR(CDCl$_3$): 157.621, 155.594, 153.525, 149.214, 137.161, 137.008, 129.322, 128.594, 128.539, 128.435, 128.255, 128.040, 127.844, 127.101, 126.590, 126.327, 125.439, 122.095, 120.918, 116.754, 116.618, 109.597, 109.244, 107.807, 76.116, 74.951, 70.207, 68.309, 27.873, 9.441. |
| Example 35 | 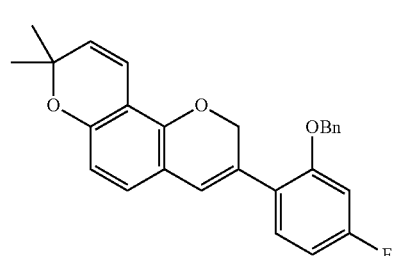<br>(Compound I-a-35) | $^1$H-NMR(CDCl$_3$): 7.30~7.42(m, 5H), 7.267(dd, 1H, J = 8.8, 6.8 Hz), 6.821(d, 1H, J = 8.4 Hz), 6.65~6.71(m, 2H), 6.619(d, 1H, J = 10.0 Hz), 6.524(s, 1H), 6.375(d, 1H, J = 8.4 Hz), 5.581(d, 1H, J = 10.0 Hz), 5.041(s, 2H), 4.972(s, 2H), 1.419(s, 6H).<br>$^{13}$C-NMR(CDCl$_3$): 163.801, 162.400, 157.261, 153.659, 149.306, 135.951, 129.599, 129.346, 128.695, 128.191, 127.898, 127.405, 126.733, 124.477, 122.747, 116.650, 116.545, 109.455, 107.590, 100.416, 76.129, 70.638, 68.260, 27.729. |

TABLE 4-continued

| No. | Chemical structure | $^1$H-NMR, $^{13}$C-NMR (CDCl$_3$, δ) |
|---|---|---|
| Example 36 | 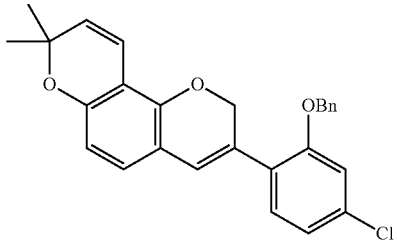<br>(Compound I-a-36) | $^1$H-NMR(CDCl$_3$): 7.30~7.42(m, 5H), 7.244(d, 1H, J = 8.0 Hz), 6.961(dd, 1H, J = 8.0, 2.0 Hz), 6.943(d, 1H, J = 2.0 Hz), 6.822(d, 1H, J = 8.4 Hz), 6.611(d, 1H, J = 10.0 Hz), 6.564(s, 1H), 6.372(d, 1H, J = 8.4 Hz), 5.581(d, 1H, J = 10.0 Hz), 5.050(s, 2H), 4.962(s, 2H), 1.419(s, 6H).<br>$^{13}$C-NMR(CDCl$_3$): 156.753, 153.804, 149.400, 135.940, 134.044, 129.483, 129.371, 128.700, 128.225, 127.620, 127.483, 127.015, 126.856, 123.236, 121.313, 116.580, 116.509, 112.791, 109.567, 109.421, 76.177, 70.718, 68.140, 27.871. |
| Example 37 | 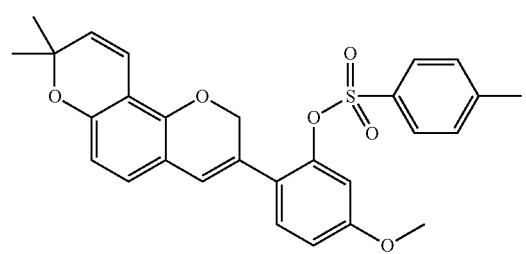<br>(Compound I-a-37) | $^1$H-NMR(CDCl$_3$): 7.556(d, 2H, J = 8.0 Hz), 7.068(d, 1H, J = 8.0 Hz), 7.029(d, 2H, J = 8.0 Hz), 6.943(d, 1H, J = 2.8 Hz), 6.805(dd, 1H, J = 8.0, 2.8 Hz), 6.632(d, 1H, J = 8.0 Hz), 6.602(d, 1H, J = 10.0 Hz), 6.353(d, 1H, J = 8.0 Hz), 5.954(s, 1H), 5.612(d, 1H, J = 10.0 Hz), 4.716(s, 2H), 3.822(s, 3H), 2.277(s, 3H), 1.450(s, 6H).<br>$^{13}$C-NMR(CDCl$_3$): 159.744, 153.799, 148.644, 147.537, 145.335, 132.181, 129.582, 129.482, 129.462, 128.463, 126.541, 125.429, 124.620, 123.330, 116.449, 116.134, 113.703, 109.478, 109.368, 109.202, 76.191, 67.578, 55.652, 27.851, 21.610. |
| Example 38 | 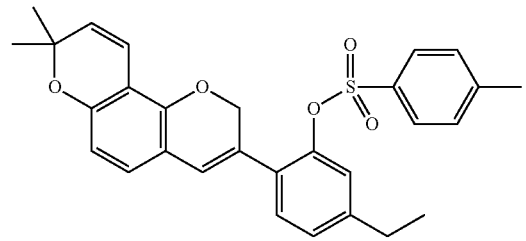<br>(Compound I-a-38) | $^1$H-NMR(CDCl$_3$): 7.544(d, 2H, J = 8.0 Hz), 7.202(s, 1H), 7.079(s, 2H), 7.026(d, 2H, J = 8.0 Hz), 6.644(d, 1H, J = 8.0 Hz), 6.603(d, 1H, J = 10.0 Hz), 6.356(d, 1H, J = 8.0 Hz), 6.015(s, 1H), 5.618(d, 1H, J = 10.0 Hz), 4.743(s, 2H), 2.669(q, 2H, J = 7.6 Hz), 2.277(s, 3H), 1.451(s, 6H), 1.240(t, 3H, J = 7.6 Hz).<br>$^{13}$C-NMR(CDCl$_3$): 153.897, 148.748, 146.776, 145.591, 145.213, 132.320, 129.511, 129.444, 128.889, 128.441, 126.962, 126.666, 125.673, 123.839, 123.339, 116.440, 116.090, 109.485, 109.223, 76.209, 67.526, 28.311, 27.853, 21.604, 15.134. |
| Example 39 | 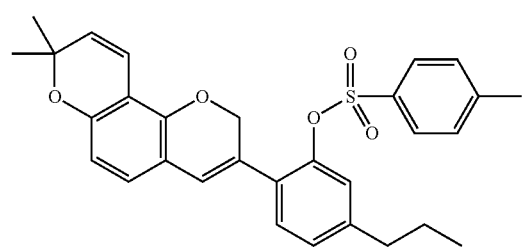<br>(Compound I-a-39) | $^1$H-NMR(CDCl$_3$): 7.535(d, 2H, J = 8.0 Hz), 7.188(s, 1H), 7.061(s, 2H), 7.023(d, 2H, J = 8.0 Hz), 6.644(d, 1H, J = 8.0 Hz), 6.606(d, 1H, J = 10.0 Hz), 6.357(d, 1H, J = 8.0 Hz), 6.012(s, 1H), 5.618(d, 1H, J = 10.0 Hz), 4.746(s, 2H), 2.601(t, 2H, J = 7.6 Hz), 2.277(s, 3H), 1.643(m, 2H, J = 7.6 Hz), 1.451(s, 6H), 0.948(t, 3H, J = 7.6 Hz).<br>$^{13}$C-NMR(CDCl$_3$): 153.900, 148.761, 146.696, 145.202, 144.065, 132.281, 129.525, 129.439, 128.779, 128.446, 127.572, 126.667, 125.683, 123.889, 123.846, 116.445, 116.103, 109.489, 109.227, 76.217, 67.528, 37.349, 27.857, 24.165, 21.605, 13.654. |

TABLE 4-continued

| No. | Chemical structure | $^1$H-NMR, $^{13}$C-NMR (CDCl$_3$, δ) |
|---|---|---|
| Example 40 | 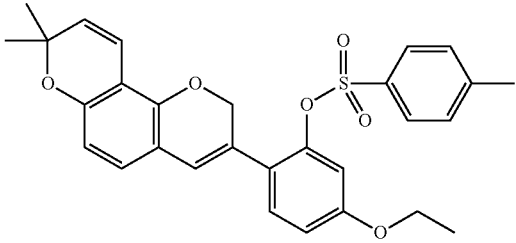<br>(Compound I-a-40) | $^1$H-NMR(CDCl$_3$): 7.546(d, 2H, J = 8.0 Hz), 7.042(d, 1H, J = 8.0 Hz), 7.020(d, 2H, J = 8.0 Hz), 6.943(d, 1H, J = 2.4 Hz), 6.787(dd, 1H, J = 8.0, 2.4 Hz), 6.625(d, 1H, J = 8.0 Hz), 6.602(d, 1H, J = 10.0 Hz), 6.351(d, 1H, J = 8.0 Hz), 5.937(s, 1H), 5.617(d, 1H, J = 10.0 Hz), 4.707(s, 2H), 4.042(q, 2H, J = 6.8 Hz), 2.273(s, 3H), 1.450(s, 6H), 1.429(t, 3H, J = 6.8 Hz).<br>$^{13}$C-NMR(CDCl$_3$): 159.115, 153.775, 148.633, 147.492, 145.304, 132.172, 129.524, 129.465, 128.455, 126.521, 125.478, 124.390, 123.236, 116.461, 116.161, 114.219, 109.834, 109.475, 109.187, 76.185, 67.579, 63.966, 27.849, 21.607, 14.617. |
| Example 41 | 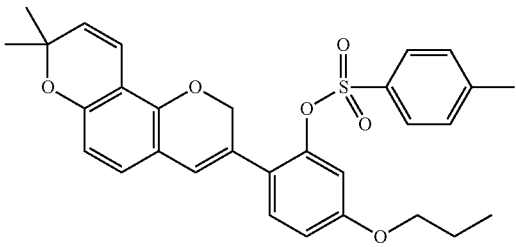<br>(Compound I-a-41) | $^1$H-NMR(CDCl$_3$): 7.551(d, 2H, J = 8.0 Hz), 7.042(d, 1H, J = 8.0 Hz), 7.022(d, 2H, J = 8.0 Hz), 6.936(d, 1H, J = 2.4 Hz), 6.794(dd, 1H, J = 8.0, 2.4 Hz), 6.625(d, 1H, J = 8.0 Hz), 6.602(d, 1H, J = 10.0 Hz), 6.350(d, 1H, J = 8.0 Hz), 5.941(s, 1H), 5.616(d, 1H, J = 10.0 Hz), 4.708(s, 2H), 3.920(t, 2H, J = 6.4 Hz), 2.272(s, 3H), 1.819(m, 2H), 1.449(s, 6H), 1.046(t, 3H, J = 7.6 Hz).<br>$^{13}$C-NMR(CDCl$_3$): 159.301, 153.744, 148.610, 147.462, 145.303, 132.136, 129.498, 129.456, 128.454, 126.507, 125.487, 124.322, 123.190, 116.452, 116.161, 114.236, 109.818, 109.464, 109.175, 76.176, 69.927, 67.570, 27.834, 22.387, 21.602, 10.442. |
| Example 42 | 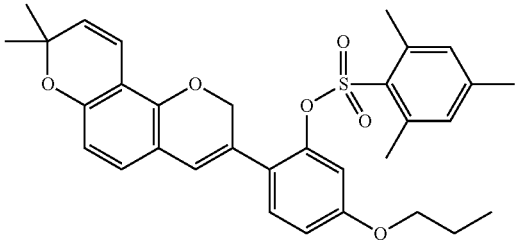<br>(Compound I-a-42) | $^1$H-NMR(CDCl$_3$): 7.119(d, 1H, J = 8.0 Hz), 6.787(m, 1H), 6.785(s, 2H), 6.63~6.68(m, 2H), 6.587(d, 1H, J = 10.0 Hz), 6.332(d, 1H, J = 8.0 Hz), 6.180(s, 1H), 5.602(d, 1H, J = 10.0 Hz), 4.765(s, 2H), 3.817(t, 2H, J = 6.4 Hz), 2.447(s, 6H), 2.180(s, 3H), 1.758(m, 2H), 1.442(s, 6H), 1.006(t, 3H, J = 7.2 Hz).<br>$^{13}$C-NMR(CDCl$_3$): 159.117, 153.685, 148.693, 147.612, 143.784, 140.248, 131.765, 131.454, 129.671, 129.324, 126.718, 125.536, 124.557, 123.119, 116.515, 115.959, 114.058, 109.507, 109.369, 109.032, 76.093, 69.855, 67.793, 27.823, 23.048, 22.325, 21.013, 10.367. |

| No. | Chemical structure | $^1$H-NMR, $^{13}$C-NMR (CDCl$_3$, δ) |
|---|---|---|
| Example 43 | 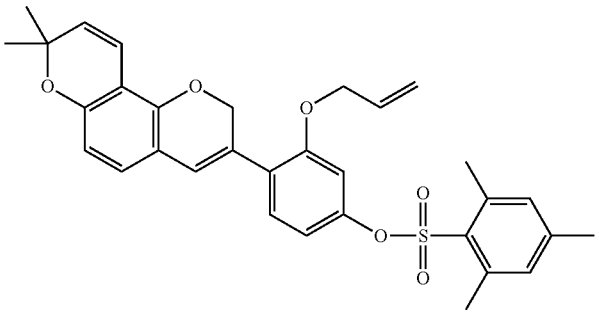<br>(Compound I-a-43) | $^1$H-NMR(CDCl$_3$): 7.162(d, 1H, J = 8.0 Hz), 6.989(s, 2H), 6.818(d, 1H, J = 8.0 Hz), 6.626(d, 1H, J = 10.0 Hz), 6.528(d, 1H, J = 2.0 Hz), 6.511(s, 1H), 6.501(dd, 1H, J = 8.0, 2.0 Hz), 6.371(d, 1H, J = 8.0 Hz), 5.934(m, 1H), 5.588(d, 1H, J = 10.0 Hz), 5.327(m, 1H, J = 17.2 Hz, 1.6 Hz), 5.253(m, 1H, J = 14.8, 1.6 Hz), 4.969(s, 2H), 4.381(m, 2H, J = 5.2, 1.6 Hz), 2.580(s, 6H), 2.329(s, 3H), 1.420(s, 6H).<br>$^{13}$C-NMR(CDCl$_3$): 156.543, 153.818, 149.550, 149.364, 143.871, 140.470, 132.189, 131.753, 130.643, 129.398, 129.020, 127.631, 127.065, 126.838, 123.321, 118.251, 116.521, 116.479, 114.280, 109.575, 109.422, 106.804, 76.165, 69.363, 68.043, 27.844, 22.755, 21.072. |
| Example 44 | 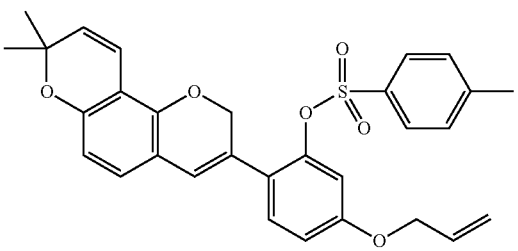<br>(Compound I-a-44) | $^1$H-NMR(CDCl$_3$): 7.543(d, 2H, J = 8.0 Hz), 7.052(d, 1H, J = 8.0 Hz), 7.025(d, 2H, J = 8.0 Hz), 6.963(d, 1H, J = 2.4 Hz), 6.818(dd, 1H, J = 8.0, 2.4 Hz), 6.630(d, 1H, J = 8.0 Hz), 6.601(d, 1H, J = 10.0 Hz), 6.353(d, 1H, J = 8.0 Hz), 6.045(m, 1H), 5.946(s, 1H), 5.617(d, 1H, J = 10.0 Hz), 5.434(m, 1H, J = 17.2 Hz, 1.6 Hz), 5.376(m, 1H, J = 14.8, 1.6Hz), 4.713(s, 2H), 4.544(m, 2H, J = 5.2, 1.6 Hz), 2.276(s, 3H), 1.449(s, 6H).<br>$^{13}$C-NMR(CDCl$_3$): 158.672, 153.796, 148.639, 147.442, 145.329, 132.481, 132.124, 129.546, 129.474, 129.458, 128.454, 126.539, 125.393, 124.751, 123.351, 118.220, 116.441, 116.126, 114.418, 110.139, 109.475, 109.200, 76.191, 69.158, 67.551, 27.844, 21.609. |
| Example 45 | 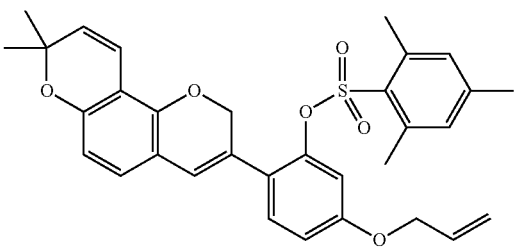<br>(Compound I-a-45) | $^1$H-NMR(CDCl$_3$): 7.128(d, 1H, J = 8.4 Hz), 6.812(dd, 1H, J = 8.4, 2.4 Hz), 6.791(s, 2H), 6.681(d, 1H, J = 2.4 Hz), 6.662(d, 1H, J = 8.4 Hz), 6.588(d, 1H, J = 10.0 Hz), 6.333(d, 1H, J = 8.4 Hz), 6.186(s, 1H), 5.985(m, 1H), 5.601(s, 1H, J = 10.0 Hz), 5.368(m, 1H, J = 17.2 Hz, 1.6 Hz), 5.287(m, 1H, J = 14.8, 1.6 Hz), 4.771(s, 2H), 4.448(m, 1H, J = 2H, J = 5.2, 1.6 Hz), 2.444(s, 6H), 2.185(s, 3H), 1.442(s, 6H).<br>13C-NMR(CDCl$_3$): 158.518, 153.742, 148.727, 147.604, 143.833, 140.268, 132.498, 131.794, 131.426, 129.731, 129.348, 126.758, 125.455, 125.018, 123.273, 118.102, 116.513, 115.943, 114.200, 109.880, 109.392, 109.065, 76.122, 69.078, 67.777, 27.832, 23.048, 21.023. |

TABLE 4-continued

| No. | Chemical structure | $^1$H-NMR, $^{13}$C-NMR (CDCl$_3$, δ) |
|---|---|---|
| Example 46 | 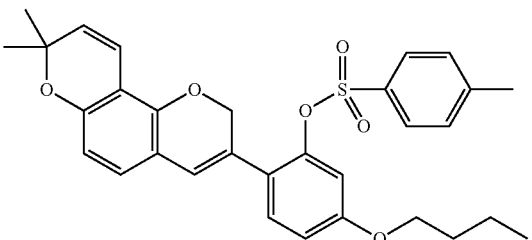<br>(Compound I-a-46) | $^1$H-NMR (CDCl$_3$): 7.552(d, 2H, J = 8.0 Hz), 7.042(d, 1H, J = 8.0 Hz), 7.022(d, 2H, J = 8.0 Hz), 6.931(d, 1H, J = 2.4 Hz), 6.789 (dd, 1H, J = 8.0, 2.4 Hz), 6.625(d, 1H, J = 8.0 Hz), 6.601(d, 1H, J = 10.0 Hz), 6.349(d, 1H, J = 8.0 Hz), 5.945(s, 1H), 5.614(d, 1H, J = 10.0 Hz), 4.709(s, 2H), 3.959(t, 2H, J = 6.4 Hz), 2.273(s, 3H), 1.774(m, 2H), 1.499(m, 2H), 1.448(s, 6H), 0.989 (t, 3H, J = 7.2 Hz).<br>$^{13}$C-NMR(CDCl$_3$): 159.334, 153.764, 148.632, 147.487, 145.299, 132.196, 129.504, 129.464, 128.470, 126.522, 125.508, 124.334, 123.219, 116.464, 116.170, 114.247, 109.824, 109.477, 109.185, 76.186, 68.179, 67.595, 31.094, 27.848, 21.603, 19.162, 13.817. |
| Example 47 | 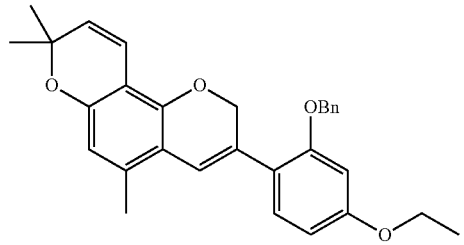<br>(Compound I-a-47) | $^1$H-NMR(CDCl$_3$): 7.29~7.45(m, 5H), 7.251(d, 1H, J = 8.4 Hz), 6.687(d, 1H, J = 8.0 Hz), 6.598(d, 1H, J = 10.0 Hz), 6.542(d, 1H, J = 2.0 Hz), 6.509(dd, 1H, J = 8.4, 2.0 Hz), 6.244(s, 1H), 5.510(d, 1H, J = 10.0 Hz), 5.035(s, 2H), 4.926(s, 2H), 4.025(q, 2H, J = 6.8 Hz), 2.206(s, 3H), 1.408(t, 3H, J = 6.8 Hz), 1.402(s, 6H).<br>$^{13}$C-NMR(CDCl$_3$): 159.787, 157.312, 152.757, 149.379, 136.481, 134.884, 129.198, 128.588, 128.214, 128.026, 128.003, 127.527, 121.428, 118.980, 116.758, 115.624, 110.796, 107.503, 105.609, 100.286, 76.000, 70.387, 68.069, 63.599, 27.859, 18.734, 14.787. |
| Example 48 | 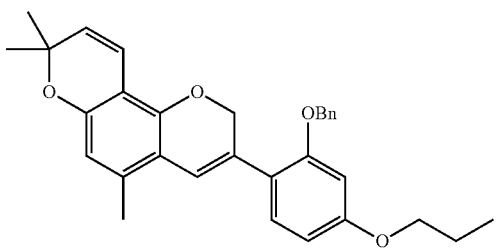<br>(Compound I-a-48) | $^1$H-NMR(CDCl$_3$): 7.29~7.45(m, 5H), 7.253(d, 1H, J = 8.4 Hz), 6.685(d, 1H, J = 8.0 Hz), 6.597(d, 1H, J = 10.0 Hz), 6.540(d, 1H, J = 2.0 Hz), 6.506(dd, 1H, J = 8.4, 2.0 Hz), 6.245(s, 1H), 5.511(d, 1H, J = 10.0 Hz), 5.038(s, 2H), 4.923(s, 2H), 3.918(t, 2H, J = 6.8 Hz), 2.207(s, 3H), 1.804(m, 2H, J = 6.8 Hz), 1.402(s, 6H), 1.037(t, 3H, J = 7.2 Hz).<br>$^{13}$C-NMR(CDCl$_3$): 160.015, 157.339, 152.768, 149.394, 136.516, 134.887, 129.196, 128.588, 128.212, 128.049, 128.005, 127.553, 121.404, 118.975, 116.775, 115.638, 110.803, 107.510, 105.733, 100.320, 76.005, 70.432, 68.093, 64.405, 27.873, 22.546, 18.726, 10.509. |
| Example 49 | 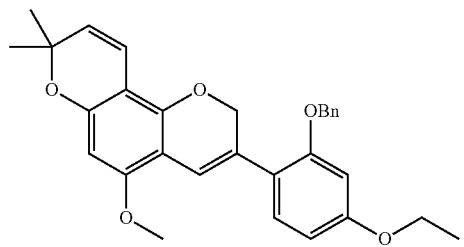<br>(Compound I-a-49) | $^1$H-NMR(CDCl$_3$): 7.29~7.48(m, 5H), 7.269(d, 1H, J = 8.4 Hz), 6.824(s, 1H), 6.553(d, 1H, J = 10.0 Hz), 6.513(d, 1H, J = 2.0 Hz), 6.489(dd, 1H, J = 8.4, 2.0 Hz), 6.011(s, 1H), 5.431(d, 1H, J = 10.0 Hz), 5.028(s, 2H), 4.941(s, 2H), 4.015(q, 2H, J = 6.8 Hz), 3.776(s, 3H), 1.415(s, 6H), 1.401(t, 3H, J = 6.8 Hz).<br>$^{13}$C-NMR(CDCl$_3$): 159.676, 157.284, 155.986, 154.098, 150.056, 136.637, 129.408, 128.549, 127.899, 127.423, 126.678, 126.154, 121.687, 116.663, |

| No. | Chemical structure | $^1$H-NMR, $^{13}$C-NMR (CDCl$_3$, δ) |
|---|---|---|
| | | 116.373, 106.515, 105.675, 103.168, 100.316, 92.899, 76.547, 70.380, 68.433, 63.576, 55.556, 27.880, 14.798. |
| Example 50 | 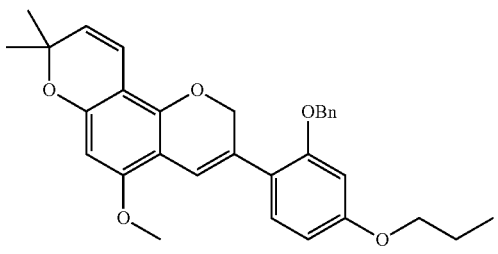<br>(Compound I-a-50) | $^1$H-NMR(CDCl$_3$): 7.29~7.48(m, 5H), 7.266(d, 1H, J = 8.4 Hz), 6.825(s, 1H), 6.553(d, 1H, J = 10.0 Hz), 6.522(d, 1H, J = 2.4 Hz), 6.496(dd, 1H, J = 8.4, 2.4 Hz), 6.010(s, 1H), 5.427(d, 1H, J = 10.0 Hz), 5.025(s, 2H), 4.940(s, 2H), 3.900(t, 2H, J = 6.8 Hz), 3.772(s, 3H), 1.791(m, 2H, J = 6.8 Hz), 1.413(s, 6H), 1.046(t, 3H, J = 6.8 Hz).<br>$^{13}$C-NMR(CDCl$_3$): 159.876, 157.271, 155.967, 154.077, 150.038, 136.626, 129.378, 128.527, 127.883, 127.430, 126.679, 126.134, 121.603, 116.654, 116.325, 106.506, 105.717, 103.151, 100.276, 92.880, 76.526, 70.367, 69.626, 68.428, 55.534, 27.863, 22.541, 10.502. |
| Example 51 | 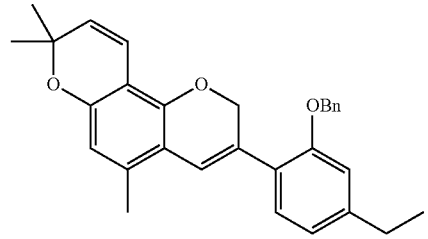<br>(Compound I-a-51) | $^1$H-NMR(CDCl$_3$): 7.29~7.45(m, 5H), 7.270(d, 1H, J = 8.0 Hz), 6.838(d, 1H, J = 8.0 Hz), 6.814(s, 1H), 6.734(s, 1H), 6.599(d, 1H, J = 10.0 Hz), 6.247(s, 1H), 5.509(d, 1H, J = 10.0 Hz), 5.063(s, 2H), 4.943(s, 2H), 2.630(q, 2H, J = 7.6 Hz), 2.207(s, 3H), 1.402(s, 6H), 1.244(t, 3H, J = 7.6 Hz).<br>$^{13}$C-NMR(CDCl$_3$): 154.431, 153.000, 149.650, 145.470, 137.004, 135.040, 128.637, 128.579, 128.313, 128.239, 127.965, 127.583, 126.092, 120.617, 119.729, 116.775, 115.607, 111.892, 110.873, 107.544, 76.049, 70.396, 68.051, 28.925, 27.886, 18.744, 15.559. |
| Example 52 | 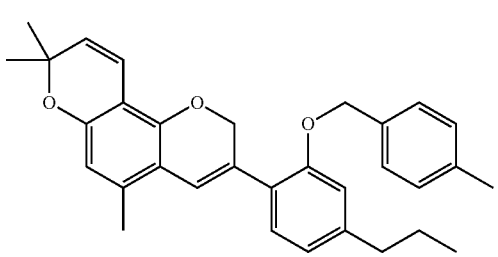<br>(Compound I-a-52) | $^1$H-NMR(CDCl$_3$): 7.294(d, 2H, J = 8.0 Hz), 7.252(d, 1H, J = 9.2 Hz), 7.169(d, 2H, J = 8.0 Hz), 6.801(d, 1H, J = 9.2 Hz), 6.794(s, 1H), 6.599(d, 1H, J = 10.0 Hz), 6.243(s, 1H), 5.512(d, 1H, J = 10.0 Hz), 5.011(s, 2H), 4.928(s, 2H), 2.584(t, 2H, J = 7.6 Hz), 2.349(s, 3H), 2.208(s, 3H), 1.660(m, 2H, J = 7.6 Hz), 1.403(s, 6H), 0.954(t, 3H, J = 7.6 Hz).<br>$^{13}$C-NMR(CDCl$_3$): 156.315, 152.861, 149.545, 143.872, 137.691, 135.012, 133.692, 129.223, 128.443, 128.414, 128.191, 127.707, 126.075, 121.169, 119.601, 116.785, 115.630, 112.406, 110.794, 107.510, 76.021, 70.292, 68.053, 38.082, 27.886, 24.504, 21.181, 18.726, 13.852. |

| No. | Chemical structure | $^1$H-NMR, $^{13}$C-NMR (CDCl$_3$, δ) |
|---|---|---|
| Example 53 | 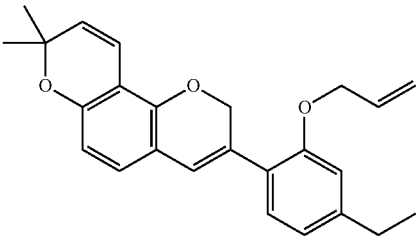<br>(Compound I-a-53) | $^1$H-NMR(CDCl$_3$): 7.231(d, 1H, J = 8.0 Hz), 6.832(d, 1H, J = 8.0 Hz), 6.811(d, 1H, J = 8.0 Hz), 6.718(s, 1H), 6.656(d, 1H, J = 10.0 Hz), 6.542(s, 1H), 6.375(d, 1H, J = 8.0 Hz), 6.037(m, 1H), 5.588(d, 1H, J = 10.0 Hz), 5.395(m, 1H, J = 17.6 Hz, 1.6 Hz), 5.266(m, 1H, J = 9.2 Hz, 1.4 Hz), 5.050(s, 2H), 4.552(m, 2H), 2.639(q, 2H, J = 7.6 Hz), 1.425(s, 6H), 1.244(t, 3H, J = 7.6 Hz).<br>$^{13}$C-NMR(CDCl$_3$): 156.148, 153.464, 149.310, 145.475, 133.165, 129.285, 129.091, 128.681, 126.627, 125.671, 122.101, 120.537, 117.621, 116.929, 116.669, 111.934, 109.581, 109.241, 76.060, 69.182, 68.441, 28.887, 27.822, 15.484. |
| Example 54 | 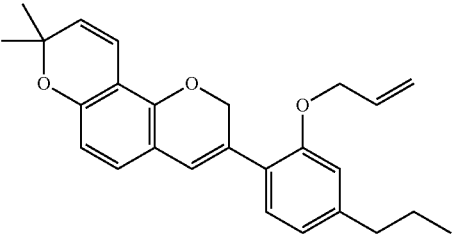<br>(Compound I-a-54) | $^1$H-NMR(CDCl$_3$): 7.219(d, 1H, J = 8.0 Hz), 6.830(d, 1H, J = 8.0 Hz), 6.786(d, 1H, J = 8.0, 1.2 Hz), 6.693(d, 1H, J = 1.2 Hz), 6.655(d, 1H, J = 10.0 Hz), 6.544(s, 1H), 6.373(d, 1H, J = 8.0 Hz), 6.038(m, 1H), 5.588(d, 1H, J = 10.0 Hz), 5.391(m, 1H, J = 17.6 Hz, 1.6 Hz), 5.261(m, 1H, J = 9.2, 1.4 Hz), 5.049(s, 2H), 4.545(m, 2H), 2.570(t, 2H, J = 7.6 Hz), 1.645(m, 2H), 1.424(s, 6H), 0.955(t, 3H, J = 7.6 Hz).<br>$^{13}$C-NMR(CDCl$_3$): 156.052, 153.450, 149.311, 143.924, 133.160, 129.277, 129.102, 128.548, 126.622, 125.646, 122.087, 121.192, 117.609, 116.940, 116.671, 112.491, 109.576, 109.233, 76.053, 69.170, 68.440, 38.062, 27.820, 24.473, 13.859. |
| Example 55 | 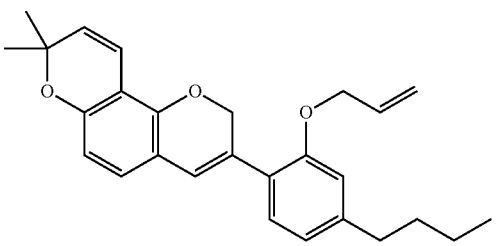<br>(Compound I-a-55) | $^1$H-NMR (CDCl$_3$): 7.212(d, 1H, J = 8.0 Hz), 6.823(d, 1H, J = 8.0 Hz), 6.782(d, 1H, J = 8.0, 1.2 Hz), 6.691(d, 1H, J = 1.2 Hz), 6.654(d, 1H, J = 10.0 Hz), 6.540(s, 1H), 6.371(d, 1H, J = 8.0 Hz), 6.032(m, 1H), 5.581(d, 1H, J = 10.0 Hz), 5.387(m, 1H, J = 17.6 Hz, 1.6 Hz), 5.255(m, 1H, J = 9.2, 1.4 Hz), 5.047(s, 2H), 4.533(m, 2H), 2.588(t, 2H, J = 7.6 Hz), 1.598 (m, 2H), 1.419(s, 6H), 1.372(m, 2H), 0.932 (t, 3H, J = 7.6 Hz).<br>$^{13}$C-NMR (CDCl$_3$): 155.791, 153.435, 149.293, 144.111, 133.149, 129.238, 129.072, 128.529, 126.603, 125.586, 122.055, 121.128, 117.564, 116.922, 116.658, 112.450, 109.551, 109.213, 76.031, 69.156, 68.421, 35.653, 33.457, 27.799, 22.348, 13.836. |

TABLE 4-continued

| No. | Chemical structure | $^{1}$H-NMR, $^{13}$C-NMR (CDCl$_3$, δ) |
|---|---|---|
| Example 56 | 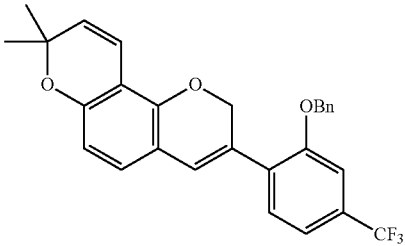<br>(Compound I-a-56) | $^{1}$H-NMR(CDCl$_3$): 7.30~7.45(m, 6H), 7.244(dd, 1H, J = 0.8, 8.0 Hz), 7.172(s, 1H), 6.841(d, 1H, J = 8.4 Hz), 6.636(s, 1H), 6.612(d, 1H, J = 10.0 Hz), 6.385(d, 1H, J = 8.4 Hz), 5.586(d, 1H, J = 10.0 Hz), 5.100(s, 2H), 4.981(d, 2H, J = 0.8 Hz), 1.422(s, 6H).<br>$^{13}$C-NMR(CDCl$_3$): 156.314, 154.107, 149.585, 135.777, 131.971, 130.620, 129.432, 129.067, 128.729, 128.319, 128.010, 127.618, 127.303, 127.103, 124.433, 123.951, 118.106, 116.427, 109.602, 109.551, 108.878, 76.265, 70.806, 67.980, 27.893. |
| Example 57 | 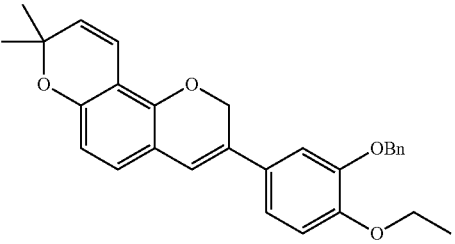<br>(Compound I-a-57) | $^{1}$H-NMR(CDCl$_3$): 7.24~7.48(m, 5H), 6.995(d, 1H, J = 2.0 Hz), 6.920(dd, 1H, J = 2.0, 8.4 Hz), 6.871(d, 1H, J = 8.4 Hz), 6.808(d, 1H, J = 8.4 Hz), 6.640(d, 1H, J = 10.0 Hz), 6.555(s, 1H), 6.368(d, 1H, J = 8.4 Hz), 5.594(d, 1H, J = 10.0 Hz), 5.167(s, 2H), 5.050(s, 2H), 4.111(q, 2H, J = 6.8 Hz), 1.455(t, 3H, J = 6.8 Hz), 1.421(s, 6H).<br>$^{13}$C-NMR(CDCl$_3$): 153.519, 149.132, 148.651, 148.586, 137.255, 129.896, 129.457, 128.484, 127.875, 127.827, 127.324, 126.594, 118.720, 117.978, 116.441, 116.132, 113.526, 111.962, 109.446, 109.321, 76.108, 71.596, 67.248, 64.607, 27.842, 14.870. |
| Example 58 | 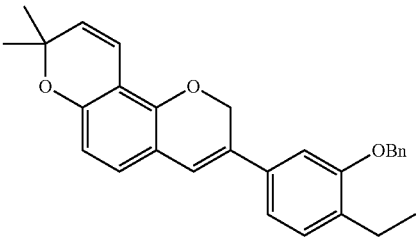<br>(Compound I-a-58) | $^{1}$H-NMR(CDCl$_3$): 7.29~7.48(m, 5H), 7.159(d, 1H, J = 8.4 Hz), 6.945(d, 1H, J = 1.6 Hz), 6.920(dd, 1H, J = 1.6, 8.4 Hz), 6.836(d, 1H, J = 8.0 Hz), 6.661(s, 1H), 6.647(d, 1H, J = 8.4 Hz), 6.649(d, 1H, J = 10.0 Hz), 6.380(d, 1H, J = 8.0 Hz), 5.597(d, 1H, J = 10.0 Hz), 5.116(s, 2H), 5.106(s, 2H), 2.705(q, 2H, J = 7.6 Hz), 1.425(s, 6H), 1.223(t, 3H, J = 7.6 Hz).<br>$^{13}$C-NMR(CDCl$_3$): 156.667, 153.700, 148.867, 137.295, 135.822, 132.891, 129.476, 129.181, 128.545, 128.394, 127.805, 127.102, 126.770, 119.642, 117.076, 116.436, 116.084, 109.486, 109.373, 107.886, 76.151, 69.916, 67.394, 27.861, 23.215, 14.150. |
| Example 59 | 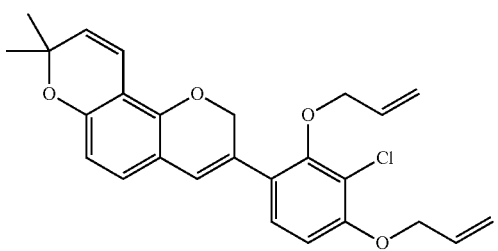<br>(Compound I-a-59) | $^{1}$H-NMR (CDCl$_3$): 7.144(d, 1H, J = 8.8 Hz), 6.838(d, 1H, J = 8.0 Hz), 6.721(d, 1H, J = 8.8 Hz), 6.653(d, 1H, J = 10.0 Hz), 6.576(t, 1H, J = 1.2 Hz), 6.389(d, 1H, J = 8.0 Hz), 6.016.13(m, 2H), 5.603(d, 1H, J = 10.0 Hz), 5.480(m, 1H, J = 1.6, 17.2 Hz), 5.351(m, 1H, J = 1.6, 17.2 Hz), 5.328(m, 1H, J = 1.6, 10.8 Hz), 5.218(m, 1H, J = 1.6, 10.8 Hz), 5.018(d, 2H, J = 1.2 Hz), 4.625(m, 2H, J = 1.6, 5.2 Hz), 4.414(m, 2H, J = 1.6, 5.2 Hz), 1.433(s, 6H).<br>$^{13}$C-NMR (CDCl$_3$): 154.827, 153.835, 153.607, 149.272, 133.191, 132.470, 129.437, 127.462, 126.809, 126.763, 126.641, |

TABLE 4-continued

| No. | Chemical structure | $^1$H-NMR, $^{13}$C-NMR (CDCl$_3$, δ) |
|---|---|---|
| | | 122.920, 118.471, 118.020, 117.759, 116.508, 116.450, 109.635, 109.388, 109.189, 76.218, 74.134, 69.905, 68.055, 27.900. |
| Example 60 | 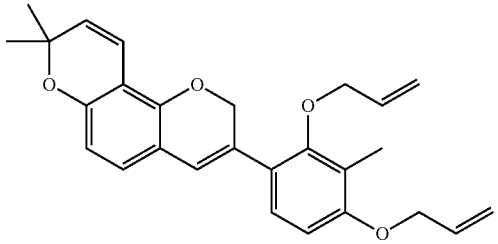<br>(Compound I-a-60) | $^1$H-NMR(CDCl$_3$): 7.085(d, 1H, J = 8.4 Hz), 6.827(d, 1H, J = 8.4 Hz), 6.660(d, 1H, J = 10.0 Hz), 6.628(d, 1H, J = 8.4 Hz), 6.554(s, 1H), 6.380(d, 1H, J = 8.4 Hz), 5.7~6.2(m, 2H), 5.593(d, 1H, J = 10.0 Hz), 5.434(dd, 1H, J = 1.6, 17.2 Hz), 5.350(dd, 1H, J = 1.6, 17.2 Hz), 5.285(dd, 1H, J = 1.6, 10.8 Hz), 5.200(dd, 1H, J = 1.6, 10.8 Hz), 5.031(s, 2H), 4.545(d, 2H, J = 4.8 Hz), 4.262(d, 2H, J = 5.2 Hz), 2.188(s, 3H), 1.430(s, 6H).<br>$^{13}$C-NMR(CDCl$_3$): 157.435, 155.623, 153.493, 149.206, 133.722, 133.339, 129.322, 128.803, 126.529, 126.119, 125.208, 121.783, 120.622, 117.537, 117.116, 116.792, 116.614, 109.595, 109.218, 107.505, 76.101, 73.760, 69.001, 68.298, 27.866, 9.239. |
| Example 61 | 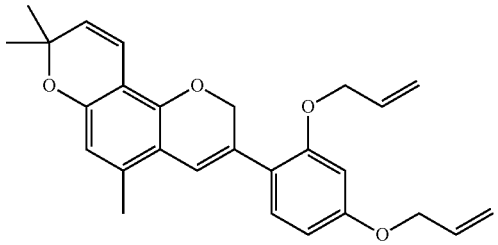<br>(Compound I-a-62) | $^1$H-NMR(CDCl$_3$): 7.242(d, 1H, J = 8.0 Hz), 6.664(s, 1H), 6.626(d, 1H, J = 10.0 Hz), 6.511(d, 1H, J = 8.0 Hz), 6.489(s, 1H), 6.263(s, 1H), 5.99~6.10(m, 2H), 5.529(d, 1H, J = 10.0 Hz), 5.431(d, 1H, J = 11.2 Hz), 5.388(d, 1H, J = 11.2 Hz), 5.301(d, 1H, J = 11.6 Hz), 5.272(d, 1H, J = 11.6 Hz), 4.964(s, 2H), 4.50-4.55(m, 4H), 2.258(s, 3H), 1.413(s, 6H).<br>$^{13}$C-NMR(CDCl$_3$): 159.421, 157.138, 149.410, 134.858, 133.097, 132.850, 129.206, 128.309, 128.264, 121.730, 118.985, 117.849, 116.781, 115.606, 110.848, 107.573, 105.866, 100.458, 76.011, 69.177, 68.967, 68.033, 27.851, 18.771. |
| Example 62 | 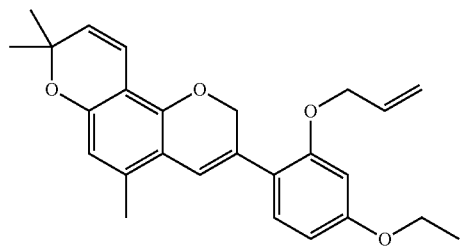<br>(Compound I-a-65) | $^1$H-NMR(CDCl$_3$): 7.241(d, 1H, J = 8.0 Hz), 6.662(s, 1H), 6.628(d, 1H, J = 10.0 Hz), 6.496(dd, 1H, J = 8.0, 2.0 Hz), 6.453(d, 1H, J = 2.0 Hz), 6.263(s, 1H), 6.032(m, 1H), 5.530(d, 1H, J = 10.0 Hz), 5.395(dd, 1H, J = 17.6, 1.2 Hz), 5.271(dd, 1H, J = 10.4, 1.2 Hz), 4.966(s, 2H), 4.516(d, 2H, J = 5.2 Hz), 4.032(q, 2H, J = 7.2 Hz), 2.259(s, 3H), 1.418(t, 3H, J = 7.2 Hz), 1.413(s, 6H).<br>$^{13}$C-NMR(CDCl$_3$): 159.802, 157.146, 152.766, 149.396, 134.837, 132.896, 129.235, 128.392, 128.254, 121.433, 118.866, 117.813, 116.790, 115.631, 110.837, 107.569, 105.575, 100.214, 76.003, 69.155, 68.062, 63.594, 27.848, 18.762, 14.801. |

TABLE 4-continued

| No. | Chemical structure | ¹H-NMR, ¹³C-NMR (CDCl₃, δ) |
|---|---|---|
| Example 63 | 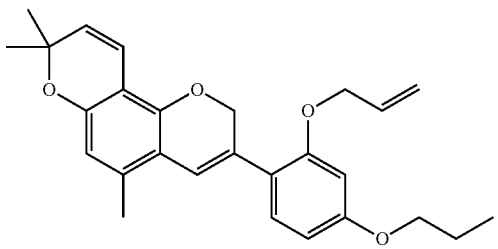<br>(Compound I-a-66) | ¹H-NMR(CDCl₃): 7.240(d, 1H, J = 8.4 Hz), 6.659(s, 1H), 6.628(d, 1H, J = 10.0 Hz), 6.501(dd, 1H, J = 8.4, 2.4 Hz), 6.459(d, 1H, J = 2.4 Hz), 6.263(s, 1H), 6.035(m, 1H), 5.529(d, 1H, J = 10.0 Hz), 5.396(m, 1H, J = 17.2, 1.6 Hz), 5.269(dd, 1H, J = 10.4, 1.2 Hz), 4.965(s, 2H), 4.519(m, 2H, J = 5.2, 1.2 Hz), 3.920(t, 2H, J = 6.8 Hz), 2.259(s, 3H), 1.811(m, 2H), 1.413(s, 6H), 1.041(t, 3H, J = 7.2 Hz).<br>¹³C-NMR(CDCl₃): 160.028, 157.159, 152.774, 149.400, 134.827, 132.921, 129.220, 128.412, 128.246, 121.389, 118.846, 117.793, 116.801, 115.635, 110.836, 107.570, 105.683, 100.227, 75.998, 69.664, 69.179, 68.079, 27.854, 22.560, 18.762, 10.508. |

Example 64: Synthesis of 3-(allyloxy)-4-(8,8-dimethyl-2,8,9,10-tetrahydropyrano[2,3-f]chromen-3-yl)phenyl 2,4,6-trimethylbenzenesulfonate (Compound I-b-43)

64-1: Preparation of 3-(benzyloxy)-4-(2-((6-formyl-2,2-dimethyl-2H-chromen-5-yl)oxy)acetyl)phenyl 2,4,6-trimethylbenzenesulfonate 82.6 g (0.131 mol) of 3-(benzyloxy)-4-(2-((6-formyl-2,2-dimethyl-2H-chromen-5-yl)oxy)acetyl)phenyl 2,4,6-trimethylbenzenesulfonate was obtained by using the same method as in Example 1-1, except that 133.5 g (0.265 mol) of 3-(benzyloxy)-4-(2-bromoacetyl)phenyl 2,4,6-trimethylbenzenesulfonate was used instead of 1-(2,4-bis(allyloxy)phenyl)-2-bromoethanone in Example 1-1 (Yield: 49.6%).

¹H-NMR (CDCl₃): 10.085 (s, 1H), 7.914 (d, 1H, J=8.8 Hz), 7.596 (d, 1H, J=8.8 Hz), 7.26-7.32 (m, 5H), 6.989 (s, 2H), 6.813 (d, 1H, J=2.0 Hz), 6.636 (d, 1H, J=8.8 Hz), 6.540 (dd, 1H, J=8.8, 2.0 Hz), 6.535 (d, 1H, J=10.0 Hz), 5.574 (d, 1H, J=10.0 Hz), 5.079 (s, 2H), 4.986 (s, 2H), 2.557 (s, 6H), 2.329 (s, 3H), 1.409 (s, 6H).

¹³C-NMR (CDCl₃): 192.772, 188.435, 159.612, 159.183, 158.038, 154.157, 144.331, 140.420, 134.526, 132.448, 131.905, 130.521, 130.412, 130.244, 128.787, 127.839, 123.220, 122.421, 115.952, 114.582, 114.225, 113.325, 107.413, 81.715, 77.404, 71.445, 28.129, 22.734, 21.109.

64-2: Preparation of 3-(benzyloxy)-4-(3-hydroxy-8,8-dimethyl-4-oxo-2,3,4,8-tetrahydropyrano[2,3-f]chromen-3-yl)phenyl 2,4,6-trimethylbenzenesulfonate 72.6 g (0.116 mol) of the 3-(benzyloxy)-4-(3-hydroxy-8,8-dimethyl-4-oxo-2,3,4,8-tetrahydropyrano[2,3-f]chromen-3-yl)phenyl 2,4,6-trimethylbenzenesulfonate was obtained by allowing 82.6 g (0.131 mol) of the 3-(benzyloxy)-4-(2-((6-formyl-2,2-dimethyl-2H-chromen-5-yl)oxy)acetyl)phenyl 2,4,6-trimethylbenzenesulfonate obtained in Example 64-1 to react using the same method as in Example 2-2 (Yield: 89.2%).

¹H-NMR (CDCl₃): 7.618 (d, 1H, J=8.8 Hz), 7.457 (d, 1H, J=8.4 Hz), 7.18-7.26 (m, 5H), 6.970 (s, 2H), 6.636 (d, 1H, J=2.0 Hz), 6.556 (d, 1H, J=10.0 Hz), 6.518 (dd, 1H, J=8.8, 2.0 Hz), 6.425 (d, 1H, J=8.4 Hz), 5.569 (d, 1H, J=10.0 Hz), 4.838 (s, 2H), 4.820 (d, 1H, J=12.0 Hz), 4.238 (d, 1H, J=12.0 Hz), 3.511 (s, 1H), 2.543 (s, 6H), 2.323 (s, 3H), 1.452 (s, 3H), 1.436 (s, 3H).

¹³C-NMR (CDCl₃): 189.937, 159.572, 156.977, 156.266, 150.407, 143.897, 140.439, 135.291, 131.771, 130.626, 128.826, 128.787, 128.635, 128.453, 128.055, 127.369, 126.056, 115.611, 114.137, 113.322, 111.618, 109.139, 107.382, 77.603, 77.203, 74.212, 73.698, 70.959, 28.257, 28.183, 22.675, 21.089.

64-3: Preparation of 3-hydroxy-4-(3-hydroxy-8,8-dimethyl-4-oxo-2,3,4,8,9,10-hexahydropyrano[2,3-f]chromen-3-yl)phenyl 2,4,6-trimethylbenzenesulfonate 72.6 g (0.116 mol) of the 3-(benzyloxy)-4-(3-hydroxy-8,8-dimethyl-4-oxo-2,3,4,8-tetrahydropyrano[2,3-f]chromen-3-yl)phenyl 2,4,6-trimethylbenzenesulfonate obtained in Example 64-2 was dissolved in 300 ml of THF, 2.1 g of Pd/C was added thereto, and then the resulting mixture was vigorously stirred at room temperature under 2 atm of hydrogen for 24 hours. Solid components were removed from the reactant by column, and then recrystallized with 500 ml of ethyl acetate to obtain 48.3 g (0.089 mol) of 3-hydroxy-4-(3-hydroxy-8,8-dimethyl-4-oxo-2,3,4,8,9,10-hexahydropyrano[2,3-f]chromen-3-yl)phenyl 2,4,6-trimethylbenzenesulfonate (Yield: 78%).

¹H-NMR (CDCl₃): 8.434 (b, 1H), 7.738 (d, 1H, J=8.8 Hz), 6.951 (s, 2H), 6.760 (d, 1H, J=8.8 Hz), 6.569 (d, 1H, J=2.4 Hz), 6.554 (d, 1H, J=8.8 Hz), 6.407 (dd, 1H, J=8.8, 2.4 Hz), 4.807 (d, 1H, J=11.2 Hz), 4.521 (s, 1H), 4.339 (d, 1H, J=11.2 Hz), 2.605 (m, 2H), 2.550 (s, 6H), 2.307 (s, 3H), 1.782 (m, 2H), 1.359 (s, 3H), 1.351 (s, 3H).

¹³C-NMR (CDCl₃): 190.919, 162.291, 161.380, 157.453, 150.566, 143.839, 140.236, 131.834, 131.797, 127.358, 126.458, 122.219, 113.397, 112.077, 111.729, 109.357, 76.279, 74.006, 73.306, 31.448, 26.896, 26.591, 22.659, 21.092, 16.258.

64-4: Preparation of 3-(allyloxy)-4-(3-hydroxy-8,8-dimethyl-4-oxo-2,3,4,8,9,10-hexahydropyrano[2,3-f]chromen-3-yl)phenyl 2,4,6-trimethylbenzenesulfonate After 48.3 g (0.089 mol) of the 3-hydroxy-4-(3-hydroxy-8,8-dimethyl-4-oxo-2,3,4,8,9,10-hexahydropyrano[2,3-f]chromen-3-yl)phenyl 2,4,6-trimethylbenzenesulfonate obtained in Example 64-3 was dissolved in 600 ml of acetone, 20 g (0.145 mol) of potassium carbonate ($K_2CO_3$) was added to the solution, 18.4 g (0.152 mol) of 3-bromo-1-propene was slowly dropped and added dropwise, and then the resulting mixture was vigorously refluxed and stirred for 18 hours. After solid components were removed by filtering the reactant, the residue was concentrated and 300 ml of methylene chloride and 300 ml of water were introduced thereinto, the resulting mixture was shaken, the solvent was concentrated by separating the layers to take the methylene chloride layer, and then recrystallized with 300 ml of hexane to obtain 47.6 g (0.082 mol) of 3-(allyloxy)-4-(3-hydroxy-8,8-dimethyl-4-oxo-2,3,4,8,9,10-hexahydropyrano[2,3-f]chromen-3-yl)phenyl 2,4,6-trimethylbenzenesulfonate (Yield: 91.8%).

$^1$H-NMR (CDCl$_3$): 7.685 (d, 1H, J=8.8 Hz), 7.403 (d, 1H, J=8.4 Hz), 6.970 (s, 2H), 6.551 (d, 1H, J=2.0 Hz), 6.497 (d, 1H, J=8.4 Hz), 6.496 (d, 1H, J=8.8 Hz), 5.71-5.81 (m, 1H), 5.201 (dd, 1H, J=1.6, 17.2 Hz), 5.136 (dd, 1H, J=1.2, 10.8 Hz), 4.874 (d, 1H, J=11.8 Hz), 4.331 (m, 1H), 4.263 (d, 1H, J=11.8 Hz), 3.581 (s, 1H), 2.629 (t, 2H, J=6.8 Hz), 2.550 (s, 6H), 2.318 (s, 3H), 1.782 (t, 2H, J=6.8 Hz), 1.349 (s, 3H), 1.332 (s, 3H).

$^{13}$C-NMR (CDCl$_3$): 190.364, 160.743, 160.173, 156.383, 150.290, 143.894, 140.429, 131.910, 131.765, 130.597, 128.599, 126.686, 126.310, 118.081, 114.099, 112.499, 112.176, 108.928, 107.598, 75.619, 73.989, 73.592, 69.800, 31.663, 26.928, 26.503, 22.679, 21.063, 16.461.

64-5: Preparation of 3-(allyloxy)-4-(8,8-dimethyl-2,8,9,10-tetrahydropyrano[2,3-f]chromen-3-yl)phenyl 2,4,6-trimethylbenzenesulfonate 28.3 g (0.052 mol) of 3-(allyloxy)-4-(8,8-dimethyl-2,8,9,10-tetrahydropyrano[2,3-f]chromen-3-yl)phenyl 2,4,6-trimethylbenzenesulfonate was obtained by allowing 47.6 g (0.082 mol) of the 3-(allyloxy)-4-(3-hydroxy-8,8-dimethyl-4-oxo-2,3,4,8,9,10-hexahydropyrano[2,3-f]chromen-3-yl)phenyl 2,4,6-trimethylbenzenesulfonate obtained in Example 64-4 to react using the method as in Example 1-3 (Yield: 63%).

$^1$H-NMR (CDCl$_3$): 7.166 (d, 1H, J=8.4 Hz), 6.993 (s, 2H), 6.835 (d, 1H, J=8.4 Hz), 6.533 (d, 1H, J=2.0 Hz), 6.531 (s, 1H), 6.496 (dd, 1H, J=2.0, 8.4 Hz), 6.383 (d, 1H, J=8.4 Hz), 5.89-5.99 (m, 1H), 5.333 (dd, 1H, J=1.6, 17.2 Hz), 5.253 (dd, 1H, J=1.6, 10.4 Hz), 4.978 (s, 1H), 4.387 (m, 2H), 2.660 (t, 2H, J=6.8 Hz), 2.584 (s, 6H), 2.334 (s, 3H), 1.780 (t, 2H, J=6.8 Hz), 1.328 (s, 6H).

$^{13}$C-NMR (CDCl$_3$): 156.532, 155.059, 151.969, 149.435, 143.855, 140.475, 132.233, 131.748, 130.631, 128.979, 127.259, 126.825, 125.296, 123.562, 118.180, 115.139, 114.247, 110.121, 109.121, 106.795, 74.273, 69.923, 68.006, 32.065, 26.674, 22.761, 21.075, 16.912.

Examples 65 to 68

The 3-phenyl-2,8-dihydropyrano[2,3-f]chromene derivative of Formula (I-b) was synthesized in the same manner as in Example 64, except that a compound shown in the following Table 5 was used as the compound represented by Formula 1 and a compound shown in the following Table 5 was used as the compound represented by Formula 2.

TABLE 5

| No. | Compound represented by Formula 1 | Compound represented by Formula 2 |
| --- | --- | --- |
| Example 65 | 5-hydroxy-2,2-dimethyl-2H-chromene-6-carbaldehyde | 1-(2-(benzyloxy)-4-methoxyphenyl)-2-bromoethanone |
| Example 66 | 5-hydroxy-2,2-dimethyl-2H-chromene-6-carbaldehyde | 1-(2-(benzyloxy)-4-ethoxyphenyl)-2-bromoethanone |
| Example 67 | 5-hydroxy-2,2-dimethyl-2H-chromene-6-carbaldehyde | 1-(2-(benzyloxy)-4-propoxyphenyl)-2-bromoethanone |
| Example 68 | 5-hydroxy-2,2-dimethyl-2H-chromene-6-carbaldehyde | 1-(2-(benzyloxy)-4-ethylphenyl)-2-bromoethanone |

H-NMR data and C-NMR data of the compounds prepared in Examples 64 to 68 and represented by Formula 4-b are shown in the following Table 6.

TABLE 6

| No. | Chemical structure | $^1$H-NMR, $^{13}$C-NMR (CDCl$_3$, δ) |
| --- | --- | --- |
| Example 64 | (Compound 4-b-43) | $^1$H-NMR(CDCl$_3$): 7.685 (d, 1H, J = 8.8 Hz), 7.403 (d, 1H, J = 8.4 Hz), 6.970 (s, 2H), 6.551 (d, 1H, J = 2.0 Hz), 6.497 (d, 1H, J = 8.4 Hz), 6.496 (d, 1H, J = 8.8 Hz), 5.71~5.81 (m, 1H), 5.201 (dd, 1H, J = 1.6, 17.2 Hz), 5.136 (dd, 1H, J = 1.2, 10.8 Hz), 4.874 (d, 1H, J = 11.8 Hz), 4.331 (m, 1H), 4.263 (d, 1H, J = 11.8 Hz), 3.581 (s, 1H), 2.629 (t, 2H, J = 6.8 Hz), 2.550 (s, 6H), 2.318 (s, 3H), 1.782 (t, 2H, J = 6.8 Hz), 1.349 (s, 3H), 1.332 (s, 3H). $^{13}$C-NMR (CDCl$_3$): 190.364, 160.743, 160.173, 153.383, 150.290, 143.894, 140.429, 131.910, 131.765, 130.597, 128.599, 126.686, 126.310, 118.081, |

TABLE 6-continued

| No. | Chemical structure | $^1$H-NMR, $^{13}$C-NMR (CDCl$_3$, δ) |
|---|---|---|
| | | 114.099, 112.499, 112.176, 108.928, 107.598, 75.619, 73.989, 73.592, 69.800, 31.663, 26.928, 26.503, 22.679, 21.063, 16.461. |
| Example 65 | 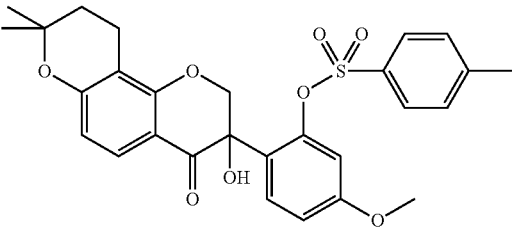<br>(Compound 4-b-37) | $^1$H-NMR(CDCl$_3$): 7.945 (d, 2H, J = 8.0 Hz), 7.378 (d, 2H, J = 8.0 Hz), 7.322 (d, 1H, J = 8.4 Hz), 7.000 (d, 1H, J = 8.4 Hz), 6.822 (dd, 1H, J = 2.4, 8.4 Hz), 6.796 (d, 1H, J = 2.4 Hz), 6.468 (d, 1H, J = 8.4 Hz), 4.809 (s, 1H), 4.648 (d, 1H, J = 10.8 Hz), 4.472 (d, 1H, J = 10.8 Hz), 3.736 (s, 3H), 3.058 (s, 1H), 2.691 (m, 2H, J = 6.8 Hz), 2.468 (s, 3H), 2.052 (s, 1H), 1.782 (t, 2H, J = 6.8 Hz), 1.336 (s, 3H), 1.328 (s, 3H).<br><br>$^{13}$C-NMR (CDCl$_3$): 159.968, 154.895, 151.277, 148.783, 145.947, 133.157, 130.033, 129.073, 129.003, 128.538, 124.642, 113.016, 112.478, 110.847, 109.011, 108.347, 74.093, 71.469, 69.727, 67.567, 55.458, 32.100, 26.700, 26.652, 21.733, 16.935. |
| Example 66 | 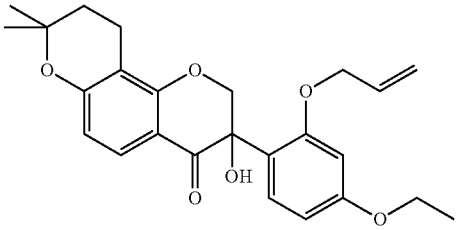<br>(Compound 4-b-63) | $^1$H-NMR (CDCl$_3$): 7.728 (d, 1H, J = 8.4 Hz), 7.377 (d, 1H, J = 8.4 Hz), 6.497 (d, 1H, J = 8.4 Hz), 6.459 (d, 1H, J = 8.4 Hz), 6.448 (s, 1H), 5.886 (m, 1H), 5.292 (dd, 1H, J = 1.2, 17.6 Hz), 5.175 (dd, 1H, J = 1.2, 10.4 Hz), 4.954 (d, 1H, J = 11.6 Hz), 4.477 (m, 2H), 4.311 (d, 1H, 11.6 Hz), 3.991 (q, 2H, J = 7.2 Hz), 3.632 (s, 1H), 2.642 (t, 2H, J = 6.8 Hz), 1.780 (t, 2H, J = 6.8 Hz), 1.387 (t, 3H, J = 7.2 Hz), 1.343 (s, 3H), 1.334 (s, 3H).<br>$^{13}$C-NMR (CDCl$_3$): 191.313, 1601475, 160.295, 160.222, 156.957, 132.660, 128.496, 126.688, 119.639, 117.609, 112.448, 112.245, 108.841, 105.398, 101.135, 75.479, 73.957, 73.863, 69.504, 63.489, 31.712, 26.900, 26.535, 16.483, 14.747. |
| Example 67 | 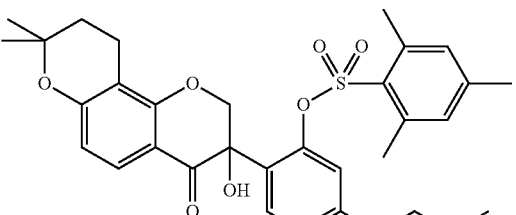<br>(Compound 4-b-42) | $^1$H-NMR (CDCl$_3$): 7.344 (d, 1H, J = 8.4 Hz), 7.060 (s, 2H), 7.037 (d, 1H, J = 8.4 Hz), 6.805 (dd, 1H, J = 2.4, 8.4 Hz), 6.467 (d, 1H, J = 8.4 Hz), 6.304 (d, 1H, J = 2.4 Hz), 4.843 (dd, 1H, J = 2.0 Hz), 4.713 (d, 1H, J = 10.8 Hz), 4.533 (dd, 1H, J = 2.0, 10.8 Hz), 3.664 (t, 2H, J = 6.8 Hz), 3.029 (s, 1H), 2.683 (m, 2H), 2.673 (s, 6H), 2.358 (s, 3H), 2.246 (s, 1H), 1.776 (t, 2H, J = 6.8 Hz), 1.701 (m, 2H), 1.325 (s, 6H), 0.955 (t, 3H, J = 7.2 Hz).<br>$^{13}$C-NMR (CDCl$_3$): 159.499, 154.828, 151.295, 149.054, 144.347, 139.945, 132.264, 132.048, 129.253, 129.132, 124.872, 113.0344, 112.904, 110.916, 108.969, 107.650, 74.080, 71.770, 70.039, 69.648, 67.570, 32.132, 26.695, 26.656, 22.690, 22.223, 21.125, 16.957, 10.281. |

TABLE 6-continued

| No. | Chemical structure | $^1$H-NMR, $^{13}$C-NMR (CDCl$_3$, δ) |
|---|---|---|
| Example 68 | (Compound 4-b-38) | $^1$H-NMR (CDCl$_3$): 7.800 (d, 2H, J = 8.0 Hz), 7.520 (d, 1H, J = 8.4 Hz), 7.334 (s, 1H, J = 1.6 Hz), 7.322 (d, 1H, J = 8.4 Hz), 7.229 (d, 2H, J = 8.0 Hz), 6.996 (dd, 1H, J = 1.6, 8.4 Hz), 6.404 (d, 1H, J = 8.4 Hz), 4.888 (d, 1H, J = 12.0 Hz), 4.252 (d, 1H, J = 12.0 Hz), 3.616 (s, 1H), 2.612 (q, 1H, J = 7.2 Hz), 2.578 (m, 2H), 2.414 (s, 3H), 1.762 (t, 2H, J = 6.8 Hz), 1.347 (s, 3H), 1.319 (s, 3H), 1.187 (t, 3H, J = 7.6 Hz).<br><br>$^{13}$C-NMR (CDCl$_3$): 190.631, 160.889, 160.351, 147.903, 146.648, 145.353, 133.062, 129.509, 128.777, 128.290, 127.422, 126.594, 125.721, 120.627, 112.419, 111.968, 108.765, 75.654, 73.650, 73.314, 31.652, 28.304, 26.940, 26.527, 21.693, 16.336, 14.910. |

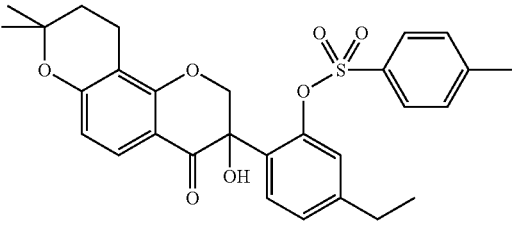

H-NMR data and C-NMR data of the compounds prepared in Examples 64 to 68 and represented by Formula 5-b are shown in the following Table 7.

TABLE 7

| No. | Chemical structure | $^1$H-NMR, $^{13}$C-NMR (CDCl$_3$, δ) |
|---|---|---|
| Example 64 | (Compound 5-b-43) | $^1$H-NMR (CDCl$_3$): 7.085 (d, 1H, J = 8.4 Hz), 7.056 (d, 1H, J = 8.4 Hz), 6.996 (s, 2H), 6.694 (d, 1H, J = 2.0 Hz), 6.512 (dd, 1H, J = 2.0, 8.4 Hz), 6.457 (d, 1H, J = 8.8 Hz), 5.92-6.02 (m, 1H), 5.378 (dd, 1H, J = 0.8, 17.2 Hz), 5.323(dd, 1H, J = 0.8, 10.4 Hz), 4.866 (d, 1H, J = 1.6 Hz), 4.631 (dd, 1H, J = 1.6, 10.8 Hz), 4.530 (m, 2H), 4.373 (dd, 1H, J = 1.6, 10.8 Hz), 4.241 (s, 1H), 2.60-2.7 4 (m, 2H), 2.580 (s, 6H), 2.336 (s, 3H), 1.765 (t, 2H, J = 7.2 Hz), 1.319 (s, 6H).<br><br>$^{13}$C-NMR (CDCl$_3$): 157.037, 154.916, 151.400, 149.797, 143.993, 140.412, 131.815, 131.281, 130.594, 128.409, 128.198, 127.099, 119.631, 114.215, 113.334, 110.521, 109.040, 107.427, 74.074, 71.726, 69.689, 67.186, 32.098, 31.554, 26.761, 26.589, 22.718, 21.086, 16.936, 14.092. |
| Example 65 | (Compound 5-b-37) | $^1$H-NMR (CDCl$_3$): 7.875 (d, 1H, J = 8.4 Hz), 7.640 (d, 2H, J = 8.0 Hz), 7.223 (d, 2H, J = 8.0 Hz), 7.042 (d, 1H, J = 8.4 Hz), 6.879 (dd, 1H, J = 2.4, 8.4 Hz), 6.706 (d, 1H, J = 2.4 Hz), 6.597 (d, 1H, J = 8.4 Hz), 5.046 (s, 2H), 4.546 (s, 2H), 3.794 (s, 3H), 2.749 (t, 2H, J = 6.8 Hz), 2.415 (s, 3H), 1.758 (t, 2H, J = 6.8 Hz), 1.332 (s, 6H).<br><br>$^{13}$C-NMR (CDCl$_3$): 193.321, 163.945, 156.181, 154.994, 149.466, 146.315, 132.356, 131.660, 130.052, 128.307, 128.143, 124.754, 122.182, 114.848, |

TABLE 7-continued

| No. | Chemical structure | ¹H-NMR, ¹³C-NMR (CDCl₃, δ) |
|---|---|---|
| | | 113.260, 113.172, 108.098, 77.774, 74.030, 61.494, 55.824, 32.133, 26.675, 21.734, 17.811. |
| Example 66 | 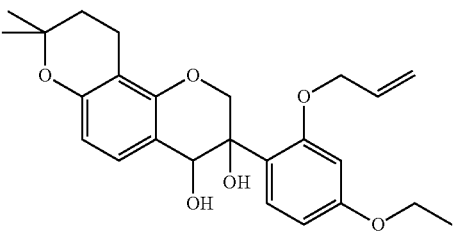<br>(Compound 5-b-63) | ¹H-NMR (CDCl₃): 7.065 (d, 1H, J = 8.4 Hz), 7.052 (d, 1H, J = 8.4 Hz), 6.552 (d, 1H, J = 2.4 Hz), 6.500 (dd, 1H, J = 2.4, 8.4 Hz), 6.462 (d, 1H, J = 8.4 Hz), 6.01~6.11 (m, 1H), 5.425 (d, 1H, J = 17.2 Hz), 5.332 (d, 1H, J = 10.8 Hz), 4.902 (s, 1H), 4.675 (d, 1H, J = 10.8 Hz), 4.637 (m, 2H), 4.438 (d, 1H, J = 10.8 Hz), 4.375 (s, 1H), 4.027 (q, 2H, J = 7.2 Hz), 2.711 (m, 2H), 2.673 (s, 6H), 1.776 (t, 2H, J = 6.8 Hz), 1.417 (t, 3H, J = 6.8 Hz), 1.326 (s, 5H).<br>¹³C-NMR (CDCl₃): 159.799, 157.445, 154.791, 151.567, 131.911, 128.749, 127.875, 120.172, 119.106, 113.415, 110.310, 108.970, 106.575, 105.446, 101.037, 73.989, 71.632, 69.578, 69.319, 67.253, 63.577, 32.163, 26.763, 26.606, 16.969, 14.732. |
| Example 67 | 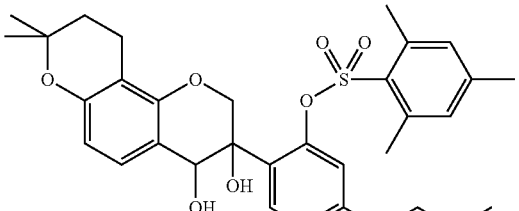<br>(Compound 5-b-42) | ¹H-NMR (CDCl₃): 7.979 (d, 1H, J = 8.4 Hz), 7.011 (d, 1H, J = 8.4 Hz), 6.970 (s, 2H), 6.852 (dd, 1H, J = 2.4, 8.4 Hz), 6.569 (d, 1H, J = 8.4 Hz), 6.182 (d, 1H, J = 2.4 Hz), 5.183 (s, 2H), 4.547 (s, 2H), 3.704 (t, 2H, J = 6.8 Hz), 2.783 (t, 2H, J = 6.8 Hz), 2.521 (s, 6H), 2.325 (s, 3H), 1.755 (t, 2H, J = 6.8 Hz), 1.707 (m, 2H), 1.325 (s, 6H), 0.956 (t, 3H, J = 6.4 Hz).<br><br>¹³C-NMR (CDCl₃): 193.349, 163.498, 156.236, 154.929, 149.805, 144.620, 140.311, 132.573, 131.963, 130.804, 127.966, 124.781, 122.253, 114.952, 113.711, 113.148, 107.229, 77.984, 73.991, 70.016, 61.574, 32.154, 26.639, 22.598, 22.074, 21.111, 17.789, 10.197. |
| Example 68 | 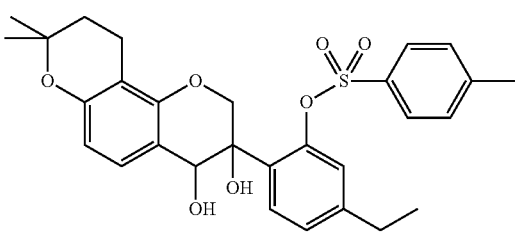<br>(Compound 5-b-38) | ¹H-NMR (CDCl₃): 7.942 (d, 2H, J = 8.0 Hz), 7.382 (d, 2H, J = 8.0 Hz), 7.319 (d, 1H, J = 8.4 Hz), 7.131 (dd, 1H, J = 1.6, 8.4 Hz), 7.057 (d, 1H, J = 1.6 Hz), 7.006 (d, 1H, J = 8.4 Hz), 6.473 (d, 1H, J = 8.4 Hz), 4.855 (dd, 1H, J = 1.6, 4.0 Hz), 4.679 (d, 1H, J = 10.8 Hz), 4.511 (dd, 1H, J = 1.6, 10.8 Hz), 3.121 (s, 1H), 2.700 (m, 2H), 2.602 (q, 2H, J = 7.6 Hz), 2.477 (s, 3H), 2.022 (d, 1H, J = 4.0 Hz), 1.785 (t, 2H, J = 7.2 Hz), 1.339 (s, 3H), 1.329 (s, 3H), 1.174 (t, 3H, J = 7.2 Hz)<br>¹³C-NMR (CDCl₃): 154.942, 151.312, 148.052, 146.244, 145.904, 133.243, 130.011, 129.917, 129.072, 128.574, 128.256, 126.629, 121.837, 112.988, 110.880, 109.043, 74.124, 71.623, 69.671, 67.518, 32.124, 28.102, 26.734, 26.666, 21.752, 16.956, 14.780. |

H-NMR data and C-NMR data of the 3-phenyl-2,8-dihydropyrano[2,3-f]chromene derivatives (compounds represented by Formula (I-b)) prepared in Examples 64 to 68 are shown in the following Table 8.

TABLE 8

| No. | Chemical structure | $^1$H-NMR, $^{13}$C-NMR (CDCl$_3$, δ) |
|---|---|---|
| Example 64 | 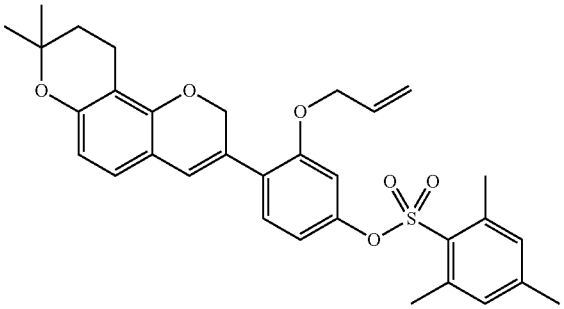<br>(Compound I-b-43) | $^1$H-NMR(CDCl$_3$): 7.166 (d, 1H, J = 8.4 Hz), 6.993 (s, 2H), 6.835 (d, 1H, J = 8.4 Hz), 6.533 (d, 1H, J = 2.0 Hz), 6.531 (s, 1H), 6.496 (dd, 1H, J = 2.0, 8.4 Hz), 6.383 (d, 1H, J = 8.4 Hz), 5.89~5.99 (m, 1H), 5.333 (dd, 1H, J = 1.6, 17.2 Hz), 5.253 (dd, 1H, J = 1.6, 10.4 Hz), 4.978 (s, 1H), 4.387 (m, 2H), 2.660 (t, 2H, J = 6.8 Hz), 2.584 (s, 6H), 2.334 (s, 3H), 1.780 (t, 2H, J = 6.8 Hz), 1.328 (s, 6H).<br><br>$^{13}$C-NMR (CDCl$_3$): 156.532, 155.059, 151.969, 149.435, 143.855, 140.475, 132.233, 131.748, 130.631, 128.979, 127.259, 126.825, 125.296, 123.562, 118.180, 115.139, 114.247, 110.121, 109.121, 106.795, 74.273, 69.923, 68.006, 32.065, 26.674, 22.761, 21.075, 16.912. |
| Example 65 | 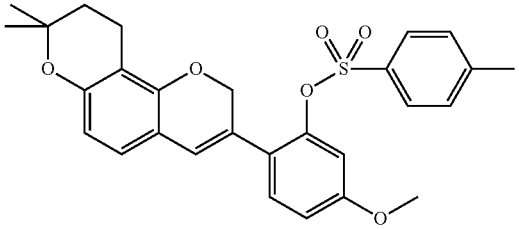<br>(Compound I-b-37) | $^1$H-NMR (CDCl$_3$): 7.563 (d, 2H, J = 8.0 Hz), 7.079 (d, 1H, J = 8.4 Hz), 7.031 (d, 2H, J = 8.0 Hz), 6.928 (d, 1H, J = 2.4 Hz), 6.799 (dd, 1H, J = 2.4, 8.4 Hz), 6.642 (d, 1H, J = 8.4 Hz), 6.358 (d, 1H, J = 8.4 Hz), 5.952 (s, 1H), 4.748 (s, 2H), 3.816 (s, 3H), 2.639 (t, 2H, J = 6.8 Hz), 2.286 (s, 3H), 1.805 (t, 2H, J = 6.8 Hz), 1.352 (s, 6H).<br><br>$^{13}$C-NMR (CDCl$_3$): 159.643, 155.038, 151.314, 147.553, 145.260, 132.171, 129.664, 129.462, 128.506, 125.030, 124.955, 124.808, 114.805, 113.658, 109.897, 109.168, 109.031, 74.303, 67.609, 55.640, 32.108, 26.696, 21.601, 16.897. |
| Example 66 | 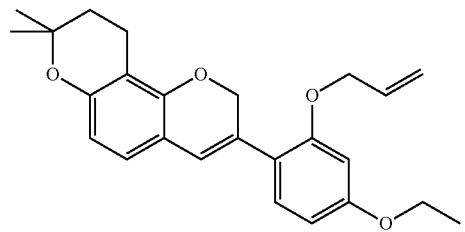<br>(Compound I-b-63) | $^1$H-NMR (CDCl$_3$): 1H-NMR (CDCl3): 7.218 (d, 1H, J = 8.4 Hz), 6.837 (d, 1H, J = 8.4 Hz), 6.512 (s, 1H), 6.485 (dd, 1H, J = 2.4, 8.4 Hz), 6.448 (d, 1H, J = 2.4 Hz), 6.378 (d, 1H, J = 8.4 Hz), 6.030 (m, 1H), 5.394 (m, 1H, J = 1.6, 17.2 Hz), 5.014 (m, 1H, J = 1.2, 10.4 Hz), 5.031 (s, 2H), 4.520 (m, 2H), 4.031 (q, 2H, J = 7.2 Hz), 2.674 (t, 2H, J = 6.8 Hz), 1.783 (t, 2H, J = 6.8 Hz), 1.417 (t, 3H, J = 7.2 Hz), 1.329 (s, 6H).<br>$^{13}$C-NMR (CDCl$_3$): 159.734, 157.161, 154.585, 151.723, 132.965, 129.261, 128.058, 124.990, 121.686, 121.251, 117.691, 115.573, 109.894, 109.065, 105.579, 100.288, 74.154, 69.166, 68.451, 63.582, 32.157, 26.698, 16.980, 14.813. |

TABLE 8-continued

| No. | Chemical structure | ¹H-NMR, ¹³C-NMR (CDCl₃, δ) |
|---|---|---|
| Example 67 | 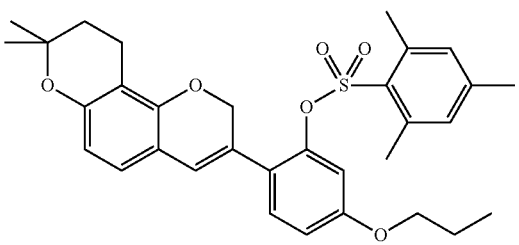<br>(Compound I-b-42) | ¹H-NMR (DMSO-d₆): 7.231 (d, 1H, J = 8.4 Hz), 6.988 (s, 2H), 6.907 (dd, 1H, J = 2.4, 8.4 Hz), 6.775 (d, 1H, J = 8.4 Hz), 6.386 (s, 1H), 6.338 (d, 1H, J = 2.4 Hz), 6.290 (d, 1H, J = 8.4 Hz), 4.771 (s, 2H), 3.748 (t, 2H, J = 6.8 Hz), 2.543 (t, 2H, J = 6.8 Hz), 2.374 (s, 6H), 2.199 (s, 3H), 1.738 (t, 2H, J = 6.8 Hz), 1.635 (m, 2H), 1.274 (s, 6H), 0.906 (t, 3H, J = 7.2 Hz).<br><br>¹³C-NMR (DMSO-d6): 158.361, 154.547, 150.785, 146.861, 144.125, 139.561, 131.785, 130.603, 129.888, 125.248, 124.309, 124.180, 123.069, 114.174, 113.953, 109.447, 108.731, 108.421, 73.993, 69.354, 67.205, 31.380, 26.338, 22.333, 21.672, 20.484, 16.472, 10.093. |
| Example 68 | 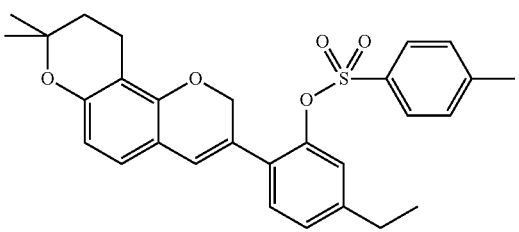<br>(Compound I-b-38) | ¹H-NMR (CDCl₃): 7.553 (d, 2H, J = 8.0 Hz), 7.084 (s, 2H), 7.030 (d, 2H, J = 8.0 Hz), 6.657 (d, 1H, J = 8.4 Hz), 6.364 (d, 1H, J = 8.4 Hz), 6.024 (s, 1H), 4.777 (s, 2H), 2.62~2.69 (m, 4H), 2.287 (s, 3H), 1.807 (t, 2H, J = 6.8 Hz), 1.354 (s, 6H), 1.216 (t, 3H, J = 7.2 Hz).<br><br>¹³C-NMR (CDCl₃): 155.137, 151.431, 146.824, 145.393, 145.132, 132.327, 129.820, 129.413, 128.965, 128.477, 126.926, 125.146, 125.036, 124.061, 123.096, 114.756, 109.916, 109.031, 74.309, 67.552, 32.094, 28.293, 26.685, 21.574, 16.885, 15.127. |

Further, H-NMR data and C-NMR data of the compounds represented by Formula (II-c) prepared by using the 3-phenyl-2,8-dihydropyrano[2,3-f]chromene derivatives (compounds represented by Formula (I-b)) prepared in Examples 64 to 68 are shown in the following Table 9.

TABLE 9

| No. | Chemical structure | ¹H-NMR, ¹³C-NMR (CDCl₃, δ) |
|---|---|---|
| Example 64 | 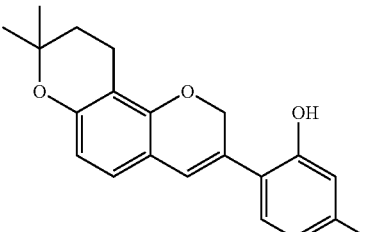<br>(Compound II-c-9) | ¹H-NMR (DMSO-d6): 9.576 (s, 1H), 9.375 (s, 1H), 7.017 (d, 1H, J = 8.4 Hz), 6.819 (d, 1H, J = 8.4 Hz), 6.551 (s, 1H), 6.336 (d, 1H, J = 2.4 Hz), 6.273 (d, 1H, J = 8.4 Hz), 6.241 (dd, 1H, J = 2.4, 8.4 Hz), 4.973 (s, 2H), 2.558 (t, 2H, J = 6.8 Hz), 1.719 (t, 2H, J = 6.8 Hz), 1.251 (s, 6H).<br><br>¹³C-NMR (DMSO-d6): 158.036, 156.156, 153.837, 150.920, 128.672, 128.113, 124.723, 119.513, 116.213, 115.309, 109.383, 108.478, 106.794, 102.794, 73.852, 67.702, 31.472, 26.399, 16.578 |

TABLE 9-continued

| No. | Chemical structure | $^1$H-NMR, $^{13}$C-NMR (CDCl$_3$, δ) |
|---|---|---|
| Example 66 | 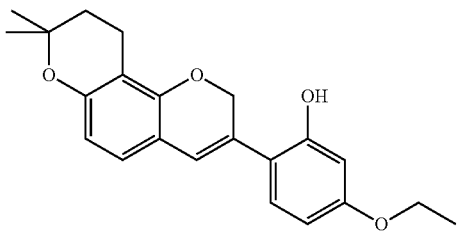<br>(Compound II-c-2) | $^1$H-NMR (CDCl3): 7.068 (d, 1H, J = 8.4 Hz), 6.825 (d, 1H, J = 8.4 Hz), 6.543 (s, 1H), 6.497 (dd, 1H, J = 2.4, 8.4 Hz), 6.461 (d, 1H, J = 2.4 Hz), 6.397 (d, 1H, J = 8.4 Hz), 5.0434 (s, 1H), 4.986 (s, 2H), 4.015 (q, 2H, J = 7.2 Hz), 2.676 (t, 2H, J = 6.8 Hz), 1.796 (t, 2H, J = 6.8 Hz), 1.411 (t, 3H, J = 7.2 Hz), 1.341 (s, 6H).<br><br>$^{13}$C-NMR (CDCl3): 159.657, 155.106, 153.958, 151.415, 128.702, 125.829, 125.106, 122.771, 117.452, 114.449, 110.146, 109.272, 107.291, 102.068, 74.338, 68.351, 63.547, 32.071, 26.676, 16.911, 14.754. |
| Example 67 | 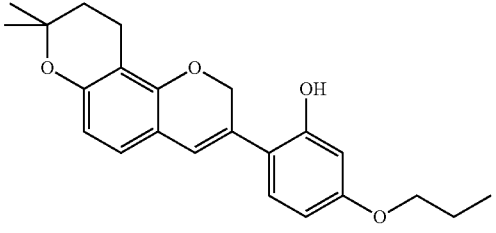<br>(Compound II-c-3) | $^1$H-NMR (CDCl3): .062 (d, 1H, J = 8.4 Hz), 6.813 (d, 1H, J = 8.4 Hz), 6.531 (s, 1H), 6.489 (dd, 1H, J = 2.4, 8.4 Hz), 6.447 (d, 1H, J = 2.4 Hz), 6.389 (d, 1H, J = 8.4 Hz), 5.537 (s, 1H), 4.981 (s, 2H), 3.884 (t, 2H, J = 6.8 Hz), 2.666 (t, 2H, J = 6.8 Hz), 1.74~1.96 (m, 4H), 1.331 (s, 6H), 1.020 (t, 3H, J = 7.2 Hz).<br><br>$^{13}$C-NMR (CDCl3): 159.829, 155.021, 153.989, 151.390, 128.716, 125.980, 125.092, 122.652, 117.476, 114.538, 110.127, 109.257, 107.274, 102.180, 74.344, 69.592, 68.332, 32.062, 26.658, 22.471, 16.902, 10.465. |
| Example 68 | 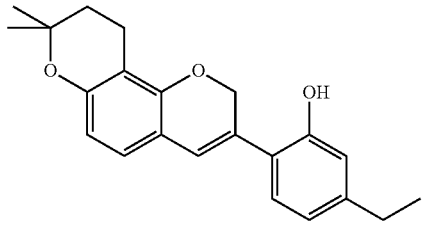<br>(Compound II-c-13) | $^1$H-NMR (CDCl3): 1H-NMR (DMSO-d6): 9.590 (s, 1H), 7.100 (d, 1H, J = 8.4 Hz), 6.828 (d, 1H, J = 8.4 Hz), 6.669 (d, 1H, J = 1.6 Hz), 6.628 (dd, 1H, J = 1.6, 8.4 Hz), 6.621 (s, 1H), 6.264 (d, 1H, J = 8.4 Hz), 4.980 (s, 2H), 2.47~2.58 (m, 4H), 1.700 (t, 2H, J = 6.8 Hz), 1.230 (s, 6H), 1.121 (t, 3H, J = 7.2 Hz). |

From the foregoing, the present invention has been reviewed mainly based on the preferred examples thereof. A person with ordinary skill in the art to which the present invention pertains will be able to understand that the present invention may be implemented in a modified form without departing from the essential characteristics of the present invention. Therefore, the disclosed examples should be considered not from a restrictive viewpoint, but from an explanatory viewpoint. The scope of the present invention is defined not in the above-described explanation, but in the claims, and it should be interpreted that all the differences within a range equivalent thereto are included in the present invention.

What is claimed is:

1. A method for synthesizing a 3-phenyl-2,8-dihydropyrano[2,3-f]chromene derivative, the method comprising:

A) preparing a compound of Formula 3 by coupling a compound represented by Formula 1 with a compound represented by Formula 2;

B) synthesizing a compound of Formula 4 by cyclizing the compound of Formula 3;

C) preparing a compound of Formula 5 by reducing the compound of Formula 4; and

D) preparing a compound of Formula (I) by subjecting the compound of Formula 5 to a reductive elimination reaction:

[Reaction Formula 1]

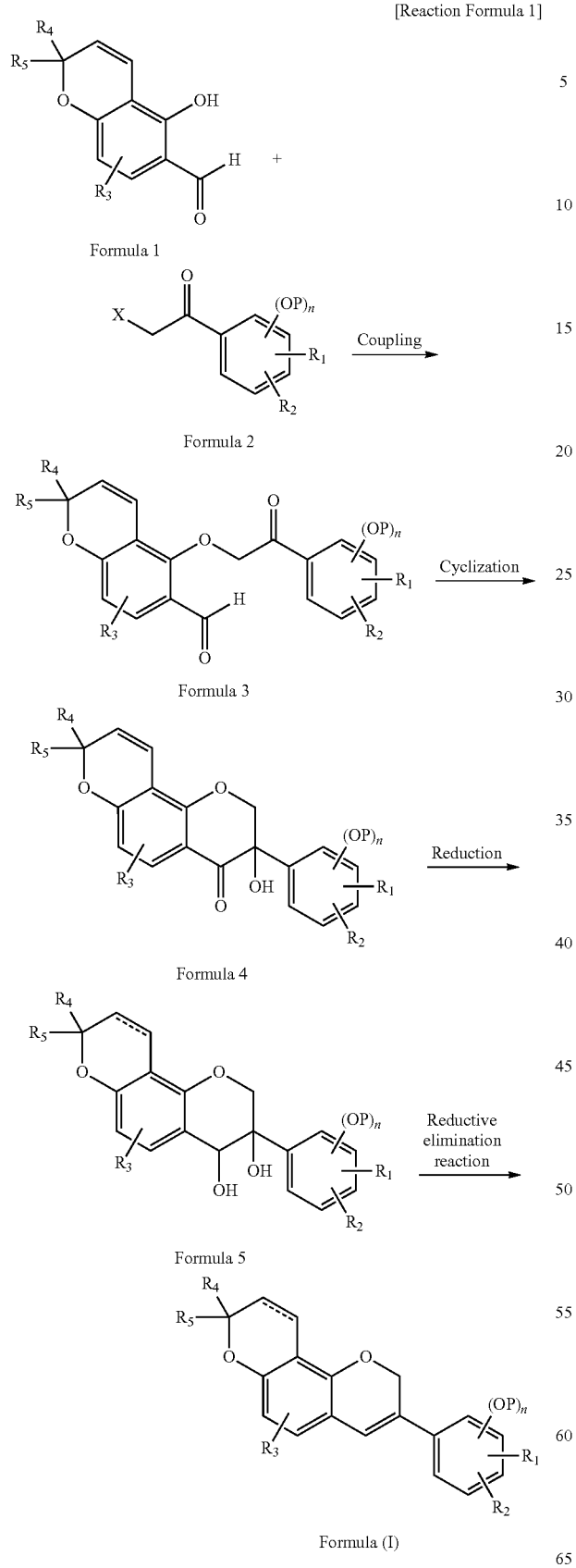

Formula 1
Formula 2
Formula 3
Formula 4
Formula 5
Formula (I)

in the formulae,

R₁ and R₂ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

R₃ is a hydrogen atom, a $C_1$ to $C_2$ alkyl group, or a $C_1$ to $C_2$ alkoxy group;

R₄ and R₅ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

X is Br;

a dotted line is a selective double bond;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

2. The method of claim 1, wherein when the 3-phenyl-2,8-dihydropyrano[2,3-f]chromene derivative is a compound represented by Formula (I-b):

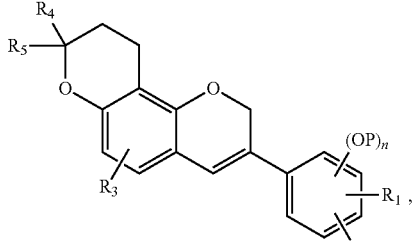

Formula (I-b)

Step C) comprises preparing a compound represented by the following Formula 4-b by selectively reducing a carbon-to-carbon double bond of a dihydropyran ring in the compound represented by Formula 4:

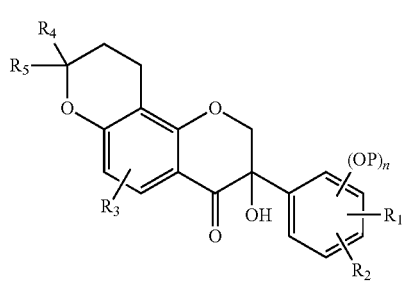

Formula 4-b

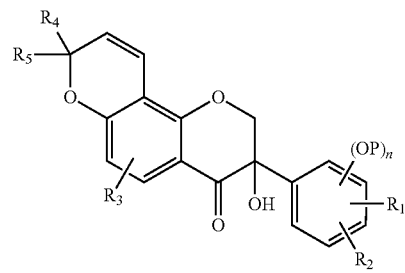

Formula 4 in the formulae, $R_1$ and $R_2$ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

$R_3$ is a hydrogen atom, a $C_1$ to $C_2$ alkyl group, or a $C_1$ to $C_2$ alkoxy group;

$R_4$ and $R_5$ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

3. The method of claim 1, wherein the coupling reaction is performed under basic conditions.

4. The method of claim 3, wherein the basic conditions are generated by addition of one or more weak basic compounds selected from the group consisting of ammonia, aluminum hydroxide, magnesium hydroxide, ammonium hydroxide, and potassium carbonate.

5. The method of claim 1, wherein the cyclization reaction is performed by using a thiazolium salt, a triazolium salt, or a 6,7-dihydro-5H-pyrrolo[2,1-c][1,2,4]triazolium salt as a catalyst.

6. The method of claim 1, wherein the reductive elimination reaction is performed in the presence of low valent titanium.

7. A compound represented by the following Formula 4, a salt or solvate thereof:

in the formula, $R_1$ and $R_2$ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

$R_3$ is a hydrogen atom, a $C_1$ to $C_2$ alkyl group, or a $C_1$ to $C_2$ alkoxy group;

$R_4$ and $R_5$ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

8. A compound represented by the following Formula 4-b, a salt or solvate thereof:

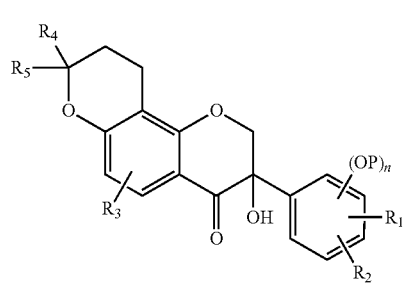

Formula 4-b in the formula, $R_1$ and $R_2$ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

$R_3$ is a hydrogen atom, a $C_1$ to $C_2$ alkyl group, or a $C_1$ to $C_2$ alkoxy group;

$R_4$ and $R_5$ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

9. A compound represented by the following Formula 5, a salt or solvate thereof:

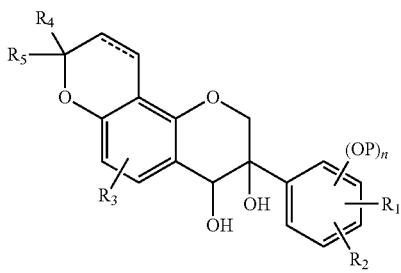

Formula 5 in the formula, $R_1$ and $R_2$ are each independently a hydrogen atom; a substituted or unsubstituted straight or branched $C_1$ to $C_6$ alkyl group; a halogen atom; a substituted or unsubstituted straight or branched $C_1$ to $C_6$ alkoxy group; a substituted or unsubstituted straight or branched $C_1$ to $C_4$ thioalkyl group; a substituted or unsubstituted $C_6$ to $C_{12}$ aryl group; a substituted or unsubstituted allyloxy group; or a substituted or unsubstituted $C_6$ to $C_{12}$ aryloxy group;

$R_3$ is a hydrogen atom, a $C_1$ to $C_2$ alkyl group, or a $C_1$ to $C_2$ alkoxy group;

$R_4$ and $R_5$ are each independently a hydrogen atom or a $C_1$ to $C_6$ alkyl group;

P means a protecting group, which is a substituted or unsubstituted benzyl group or allyl group; a tert-butyldimethylsilyl (TBDMS) group; a tert-butyldiphenylsilyl (TBDPS) group; a methylphenylsilyl group; a trimethylphenylsilyl group; methanesulfonyl ($MeSO_2$) or p-toluenesulfonyl (p-$TsSO_2$); or a trimethylphenylsulfonyl group;

a dotted line is a selective double bond;

n is an integer from 1 to 3;

a plurality of OP's are the same as or different from each other; and in the case of the substituted alkyl group, the substituted alkoxy group, the substituted thioalkyl group, the substituted aryl group, the substituted allyloxy group, the substituted aryloxy group, the substituted benzyl group, and the substituted allyl group, the substituent is a halogen atom, a straight or branched $C_1$ to $C_5$ alkyl group, a straight or branched $C_1$ to $C_5$ alkoxy group, a straight or branched $C_1$ to $C_3$ thioalkyl group, or a nitro group.

* * * * *